US011160873B2

(12) United States Patent
Lackmann et al.

(10) Patent No.: US 11,160,873 B2
(45) Date of Patent: Nov. 2, 2021

(54) ANTI-METALLOPROTEASE ANTIBODY FOR DIAGNOSIS AND TREATMENT OF CANCERS

(71) Applicants: Monash University, Clayton (AU); Memorial Sloan-Kettering Cancer Centre, New York, NY (US); Ludwig Institute for Cancer Research Ltd., New York, NY (US); Olivia Newton-John Cancer Research Institute, Heidelberg (AU); Beate Lackmann, St. Andrews Beach (AU)

(72) Inventors: Martin Lackmann, St. Andrews Beach (AU); Peter W. Janes, Hawthorn East (AU); Lakmali Atapattu Mudiyanselage, Hughesdale (AU); Andrew M. Scott, Krew East (AU); Dimitar B. Nikolov, New York, NY (US); Nayanendu Saha, Jackson Heights, NY (US)

(73) Assignees: Monash University, Clayton (AU); Memorial Sloan-Kettering Cancer Centre, New York, NY (US); Ludwig Institute for Cancer Research Ltd., New York, NY (US); Olivia Newton-John Cancer Research Institute, Heidelberg (AU)

(*) Notice: Subject to any disclaimer, the term of this patent is extended or adjusted under 35 U.S.C. 154(b) by 40 days.

(21) Appl. No.: 16/028,130

(22) Filed: Jul. 5, 2018

(65) Prior Publication Data
US 2019/0105405 A1 Apr. 11, 2019

Related U.S. Application Data

(63) Continuation-in-part of application No. 15/116,487, filed as application No. PCT/AU2015/050036 on Feb. 4, 2015, now Pat. No. 10,023,653.

(60) Provisional application No. 61/935,552, filed on Feb. 4, 2014.

(51) Int. Cl.
| | |
|---|---|
| *G01N 33/53* | (2006.01) |
| *C07K 16/18* | (2006.01) |
| *A61K 39/395* | (2006.01) |
| *A61K 47/68* | (2017.01) |
| *C07K 16/40* | (2006.01) |
| *C07K 16/30* | (2006.01) |
| *A61P 35/00* | (2006.01) |
| *C07K 16/28* | (2006.01) |
| *A61K 39/00* | (2006.01) |

(52) U.S. Cl.
CPC ...... *A61K 47/6871* (2017.08); *A61K 47/6803* (2017.08); *A61K 47/6843* (2017.08); *A61K 47/6851* (2017.08); *A61K 47/6875* (2017.08); *A61K 47/6887* (2017.08); *A61K 47/6891* (2017.08); *A61P 35/00* (2018.01); *C07K 16/283* (2013.01); *C07K 16/2896* (2013.01); *C07K 16/3076* (2013.01); *C07K 16/40* (2013.01); *A61K 2039/505* (2013.01); *C07K 2317/24* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,371,383 | B2* | 5/2008 | Reed | C07K 16/244 |
| | | | | 424/145.1 |
| 8,735,554 | B2* | 5/2014 | Cote | C07K 16/1271 |
| | | | | 435/7.32 |
| 9,803,026 | B2* | 10/2017 | Yamazaki | G01N 33/5058 |

FOREIGN PATENT DOCUMENTS

WO WO 2006/063415 A1 6/2006

OTHER PUBLICATIONS

Paul, Fundamental Immunology, 3rd Edition, 1993, pp. 292-295, under the heading "Fv Structure and Diversity in Three Dimensions" (Year: 1993).*
Rudikoff et al Proc. Natl. Acad. Sci.USA, 79(6):1979-1983, Mar. 1982 (Year: 1982).*
Colman P. M. Research in Immunology, 145:33-36, 1994 (Year: 1994).*
Piatesi et al ChemBio Chem 5: 460-466, 2004 (Year: 2004).*
"ADAM10, ENSG00000137845", IST Online Database (Last accessed Oct. 6, 2017), 2 pp. http://ist.medisapiens.com/.
Atapattu et al., *Journal of Cell Science*, 125: 6084-6093 (2012).
Atapattu et al., *Cell Adhesion & Migration*, 8: 294-307 (2014).
Bass et al., *Biochem. J.*, 429: e3-e5 (2010).
Duffy et al., *Clinical Proteomics*, 8:9 (2011).

(Continued)

*Primary Examiner* — Joanne Hama
*Assistant Examiner* — Jon M Lockard
(74) *Attorney, Agent, or Firm* — Leydig, Voit & Mayer, Ltd.

(57) ABSTRACT

Expression of proteolytically active, high molecular weight ADAM10 protease is relatively increased in tumour cells that also express the putative tumour stem cell marker CD133. A recombinant humanized antibody or antibody fragment based on 8C7 monoclonal antibody may be used to selectively bind to proteolytically active, high molecular weight ADAM10 protease to thereby detect tumour cells and also as a therapeutic agent for treating cancers, tumours and other malignancies inclusive of leukemia, lymphoma, lung cancer, colon cancer, adenoma, neuroblastoma, brain tumour, renal tumour, prostate cancer, sarcoma and/or melanoma.

18 Claims, 23 Drawing Sheets
Specification includes a Sequence Listing.

(56) References Cited

OTHER PUBLICATIONS

Hall et al., *Cancer Research*, 72(14) Abstract (2012).
Mullooly et al., "ADAM10: a new player in breast cancer progression?" *British Journal of Cancer*, 113: 945-951 (2015).
Murphy, "The ADAMs: signalling scissors in the tumour microenvironment", *Nature Reviews: Cancer*, 8: 929-941 (2008).
Rappa et al., *Molecular Cancer*, 12(62): 1-17 (2013).
Rath et al., *PLoS One*, 8(1): 1-10 (2013).
Australian Patent Office, Written Opinion of The International Searching Authority in International Application No. PCT/AU2015/050036 (dated Apr. 27, 2015).
Australian Patent Office, International Search Report in International Application No. PCT/AU2015/050036 (dated Apr. 27, 2015).

\* cited by examiner

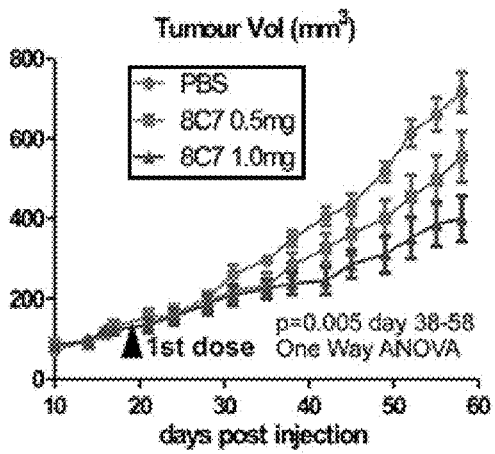
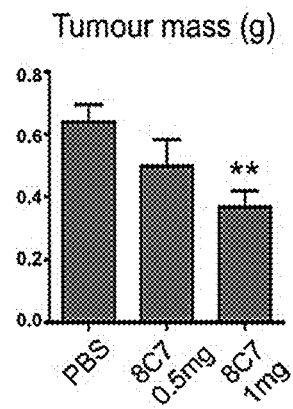
FIG. 1A  FIG. 1B
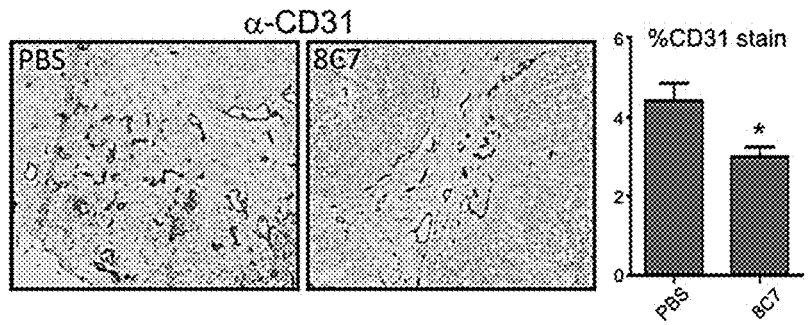
FIG. 1C
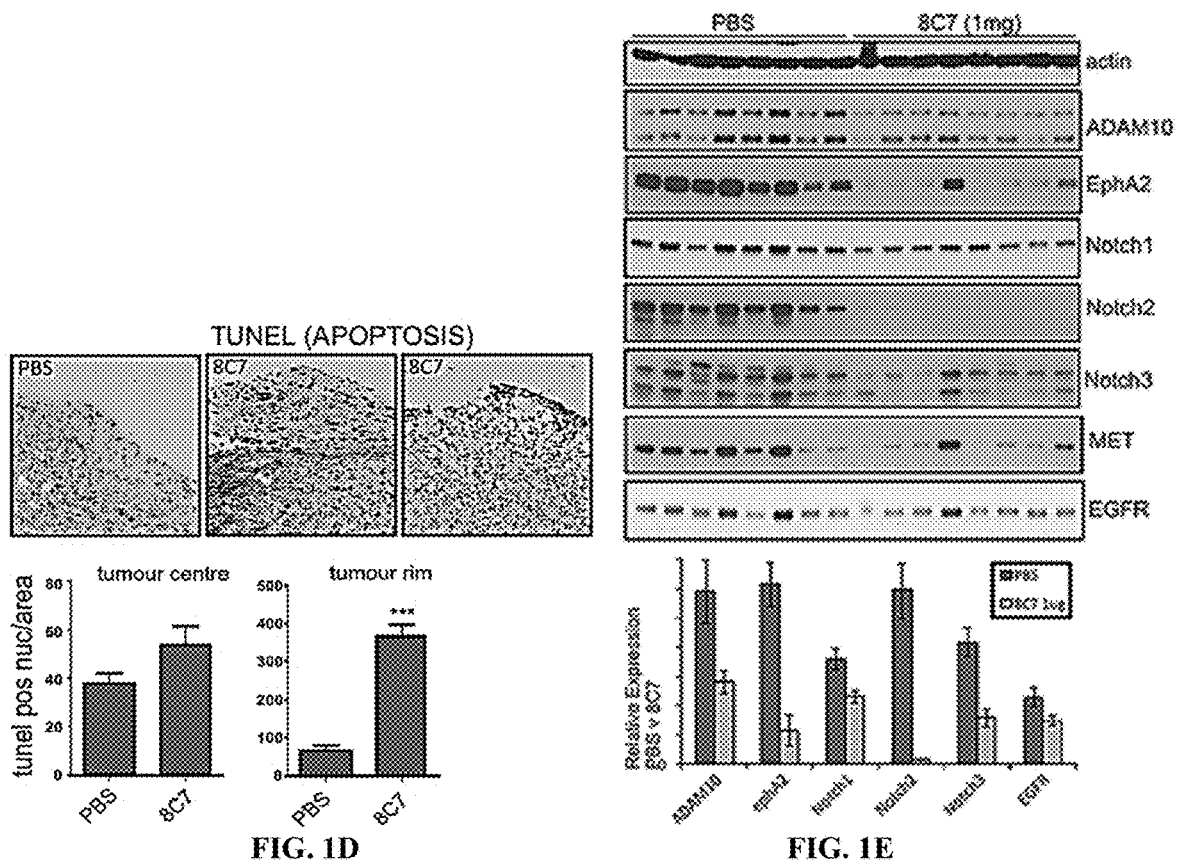
FIG. 1D  FIG. 1E

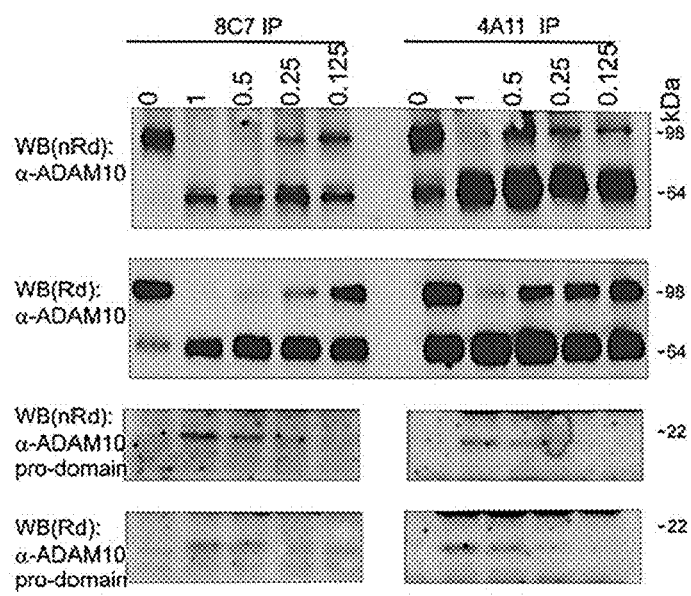
FIG. 13A
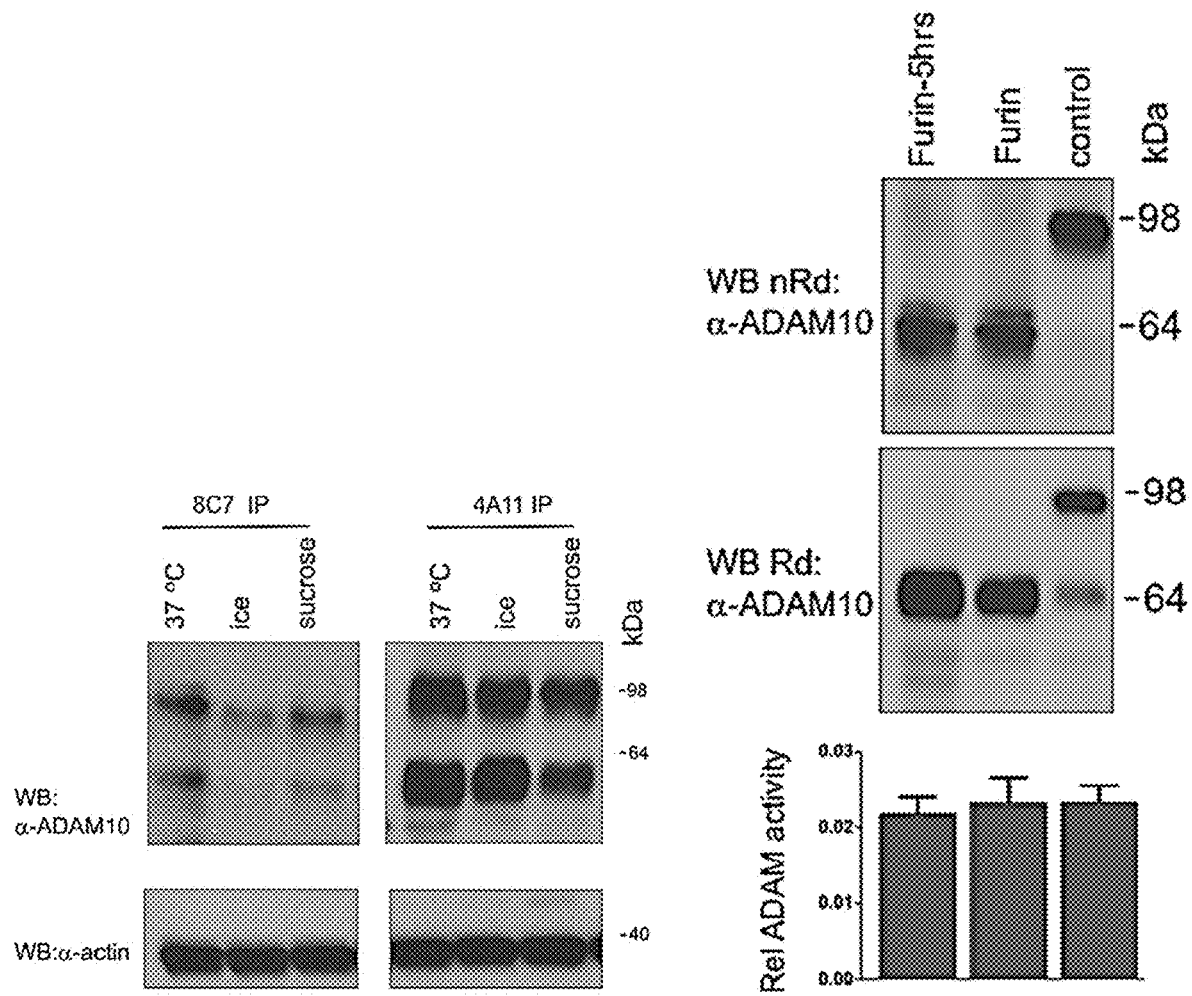
FIG. 13B
FIG. 14 mu8C7HC  E V Q L Q Q S G A E L A R P G S S V K L S C K A S G Y T F T N Y W L Q W V K Q R  40
hu8C7HC  E V Q L Q Q S G A E L A K P G S S V K L S C K A S G Y T F T N Y W L Q W V K Q R  40 mu8C7HC  T G Q G L E W I G A I Y P R D G D A K Y S Q K F K D K A S L T V N E S S S T A Y  80
hu8C7HC  P G Q G L E W I G A I Y P R D G D A K Y S Q K F K D K A S I T V N E S T S T A Y  80 mu8C7HC  M H L S A L A S E D S A V Y Y C A R A N Y G L Y Y A M D R W G Q G T S V T V S S  122
hu8C7HC  M H L S S L R S E D T A V Y Y C A R A N Y G L Y Y A M D R W G Q G T T V T V S S  122 mu8C7 LC  D I F L T Q S P A N M S V S P G E R V S F S C R A S Q N I G T N I H W Y Q Q R T – 40
hu8C7 LC  D I V L T Q S P A F M S V S P G E R V S V S C R A S Q N I G T N I H W Y Q Q R P – 40 mu8C7 LC  N G S P R L L I K Y A S E S I S G I P S R F S G S G S G T D F I L S I N T V E S – 80
hu8C7 LC  D Q S P R L L I K Y A S E S I S G I P S R F S G S G S G T D F Y L T I N S V E S – 80 mu8C7 LC  E D I A V Y F C Q Q S N R W P F T F G S G T K L E V I R                          – 108
hu8C7 LC  E D I A V Y F C Q Q S N R W P F T F G S G T K L E V K R                          – 108

FIG. 25 hu8C7 HC variable region DNA sequence:

GAGGTGCAGCTGCAGCAGTCCGGAGCTGAGCTGGCTAAGCCAGGCTCCAGCGTGAA
GCTGTCTTGCAAGGCCTCCGGCTACACCTTCACAAACTATTGGCTGCAGTGGGTGAA
GCAGAGGCCAGGACAGGGACTGGAGTGGATCGGCGCCATCTACCCTAGGGACGGC
GATGCTAAGTATAGCCAGAAGTTTAAGGACAAGGCCTCTATCACCGTGAACGAGTC
CACCAGCACAGCTTACATGCACCTGTCTTCCCTGAGGAGCGAGGACACAGCCGTGT
ACTATTGTGCCCGGGCTAATTATGGCCTGTACTATGCTATGGATAGATGGGGCCAGG
GCACCACAGTGACCGTGAGCTCT (SEQ ID NO:5)

hu8C7 LC variable region DNA sequence:

GACATCGTGCTGACCCAGTCTCCAGCCTTCATGTCCGTGAGCCCCGGCGAGAGGGT
GTCCGTGTCCTGCCGGGCTTCTCAGAACATCGGCACAAATATCCACTGGTACCAGCA
GAGACCCGATCAGTCCCCTCGCCTGCTGATCAAGTATGCCAGCGAGTCTATCTCCGG
CATCCCTAGCAGGTTCAGCGGCTCTGGCTCCGGAACCGACTTTTACCTGACAATCAA
CAGCGTGGAGTCTGAGGATATCGCCGTGTACTTTGTCAGCAGTCCAATAGATGGCC
ATTCACCTTTGGCAGCGGCACAAAGCTGGAGGTGAAGCGT (SEQ ID NO:6)

FIG. 26

Light chain

```
  1 T  V  A  A  P  S  V  F  I  F  P  P  S  D  E  Q  L  K  S  G
  1 ACTGTGGCTGCACCATCTGTCTTCATCTTCCCACCCTCCGACGAGCAGCTGAAGTCCGGC
 21 T  A  S  V  V  C  L  L  N  N  F  Y  P  R  E  A  K  V  Q  W
 61 ACCGCCTCCGTGGTGTGCCTGCTGAACAACTTCTACCCCCGCGAGGCCAAGGTGCAGTGG
 41 K  V  D  N  A  L  Q  S  G  N  S  Q  E  S  V  T  E  Q  D  S
121 AAGGTGGACAACGCCCTGCAGTCCGGCAACTCCCAGGAATCCGTCACCGAGCAGGACTCC
 61 K  D  S  T  Y  S  L  S  S  T  L  T  L  S  K  A  D  Y  E  K
181 AAGGACAGCACCTACTCCCTGTCCTCCACCCTGACCCTGTCCAAGGCCGACTACGAGAAG
 81 H  K  V  Y  A  C  E  V  T  H  Q  G  L  S  S  P  V  T  K  S
241 CACAAGGTGTACGCCTGCGAAGTGACCCACCAGGGCCTGTCCAGCCCCGTGACCAAGTCC
101 F  N  R  G  E  C  *  *
301 TTCAACCGGGGCGAGTGCTGATGA
```

FIG. 27A

Heavy chain

```
  1 S  T  K  G  P  S  V  F  P  L  A  P  S  S  K  S  T  S  G  G
  1 TCCACCAAGGGCCCATCGGTCTTCCCCCTGGCCCCATCCTCCAAGTCCACCTCTGGCGGC
 21 T  A  A  L  G  C  L  V  K  D  Y  F  P  E  P  V  T  V  S  W
 61 ACCGCCGCTCTGGGCTGCCTGGTGAAAGACTACTTCCCCGAGCCCGTGACCGTGTCCTGG
 41 N  S  G  A  L  T  S  G  V  H  T  F  P  A  V  L  Q  S  S  G
121 AACTCTGGCGCCCTGACCTCCGGCGTGCACACCTTTCCAGCCGTGCTGCAGTCCTCCGGC
 61 L  Y  S  L  S  S  V  V  T  V  P  S  S  S  L  G  T  Q  T  Y
181 CTGTACTCCCTGTCCTCCGTGGTGACAGTGCCCTCCTCCAGCCTGGGCACCCAGACCTAC
 81 I  C  N  V  N  H  K  P  S  N  T  K  V  D  K  K  V  E  P  K
241 ATCTGCAACGTGAACCACAAGCCCTCCAACACCAAGGTGGACAAGAAGGTGGAACCCAAG
101 S  C  D  K  T  H  T  C  P  P  C  P  A  P  E  L  L  G  G  P
301 TCCTGCGACAAGACCCACACCTGTCCCCCCTGCCCTGCCCCTGAACTGCTGGGCGGACCC
121 S  V  F  L  F  P  P  K  P  K  D  T  L  M  I  S  R  T  P  E
361 TCCGTGTTCCTGTTCCCCCCAAAGCCCAAGGACACCCTGATGATCTCCCGGACCCCCGAA
141 V  T  C  V  V  V  D  V  S  H  E  D  P  E  V  K  F  N  W  Y
421 GTGACCTGCGTGGTGGTGGACGTGTCCCACGAGGACCCTGAAGTGAAGTTCAATTGGTAC
161 V  D  G  V  E  V  H  N  A  K  T  K  P  R  E  E  Q  Y  N  S
481 GTGGACGGCGTGGAAGTGCACAATGCCAAGACCAAGCCCAGAGAGGAACAGTACAACTCC
181 T  Y  R  V  V  S  V  L  T  V  L  H  Q  D  W  L  N  G  K  E
541 ACCTACCGGGTGGTGTCCGTGCTGACCGTGCTGCACCAGGATTGGCTGAACGGCAAAGAG
201 Y  K  C  K  V  S  N  K  A  L  P  A  P  I  E  K  T  I  S  K
601 TACAAGTGCAAGGTCTCCAACAAGGCCCTGCCAGCCCCCATCGAAAAGACCATCTCCAAG
221 A  K  G  Q  P  R  E  P  Q  V  Y  T  L  P  P  S  R  D  E  L
661 GCCAAGGGCCAGCCCCGCGAGCCTCAGGTGTACACCCTGCCTCCCAGCCGGGACGAGCTG
241 T  K  N  Q  V  S  L  T  C  L  V  K  G  F  Y  P  S  D  I  A
721 ACCAAGAACCAGGTGTCCCTGACCTGTCTGGTGAAAGGCTTCTACCCCTCCGATATCGCC
261 V  E  W  E  S  N  G  Q  P  E  N  N  Y  K  T  T  P  P  V  L
781 GTGGAATGGGAGTCCAACGGCCAGCCCGAGAACAACTACAAGACCACCCCCCCTGTGCTG
281 D  S  D  G  S  F  F  L  Y  S  K  L  T  V  D  K  S  R  W  Q
841 GACTCCGACGGCTCATTCTTCCTGTACTCCAAGCTGACCGTGGACAAGTCCCGGTGGCAG
301 Q  G  N  V  F  S  C  S  V  M  H  E  A  L  H  N  H  Y  T  Q
901 CAGGGCAACGTGTTCTCCTGCTCCGTGATGCACGAGGCCCTGCACAACCACTACACCCAG
321 K  S  L  S  L  S  P  G  K  *  *
961 AAGTCCCTGTCCCTGAGCCCCGGCAAGTGATGA
```

FIG. 27B

ANTI-METALLOPROTEASE ANTIBODY FOR DIAGNOSIS AND TREATMENT OF CANCERS

CROSS-REFERENCE TO RELATED APPLICATIONS

This patent application is a continuation-in-part of copending U.S. patent application Ser. No. 15/116,487, filed Aug. 3, 2016, which is a U.S. national phase of International Patent Application No. PCT/AU2015/050036, filed Feb. 4, 2015, which application claims the benefit of U.S. Provisional Patent Application No. 61/935,552, filed Feb. 4, 2014, each of which is incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 19,299 Byte ASCII (Text) file named "739707_ST25.txt," created on Jun. 8, 2021.

TECHNICAL FIELD

This invention relates to an antibody to bind a proteolytically active form of an ADAM protease. More particularly, this invention relates to diagnosis and/or treatment of cancers using an antibody that binds a proteolytically active form of an ADAM protease that is expressed by tumour cells.

BACKGROUND

ADAM ('A Disintegrin And Metalloprotease') proteases catalyse the release of a range of cell surface proteins, activating receptor tyrosine kinase (RTK), Notch, cytokine-, chemokine- and adhesion signalling pathways important in normal and oncogenic development. Prominent oncogenic substrates include ligands and receptors in the Notch, erbB and Eph families, cytokines (TNFα, IL6), FASL, Slit, L-selectin and cadherins[1], which are all shed by one of the two closely related and widely-expressed proteases ADAM10 and ADAM17 (TACE). These proteases are also frequently over-expressed in cancers, correlating with aberrant signalling and poor cancer prognosis in cancers of the colon, lung, stomach, uterus and ovary[1,2], and as potent activators of key oncogenic pathways, recognized targets for multi-pathway inhibition[3,4].

ADAM10 in particular acts as principal sheddase for Notch[5], Eph[6,7] and certain EGFR ligands[8] as well as E- and N-cadherin[9]. It's essential role for Notch function is highlighted by the resemblance of ADAM10[5] and Notch KO mice[4], with embryonic lethal defects in somitogenesis, neurogenesis and vasculogenesis[5]. Notch signalling is triggered by binding of cell-surface-bound ligands, Delta-Like(1-4) or Jagged(1, 2), to Notch receptors (Notch1-4), which initiates ADAM-mediated shedding of both ligand[10] and receptor extracellular domains (ECD)[11]. Shedding of the notch ECD provides the signal for γ-secretases to cleave and release the Notch intracellular domain (NICD), acting as transcriptional activator for an extensive set of genes[11], regulating cell proliferation, differentiation, EMT and cell survival. Deregulated Notch signalling promotes the progression of solid cancers[11], particularly by driving angiogenesis[11], while mutant activated Notch is a known cause in 50% of T-ALL. However, pan-specific γ-secretase inhibitors blocking NICD release[13] cause severe intestinal toxicity, likely reflecting the diversity of γ-secretase targets[15]. Similarly, small-molecule inhibitors blocking the ADAM protease active site failed clinical development due to lack of specificity and off-target effects, reflecting the close structural homology of this site in all MMPs[4,16].

ADAMs are transmembrane proteins with an N-terminal pro-domain followed by metalloprotease (M), disintegrin (D), cysteine-rich (C), transmembrane and cytoplasmic domains[3]. Intriguingly, their proteolytic specificity is not simply due to a typical substrate cleavage signature, but relies on non-catalytic interactions of the substrate with ADAM D+C domains that align the protease domain for effective cleavage[6,17,18]. In addition, emerging evidence suggests that adopting latent and active ECD conformations may regulate ADAM10 and 17 activities. This concept is based on the protein architecture revealed in crystal structures of the related snake venom metalloproteinases, adopting two different conformations that are stabilized by distinct disulphide connectivity of the D+C domains[19,20]: a closed conformation suggested to deny substrate access, and an open conformation that allows substrate access and promotes cleavage. ADAM10/17 ECDs indeed harbour a large number of disulfide bonds[21], including the conserved thioredoxin CxxC motif typical for disulfide exchange reactions catalysed by protein disulfide isomerases (PDIs)[22], and mild reducing or oxidising conditions and PDI treatment are known to alter ADAM17 activity[23,24]. Considering that reactive oxygen species (ROS) are frequently elevated in tumours due to RTK and pro-inflammatory signalling, and are known to activate ADAM10/17[23,25], an effect on protease domain orientation may explain the well-documented conundrum that kinase-dependent cytosolic signalling regulates the activity of the extracellular ADAM protease domain[3,26].

SUMMARY

The present invention is broadly directed to use of an antibody or antibody fragment, which preferentially recognizes and binds a proteolytically active form of an ADAM protease. More particularly, the inventors have discovered that expression of proteolytically active ADAM protease is relatively increased in tumour cells, most prominently in certain cells that also express the putative tumour stem cell marker CD133. This proteolytically active ADAM protease expressed by tumour cells is typically, although not exclusively, a high molecular weight form of an ADAM protease. Accordingly, the antibody or antibody fragment may be used to detect tumour cells and also as a therapeutic agent for treating cancers, tumours and other malignancies.

In an embodiment the ADAM protease is ADAM10 or ADAM 17 protease. In one particular embodiment, the ADAM protease is ADAM10 and the antibody or antibody fragment is monoclonal antibody 8C7. In a specific embodiment, the antibody or antibody fragment is a recombinant, humanized antibody or antibody fragment based on, or derived from 8C7.

In a first aspect, the invention provides an antibody or antibody fragment, or preferably a recombinant, humanized antibody or antibody fragment, that comprises: (i) an amino acid sequence set forth in SEQ ID NO:1, SEQ ID NO:2, SEQ ID NO:3 and/or SEQ ID NO:4, or an amino acid sequence at least 80% identical thereto; (ii) at least one complementarity determining region (CDR), or a portion thereof, having a CDR amino acid sequence set forth in SEQ ID NO:1, SEQ ID NO:2, SEQ ID NO:3 and/or SEQ ID NO:4; or (iii) at least one CDR, or a portion thereof, comprising an amino acid sequence at least 80% identical to a CDR amino acid sequence in SEQ ID NO:1, SEQ ID NO:2, SEQ ID NO:3 and/or SEQ ID NO:4.

Suitably, the recombinant, humanized antibody or antibody fragment comprises one or more additional amino acid sequences of a human immunoglobulin.

Preferably, the recombinant humanized antibody or antibody fragment specifically, selectively or preferentially binds a proteolytically active form of an ADAM10 protease.

This aspect also provides one or more isolated nucleic acids encoding the recombinant humanized antibody or antibody fragment of this aspect, a genetic construct comprising the one or more isolated nucleic acids and/or a host cell comprising the genetic construct.

In a second aspect, the invention provides a method of detecting a proteolytically active form of an ADAM protease, said method including the step of selectively binding an antibody or antibody fragment to the proteolytically active form of the ADAM protease to thereby detect the proteolytically active form of the ADAM protease.

In a third aspect, the invention provides a method of detecting a tumour cell, said method including the step of binding an antibody or antibody fragment which specifically, selectively or preferentially recognizes a proteolytically active form of an ADAM protease expressed by the tumour cell to thereby detect the tumour cell.

In a fourth aspect, the invention provides a kit for use according to the method of the first or second aspects, comprising an antibody or antibody fragment that specifically, selectively or preferentially binds a proteolytically active form of an ADAM protease.

The kit may further comprise one or more detection reagents.

In a fifth aspect, the invention provides a method of inhibiting an ADAM protease and/or one or more downstream signalling molecules in a cell, including the step of binding an antibody or antibody fragment which specifically, selectively or preferentially recognizes a proteolytically active form of the ADAM protease to the ADAM protease expressed by the cell, to thereby at least partly inhibit a biological activity of the ADAM protease and/or one or more downstream signalling molecules in the cell.

Preferably, the cell is a tumour cell.

Preferably, the biological activity of the ADAM protease is proteolytic activity.

In a sixth aspect, the invention provides a method of treating or preventing cancer in a mammal, said method including the step of administering to the mammal an antibody or antibody fragment which specifically, selectively or preferentially recognizes and binds a proteolytically active form of the ADAM protease to thereby treat cancer in the mammal.

Preferably, said mammal is a human.

In an embodiment of the aforementioned aspects, the antibody or antibody fragment binds a region or portion of an ADAM protease that provides a switch between a proteolytically active and inactive form of an ADAM protease. Suitably, the region or portion of ADAM protease is a loop which preferably comprises a disulphide bond between a cysteine residue and an adjacent CXXC motif. Suitably, in embodiments relating to ADAM 10 the loop comprises two intramolecular disulfide bonds: $C_{594}$-$C_{639}$ and $C_{632}$-$C_{645}$; the former being within the ADAM 10 protease sequence $C_{594}HVCC_{598}$ (SEQ ID NO:7).

In one particular embodiment, the loop protrudes away from the ADAM cysteine-rich domain that comprises substrate-binding residues, which in ADAM10 protease are $Glu_{573}$, $Glu_{578}$ and $Glu_{589}$.

In an embodiment, the antibody or antibody fragment binds or interacts with one or more ADAM10 protease residues selected from the group consisting of: $Arg_{557}$; Asp589; $Lys_{591}$; $Pro_{628}$; $Tyr_{638}$; $Cys_{639}$; $Asp_{640}$; $Val_{641}$; $Phe_{642}$; $Arg_{644}$, and $Arg_{646}$. Preferably, the binding or interaction includes hydrogen bonds formed between $Asp_{640}$, $Val_{641}$, $Phe_{642}$, $Arg_{644}$, and $Arg_{646}$ and the antibody or antibody fragment.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

FIGS. 1A-1E. Treatment with 8C7 mAb inhibits tumour growth. (FIGS. 1A, 1B) Mice bearing human LIM1215 CRC tumours were treated with 8C7 mAb at indicated doses or reagent control (2 injections/week). Tumour volumes were measured twice weekly using a calliper (FIG. 1A), the tumour mass of resected tumours was recorded at the end of the experiments (FIG. 1B). (FIG. 1C) Tissue sections of resected tumours were analysed with anti-CD31 antibodies to stain endothelial cells, revealing significantly-reduced microvascular density in 8C7-treated tumours. (FIG. 1D) Cell death in tumours was assessed using TUNEL IHC staining of tumours, suggesting increased apoptosis after 8C7 treatment, especially within the vascularised tumour rim. (FIG. 1E) Western blot analysis of detergent lysates from resected tumour shows downregulation of ADAM10 and a number of its substrates, including Eph and Notch receptors in 8C7-treated tumours. Lysates from individual tumours in each group are shown, the bar graph illustrates mean and SD of densitometry measurements.

(FIG. 2A) Confocal microscopy of tumours from mice injected with Alexa647-labelled 8C7. 8C7 binding (green pseudocolour) is strongest in the tumour rim and near tumour vessels (labelled with rhodamine lectin, red). Blue, Hoechst stained nuclei. (FIG. 2B) Co-staining of tumours from 8C7-injected mice with antibodies against the tumour stem cell marker CD133, or against cleaved (active) Notch1 or Notch2 intracellular domains (NICD1, 2) (red). Purple, lectin labeled vessels; Blue, Hoechst stained nuclei. (FIG. 2C) Western blot for active Notch (NICD1) of tumour cell isolates that had been sorted for CD133 expression (CD1330, + or −). (FIG. 2D) Flow cytometry of tumour cell isolates from Alexa647-8C7-injected mice, stained for 8C7+/CD133+ cells. CD133 is present on a small cell population (0.94%), which are strongly positive for 8C7-bound ADAM10.

(FIG. 3A) Protein extracts from LIM1215 tumours of 8C7-treated or control mice were analysed by Western blot with antibodies against NICD and the Notch target Hes1. Samples from individual tumours are shown. The diagram illustrates the mean and SD of the data quantitated by densitometry; *, p>0.05. (FIG. 3B) RNA extracts from PBS, 8C7 or 8E11 control mAb-treated LIM1215 tumours were analysed by real time PCR for expression of the Notch targets Hes1 and Hey1. Data from n=5 mice were analysed; *, p>0.05. (FIG. 3C) CD133+

LIM1215 cells isolated from tumours were treated in culture with 8C7, control mAb 8E11, or gamma-secretase inhibitor (GSI). Lysates were analysed by Western blot for active Notch (NICD). A representative Western blot from 3 separate experiments is shown. The diagram illustrates the mean and SD of the data quantitated by densitometry. # indicates IgG bands from treatment mAb.

Figure 4A:
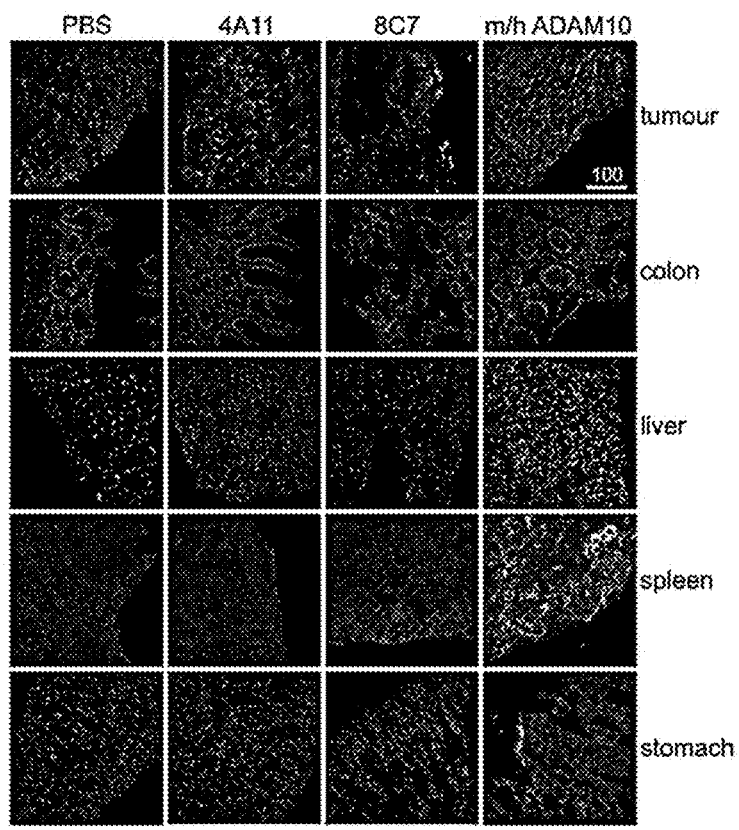
Figure 4B:
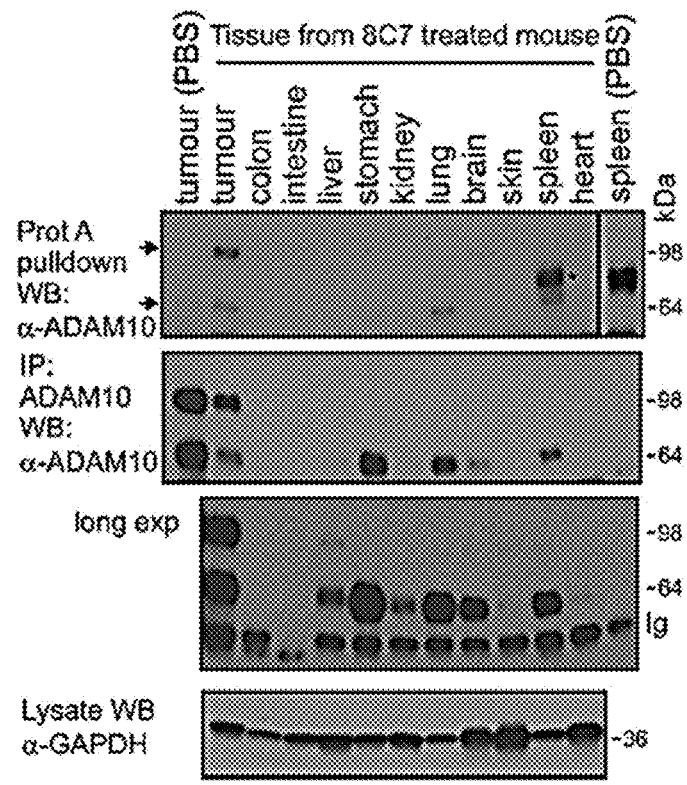

FIGS. 4A-4B. 8C7 preferentially recognises HMW ADAM10 present in tumours but not in normal mouse tissues. (FIG. 4A) Fluorescence microscopy of tissue sections from LIM1215 tumours and non-affected organs from mice injected with Alexa647-labelled anti-ADAM10 antibodies (green): 8C7 binds human and mouse ADAM10[27], 4A11 binds only human ADAM10, m/h ADAM10 is a commercial mouse/human ADAM10-specific control antibody. Blue, Hoechst stained nuclei. (FIG. 4B) Western blot analysis of 8C7-bound ADAM10 recovered from indicated tissues of 8C7-treated, tumour-bearing mice by Protein A Sepharose (top). Lower panels show the overall ADAM10 expression, assessed by IP from tissue lysates with control anti-ADAM antibody, indicating prevalence of HMW ADAM10 in tumours. The protein band indicated with * in the spleen sample also appears in the blot from the PBS-treated mouse and reflects non-specific reactivity of the blotting antibody.

Figure 5A:
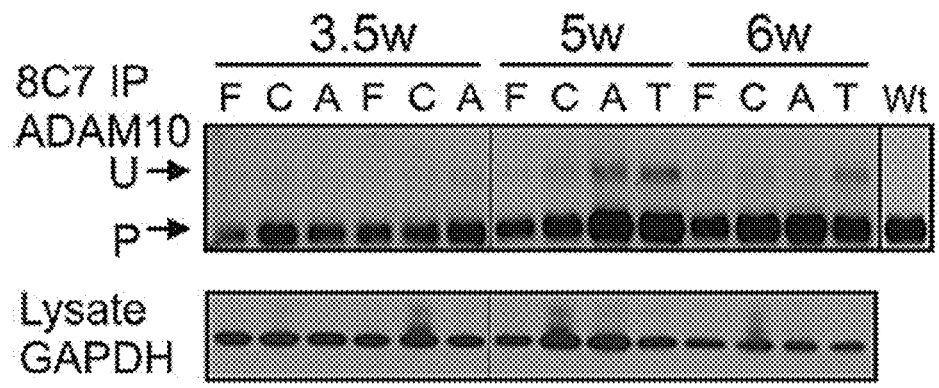
Figure 5B:
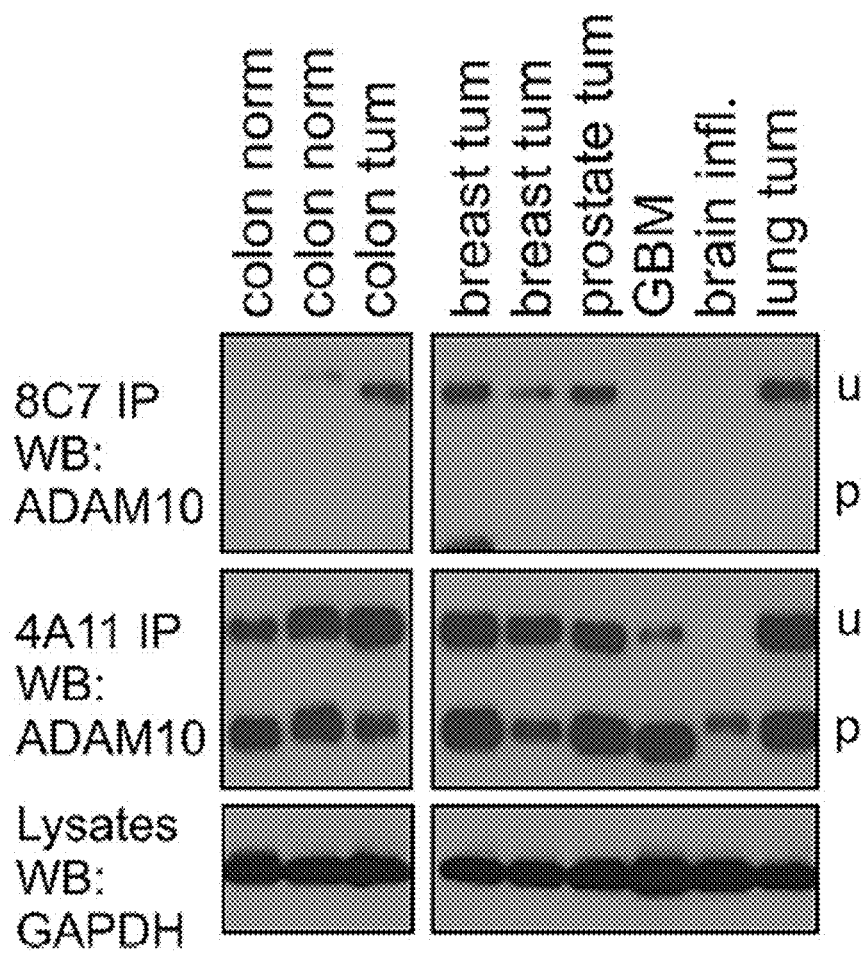

FIGS. 5A-5B. Recognition of the HMW form of ADAM10 by 8C7 is diagnostic for mouse and human tumours. (FIG. 5A) 8C7 Immunoprecipitates of ADAM10 from stomach tissues from GP130F knock-in mice developing spontaneous gastrointestinal tumours[38,39] at 5-6 weeks of age. Samples from different part of the stomach are shown, F=Fundus, C=Corpus, A=Antrum, T=tumour. (FIG. 5B) Immunoprecipitation of ADAM10 from (snap) frozen human tumour (tum) or normal (norm) tissues with 8C7 or control ADAM10 mAb 4A11 and Western blot analysis with anti-ADAM10 pAbs. 8C7 preferentially binds a subset of the non-processed high MW ADAM10 that is prevalent in tumours. U, unprocessed; P, processed ADAM10.

Figure 6A:
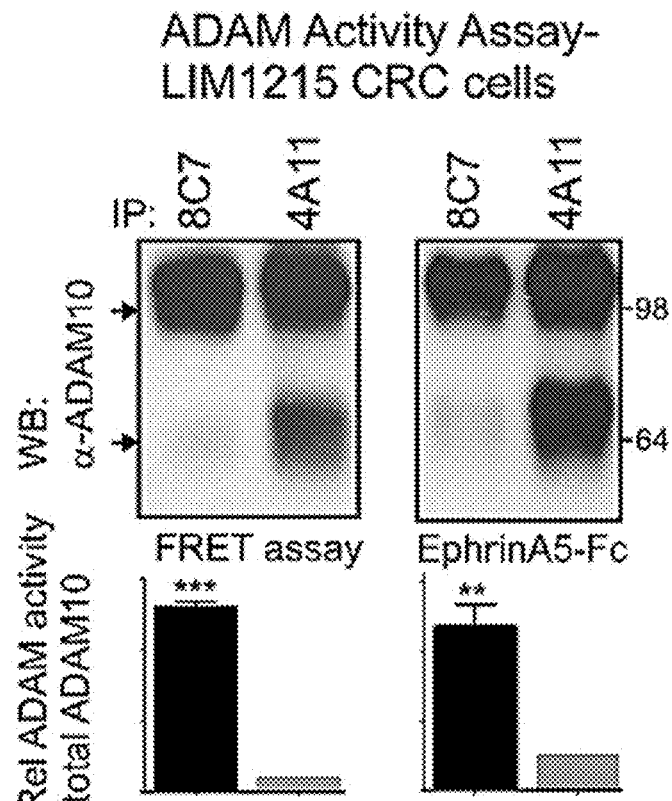
Figure 6B:
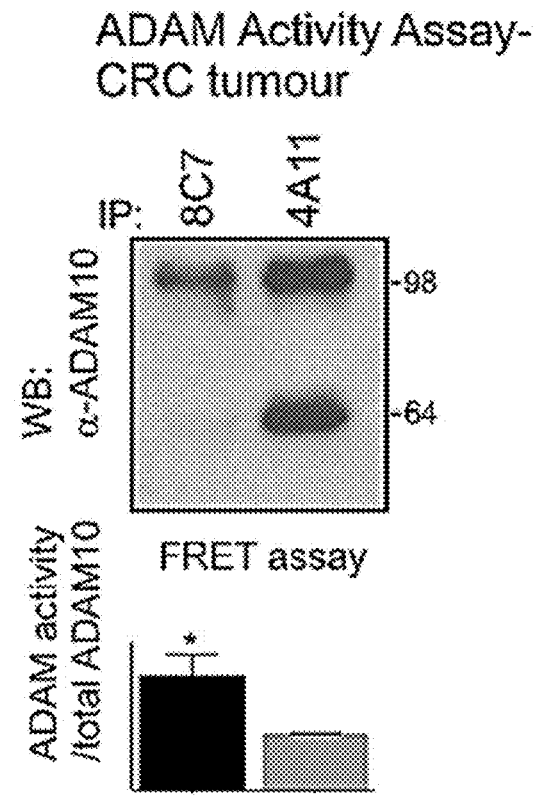

FIGS. 6A-6B. 8C7 binds to the enzymatically active form of ADAM10. Activity assays of ADAM10 IPs from LIM1215 cells (FIG. 6A) and human colorectal carcinoma (CRC) tumour tissue (FIG. 6B) shows that 8C7 selectively targets the HMW form of ADAM10. ADAM10 activity was measured with a fluorogenic peptide substrate (FRET assay, Es003, R&D Systems) or by cleavage of ephrin-A5 Fc as substrate. The protease activity relative to the protein level of ADAM10, as estimated from the Western blots of the IP is illustrated in the diagram. Mean and SEM of 3 independent assays are shown; unpaired t-test (two tailed) n=3; *p<0.0001, p<0.01, *p<0.05.

Figure 7A:
Figure 7B:
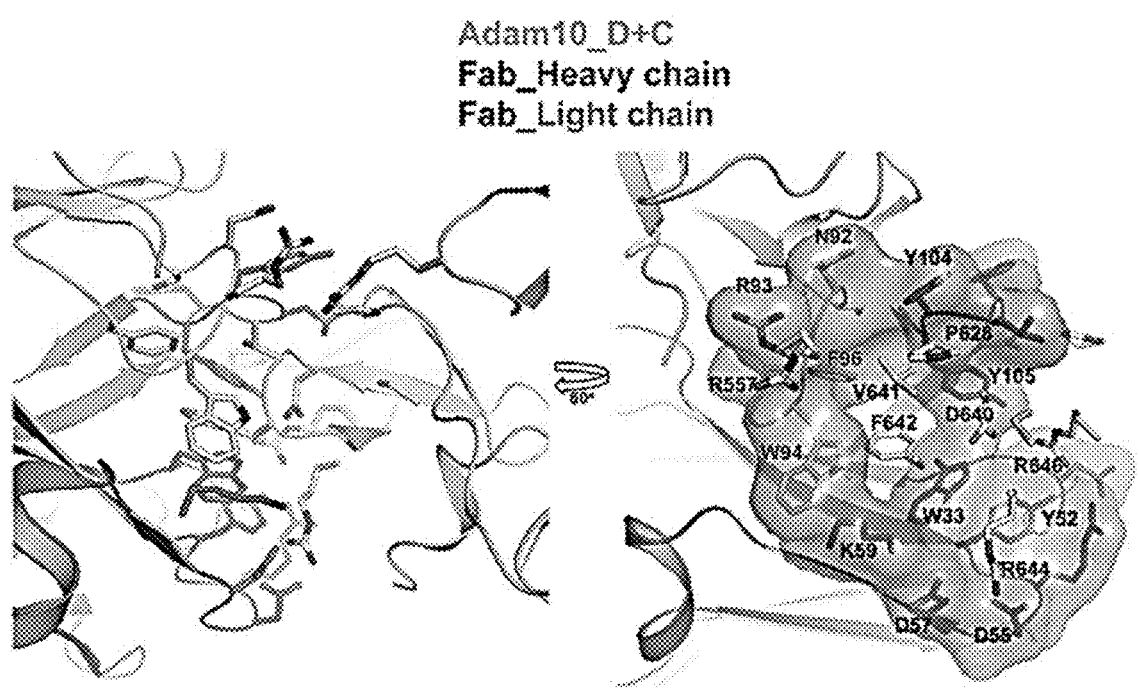

FIGS. 7A-7B. Protein X-ray crystal structure of the 8C7 F(ab')2 fragment binding the ADAM10 D+C domain. (FIG. 7A) Crystal Structure of the mAb-8C7/ADAM10 complex. The heavy chain of the 8C7 mAb is in magenta and the light—in cyan. The disintegrin and cysteine-rich domains of ADAM10 are in green. Disulphide bridges in ADAM10 are drawn as sticks and colored in yellow. Glycosylation moieties are drawn as grey spheres. A calcium, bound in the ADAM disintegrin domain, is in blue. (FIG. 7B) The 8C7 (magenta/cyan)/ADAM10 (green) interface with the ADAM CxxCC motif residues coloured in red. (FIG. 7B) Two close-up views of the 8C7/ADAM10 interface. The right panel view is a 60-degree rotation from the left panel view. The heavy chain of the 8C7 mAb is in magenta, the light—in cyan, and ADAM10 is in green. The interacting residues are drawn as sticks and labeled on the right panel. The molecular surface of 8C7, which is in contact with ADAM10, is rendered in grey on the right panel.

Figure 8A:
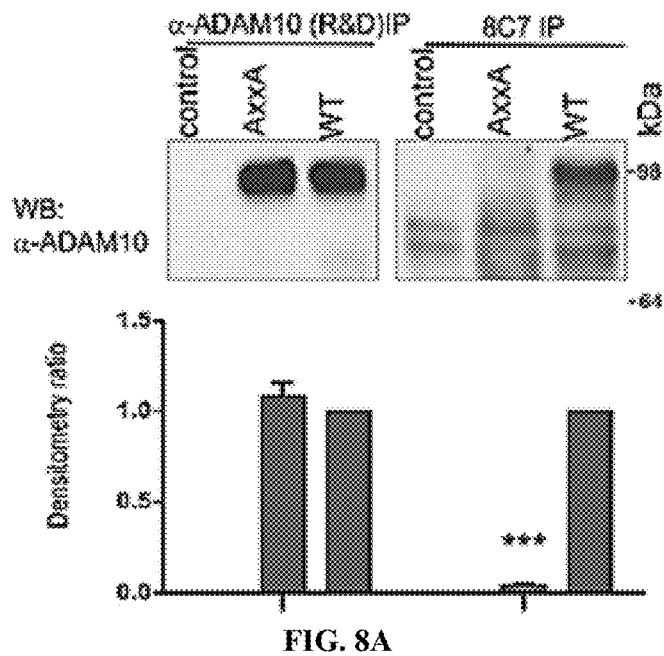
Figure 8B:
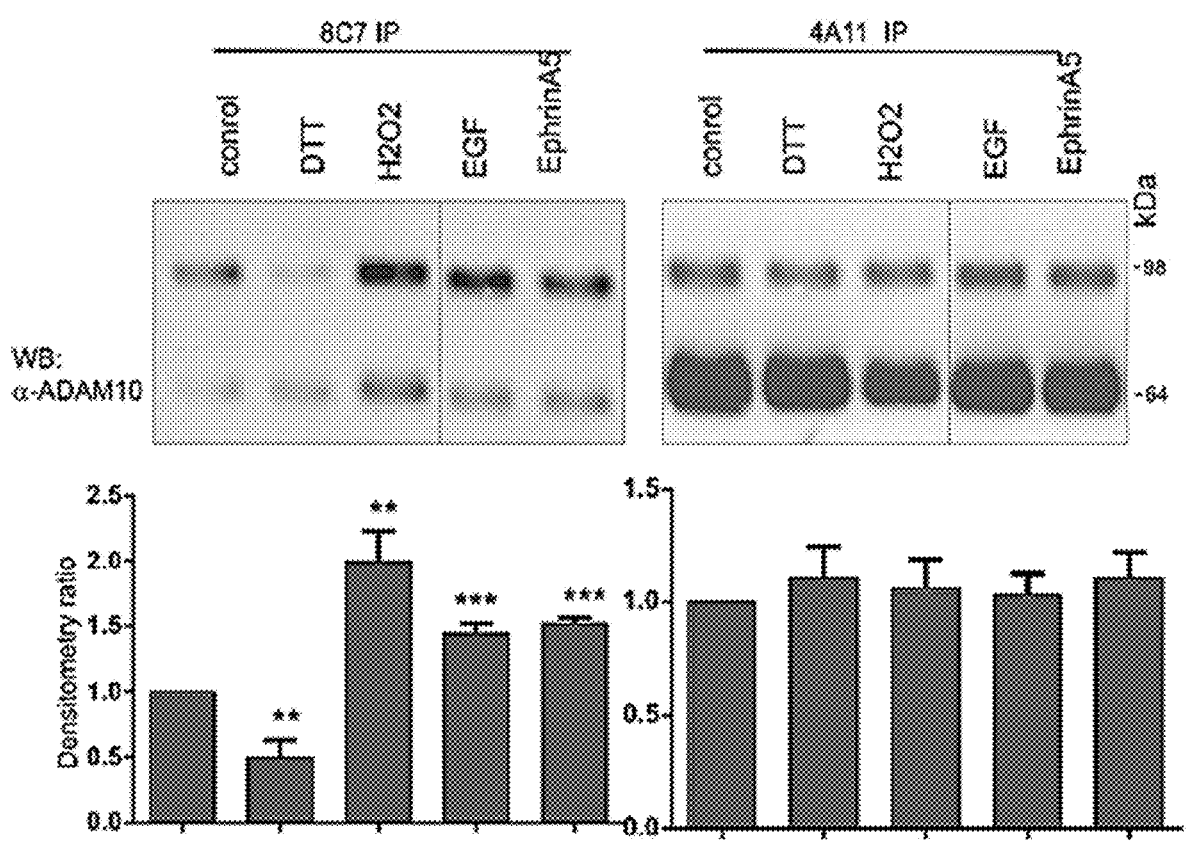

FIGS. 8A-8B. 8C7 binding relies on an intact ADAM10 CXXC motif and is increased by cell exposure to ROS or RTK agonists. (FIG. 8A) Mutation of ADAM10 CxxC motif blocks binding of 8C7 but not of control mAb. Detergent cell lysates from ADAM10-/- MEFS, transfected with Wt or AXXA mutant ADAM10, were IPed with control anti-ADAM10 mAb (R&D Biosystems) or with 8C7 as indicated. Western blots were probed with anti-ADAM10 pAb. Densitometry was used to quantitate binding of the mutant protein relative to Wt ADAM10. (FIG. 8B) 8C7 binding to ADAM10 was tested in cells treated with reductant (DTT), oxidant ($H_2O_2$) or RTK stimulation (known to generate localised ROS). Binding of 8C7, but not control mAb 4A11, is significantly increased under oxidative, conditions and decreased under reducing conditions. Results from 3 independent assays were quantitated by densitometry, mean+/− SEM are shown, significance estimated by unpaired t-test (two tailed) n=3; * p<0.0002,  p<0.005. ADAM10 levels in 4A11 IPs are not significantly different.

Figure 9A:
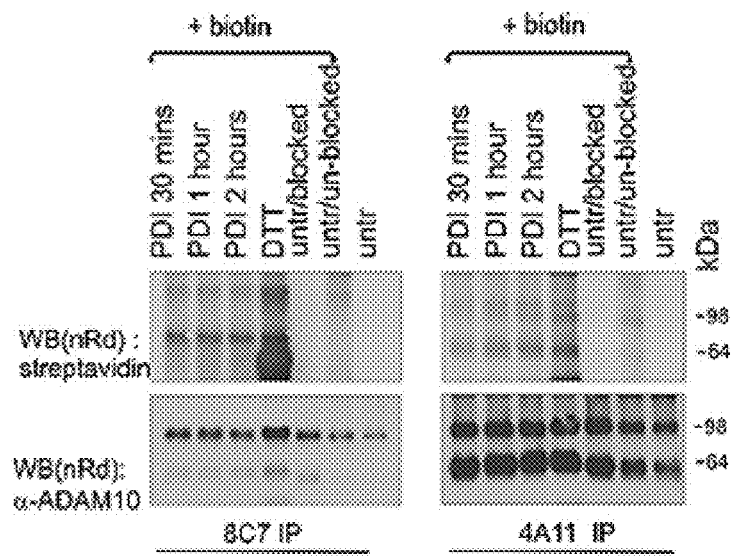
Figure 9B:
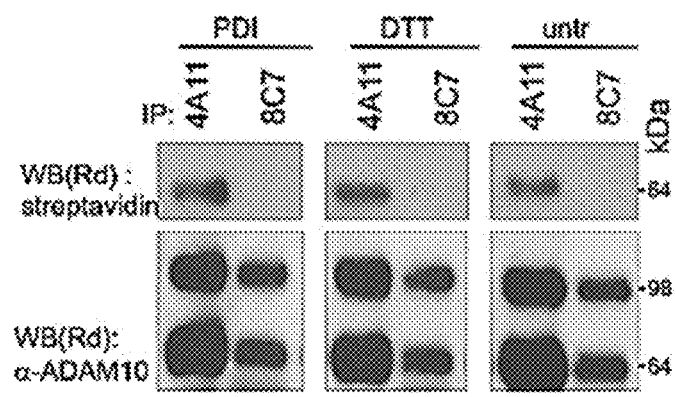
Figure 9C:
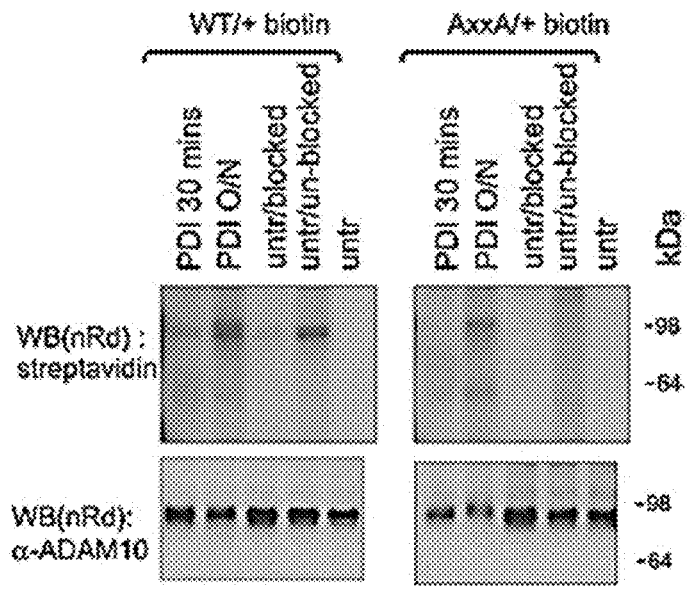

FIGS. 9A-9C. ADAM10 contains labile PDI-susceptible cysteines in the CxxC motif that are implicated in the 8C7-binding epitope. (FIG. 9A) 8C7 and 4A11 IPs from LIM1215 cell lysates, were treated with Methyl-PEG 12-maleimide (MPM) to block free cysteines, then with PDI (5 μg/ml) or DTT(20 μM) followed by Maleimide-PEG2-biotin to detect labile cysteines. Biotinlyation and total ADAM10 levels were detected by Western blot using streptavidin-HRP antibody and α-ADAM10 pAb, respectively. (FIG. 9B) 4A11 and 8C7 IPs from LIM1215 cells treated in culture with 2.5 mM MPM to block free cell-surface cysteines and with PDI/DTT to reduce labile disulfide bonds, followed by 2.5 mM MBP to detect reduced cysteines. 8C7 fails to bind cell surface ADAM10 that has been modified by MBP, whereas MBP labeling of ADAM10 in 4A11 IPs slightly increases with PDI/DTT treatment. (FIG. 9C) 4A11 IPs from lysates of ADAM10-/- MEFs transfected with Wt ADAM10 and AxxA ADAM10 cDNAs were treated with PDI/DTT as above, and Western blots were probed using Streptavidin-HRP and α-ADAM10 pAbs. While PDI treatment of Wt ADAM10 results in increased biotinylation over time, there is little biotinylation in mutant AxxA ADAM10, suggesting the CxxC motif is labile.

FIGS. 10A-10D. Treatment with 8C7 attenuates tumour growth and down modulates levels of its major substrates, but does not affect overall mouse weights. (FIG. 10A) Weights of control and 8C7-treated LIM1215 bearing mice were measured over the time of treatment. (FIG. 10B) Tumour volumes of LIM1215 tumour-bearing mice were treated with PBS, 8C7 mAb or control mAb 8E11 growth rates calculated over the treatment time. (FIG. 10C) Western blot analysis of tumour lysates shows down-regulation of Jagged (both full length and cleaved forms) and TGFα, in 8C7-treated tumours. (FIG. 10D) Western blot analysis of tumour lysates shows down-regulation EGFR, phosphor-EGFR and EphA2 in 8C7-treated tumours.

Figure 11A:
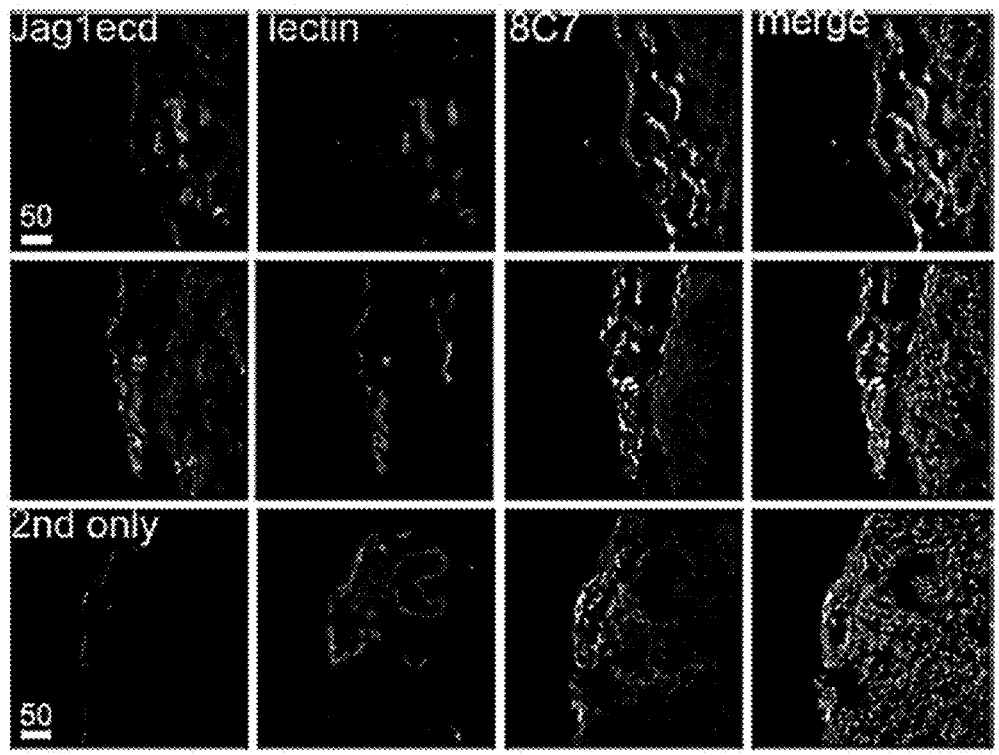
Figure 11B:
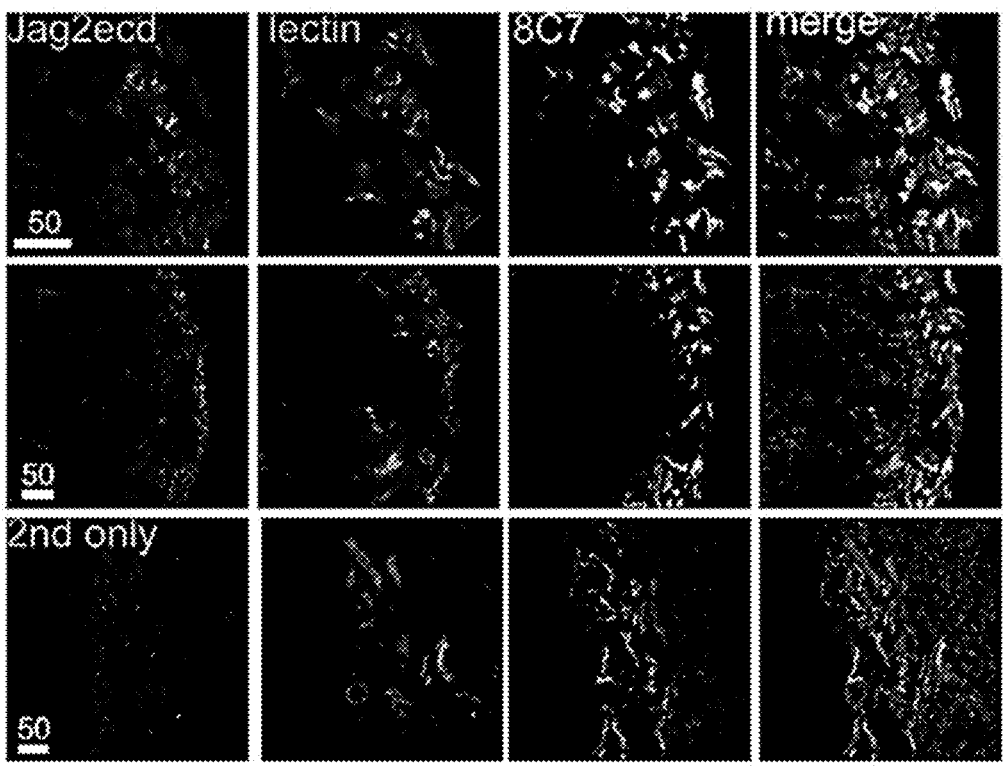

FIGS. 11A-11B: Tumour microvessels stain with antibodies against Jagged-1. Immunofluorescent confocal microscopy of tumors from mice injected with Alexa647-labelled 8C7 (cyan) and [Rhodamine]-RCA lectin (red). Sections were stained with antibodies against Jagged 1 (FIG. 11A), or 2 (FIG. 11B), (green). Blue, Hoechst stained nuclei.

Figure 12A:
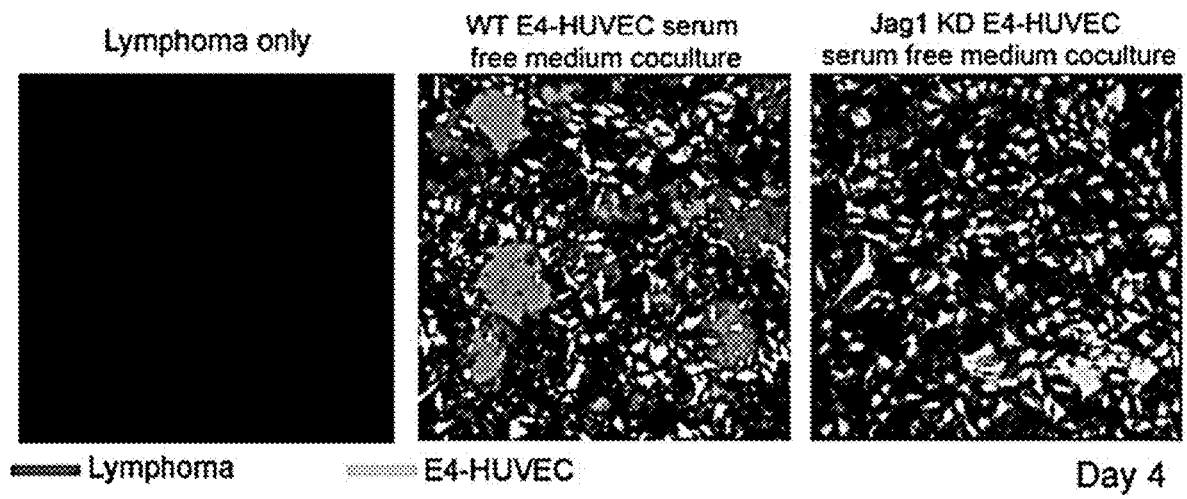
Figure 12B:
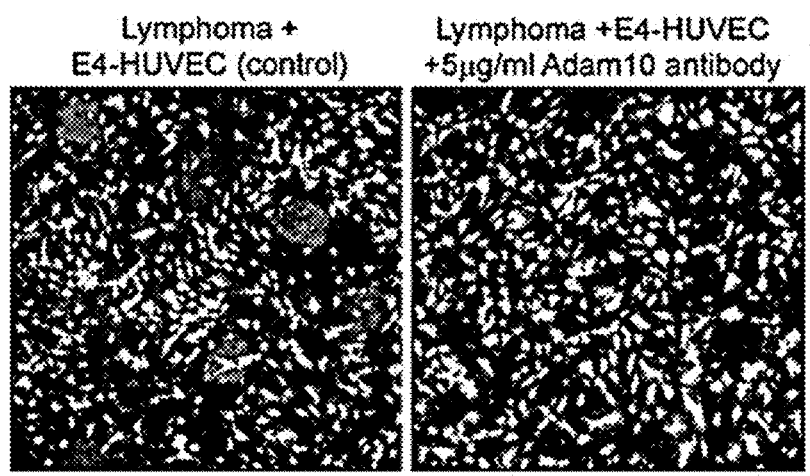
Figure 12C:
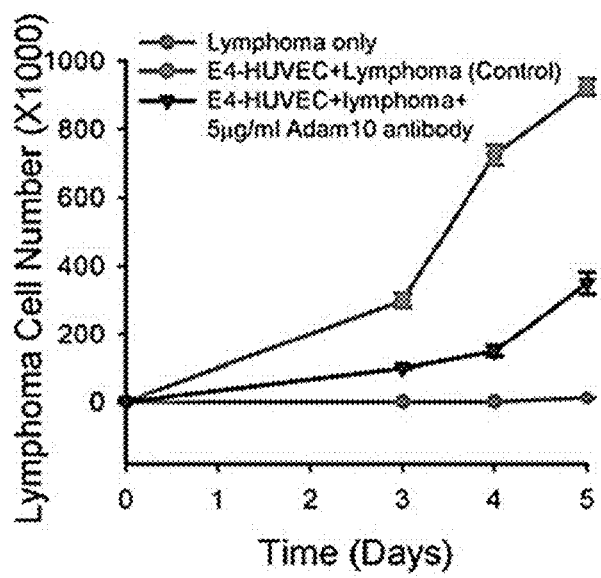

FIGS. 12A-12C: 8C7 inhibits Jagged/Notch dependent lymphoma proliferation. (FIG. 12A) Assay concept: lymphoma co-cultures with HUVECs, which had been transduced with the E4ORF1 gene auto-activating Akt (E4-HUVEC) to allow growth in serum- and cytokine-free culture: Lymphoma cells grow only with E4-HUVEC support; Jag1 knockdown (KD) in E4-HUVECs abolishes lymphoma propagation. (FIGS. 12B, 12C) mAb8C7 treatment inhibits the Jag1-dependent endothelial support of lymphoma proliferation.

FIGS. 13A-13B: The HMW form of ADAM10 is processed by Furin in-vitro and is present on the cell surface. (FIG. 13A) 8C7 and 4A11 IPs from LIM1215 lysates were treated with recombinant furin and reduced (Rd) samples analysed by Western blot with α-ADAM10 pAb and an ADAM10 pro-domain-specific antibody. Furin dose dependently cleaves the ADAM10 HMW (98 kDa) band of both 8C7 and 4A11 IPs to release the prodomain and increase 64 kDa ADAM10 levels. Detection of ADAM10-prodomain increases dose dependently (lower panels). The prodomain is more abundantly generated in 8C7 IPs despite of higher ADAM10 loading in 4A11 IPs. (FIG. 13B) Lysates from LIM1215 cells, incubated for 3 hours with 8C7 or 4A11 at 37° C. or under indicated conditions preventing endocytosis. Protein-A beads were added to the cell lysates to pull down cell surface bound ADAM10. Western Blots were probed with α-ADAM10 pAB.

FIG. 14: Processing by Furin does not affect ADAM10 activity. 8C7 IPs from whole cell LIM1215 lysates were left untreated (control) or treated with recombinant Furin for 1 h, or 5 h, as indicated, before assaying for ADAM10 sheddase activity. The activity (graph) was determined using the FRET assay with a fluorogenic peptide substrate (FRET assay, Es003, R&D Systems), expressed relative to the ADAM10 protein level determined by Western blot analysis under non-reducing (nRd) and reducing (Rd) conditions (as indicated). Despite complete conversion of the HMW form into the LMW form the ADAM10 activity remained unchanged compared to the control sample.

Figure 15:
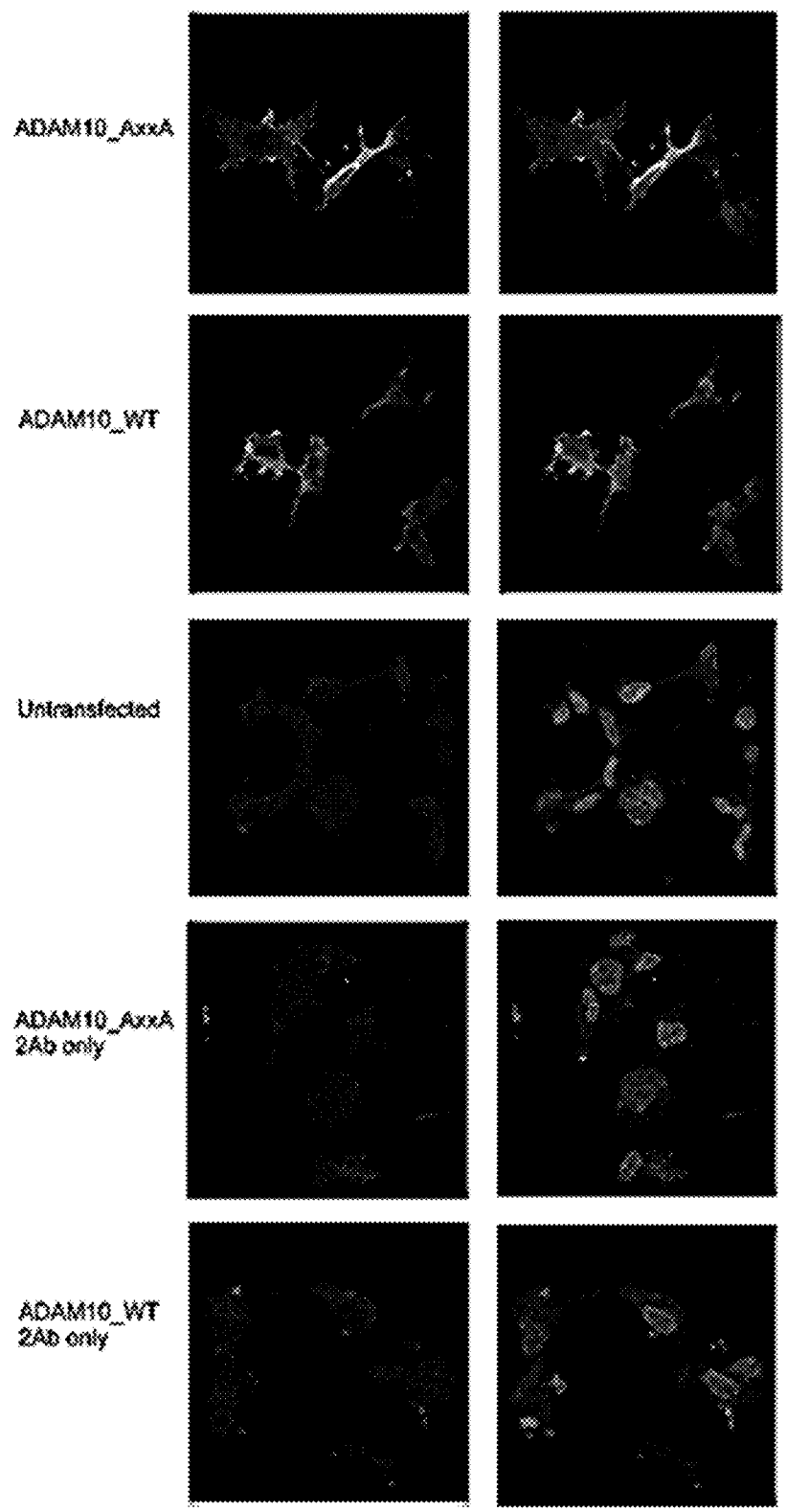

FIG. 15. The CxxC-to-AxxA mutation does not affect ADAM10 localisation ADAM10/wt and ADAM10/AxxA cDNA was transfected into MEF ADAM10−/− cells. Fixed and permeabilized cells were stained with primary Ab α-ADAM10 (R&D) and secondary antibody α-mouse-647. Wt and AxxA mutant ADAM10 display similar localization including both intracellular and cell surface staining.

Figure 16:
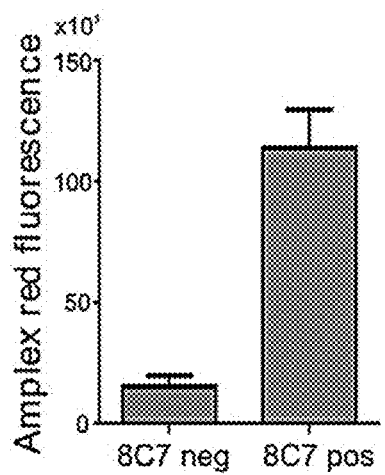

FIG. 16. 8C7-targeted tumour cells exhibit high levels of reactive oxygen species (ROS). Tumour cells from LIM1215 xenograft-bearing mice, injected with Alexa-labelled 8C7, were recovered and sorted for 8C7 positive or negative staining. Equal numbers of these cells were then compared for levels of ROS production using the Amplex red assay (Invitrogen).

Figure 17A:
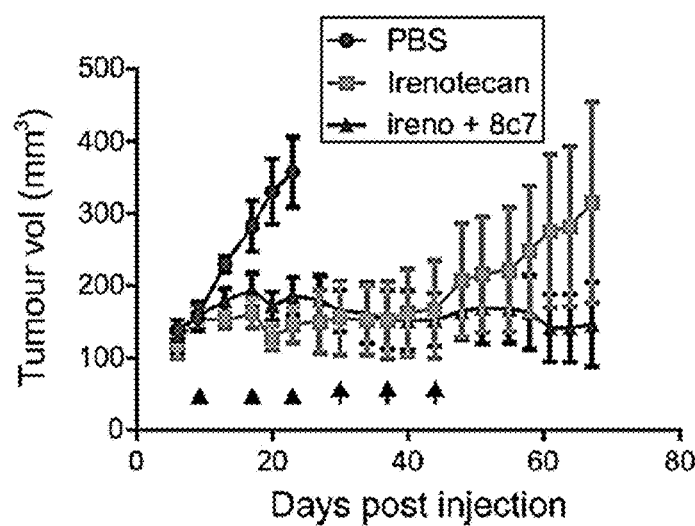
Figure 17B:
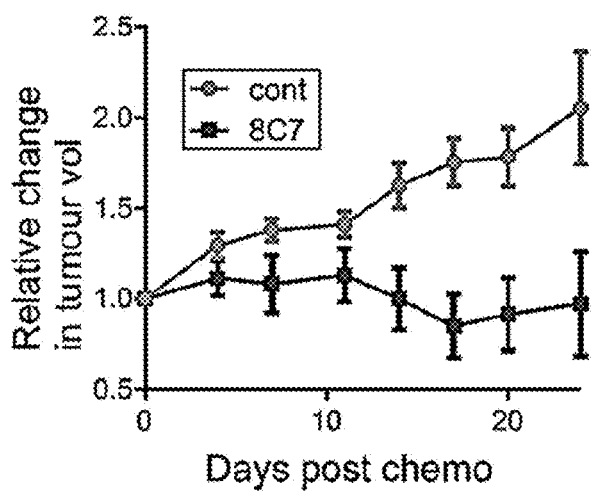
Figure 17C:
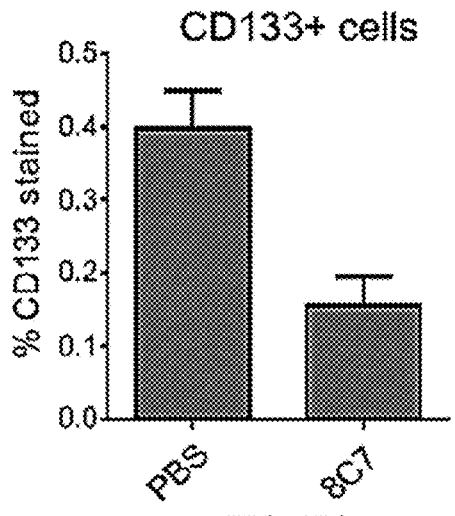

FIGS. 17A-17C. 8C7 blocks tumour regrowth following chemotherapy. LIM1215 xenograft-bearing mice were treated with increasing doses of the chemotherapeutic irenotecan (once/week for 6 weeks, arrows), with or without 8C7 (twice weekly). (FIG. 17A) Tumour volumes compared to control (PBS treated) mice. (FIG. 17B) Change in tumour volume following last dose of chemotherapy. (FIG. 17C) % of CD133+ cells in tumours recovered at end of experiment and analysed by flow cytometry.

Figure 18:
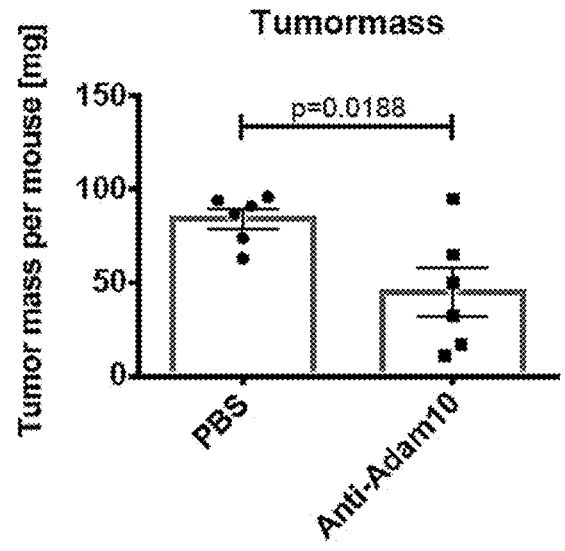

FIG. 18. 8C7 blocks spontaneous tumour growth in GP130F mice. Mice were treated with 8C7 or PBS from week 4 to 9 (2×/week), following which tumours were recovered and weighed.

Figure 19A:
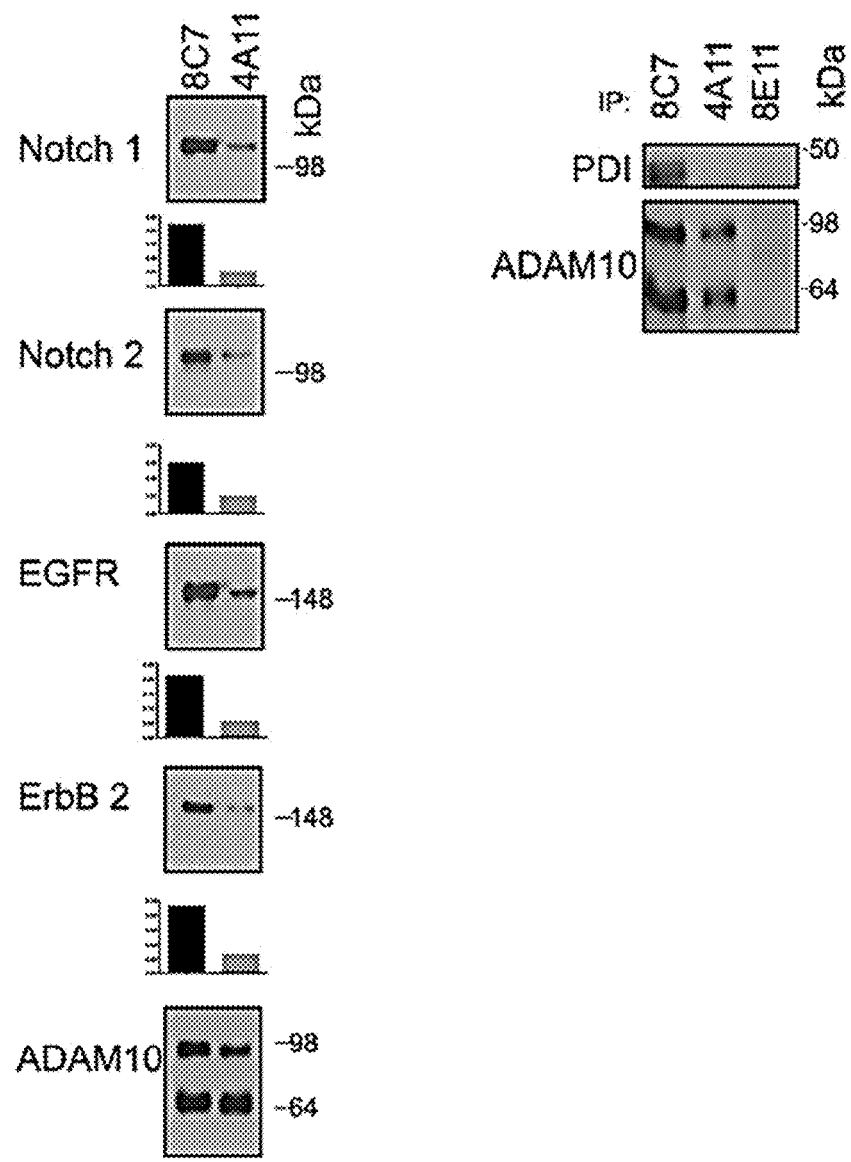

FIG. 19A. 8C7-bound ADAM10 preferentially associates with notch and erbB receptors, and PDI. Associations are shown by co-immunoprecipitation and Western blots. Graphs show relative binding from densitometry analysis.

Figure 19B:
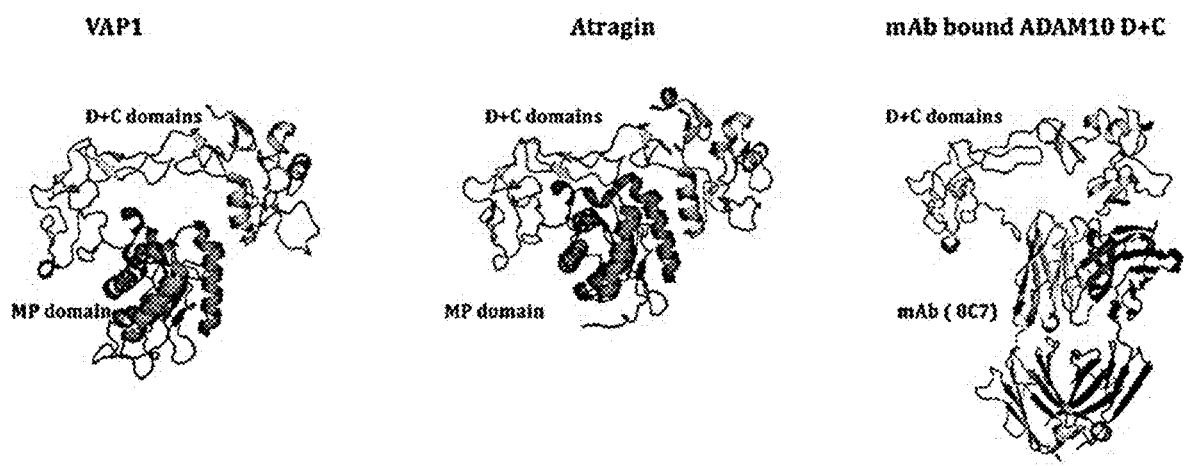

FIG. 19B. Comparison of 8C7/ADAM10D+C and snake venom metalloproteinases. 8C7/ADAM10D+C structure (right) with structures of full length snake venom metalloproteases (predicted to have similar overall structure). 8C7 binds in the region where the MP domain resides in the other structures.

Figure 20:
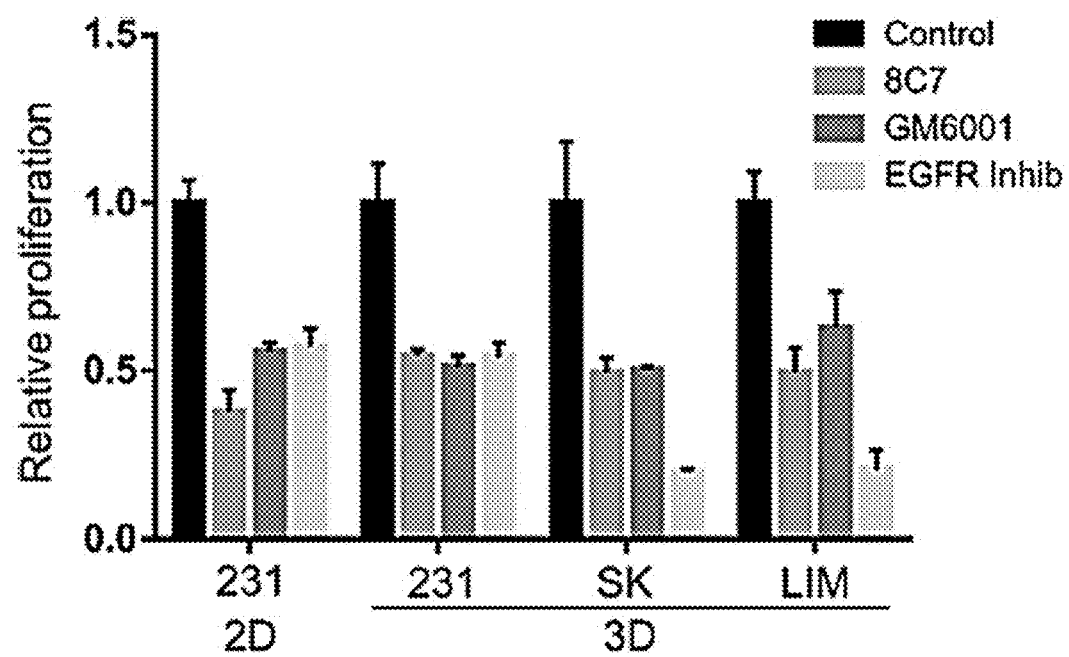

FIG. 20. Alamar blue growth assays on breast cancer cell lines. Breast cancer cell lines were treated with 8C7, metalloprotease inhibitor (GM6001) or EGFR kinase inhibitor (AG1478); on plastic (2D) or matrigel (3D). Time point day 4.

Figure 21:
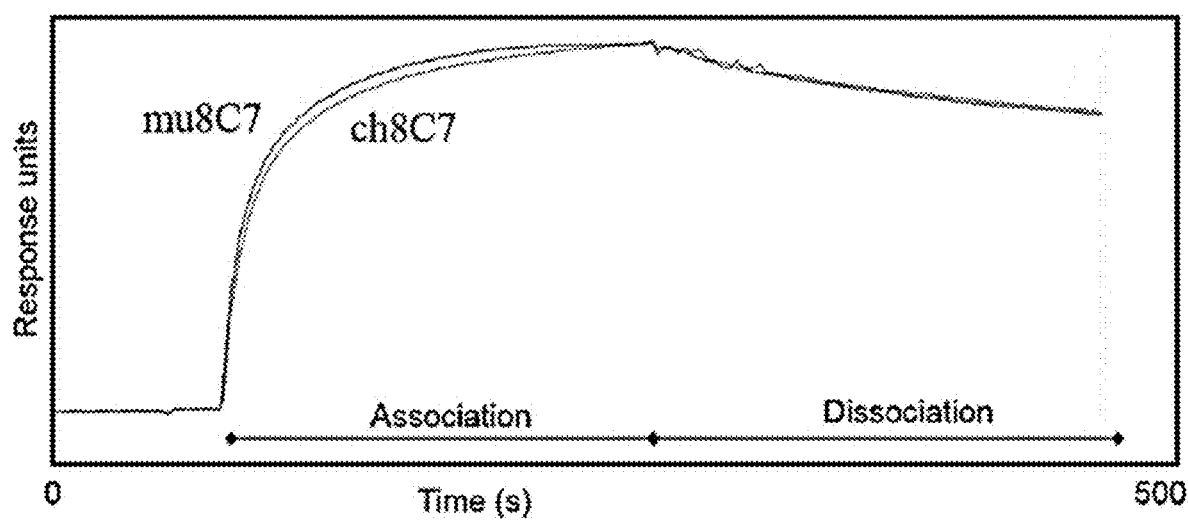

FIG. 21. Comparison of mu8C7 and ch8C7 binding to immobilised recombinant huADAM10D+C protein. Traces represent the binding and dissociation of antibodies in solution to immobilised huADAM10D+C protein, as measured on a BIAcore 3000 biosensor.

Figure 22:
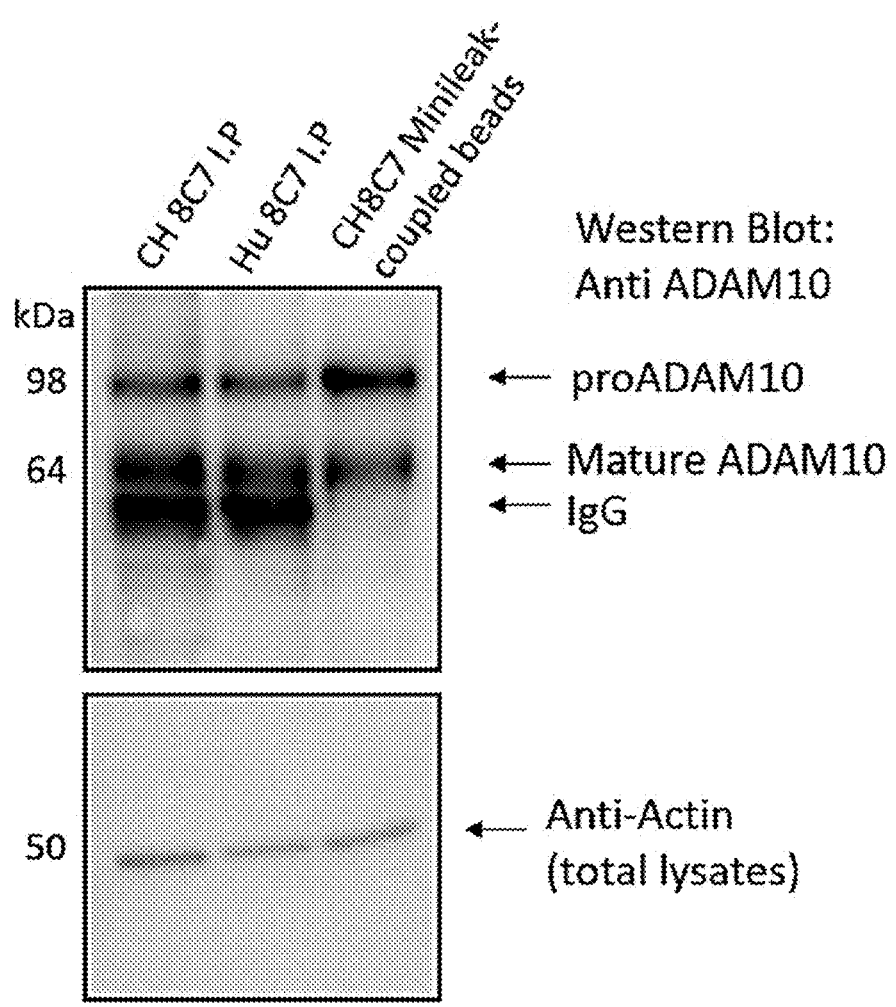

FIG. 22. Binding of ch8C7 and hu8C7 to endogenous ADAM10 in lysates of LIM1215 cells. Identical cell lysates were incubated with 5 μg/ml ch or hu 8C7 and protein A sepharose beads (lanes 1 and 2), or ch8C7 coupled to minileak beads as a positive control (lane 3). Beads were recovered and bound protein analysed by Western blot with anti-ADAM10 antibody (Abcam pAb 39177). The two top bands represent pro (unprocessed) and mature (processed) ADAM10, and the lowest band is cross-reactivity with the IgG heavy chain (as shown by absence in lane 3 using beads coupled to ch8C7). The lower panel shows lysates blotted for Actin as a loading control.

Figure 23:
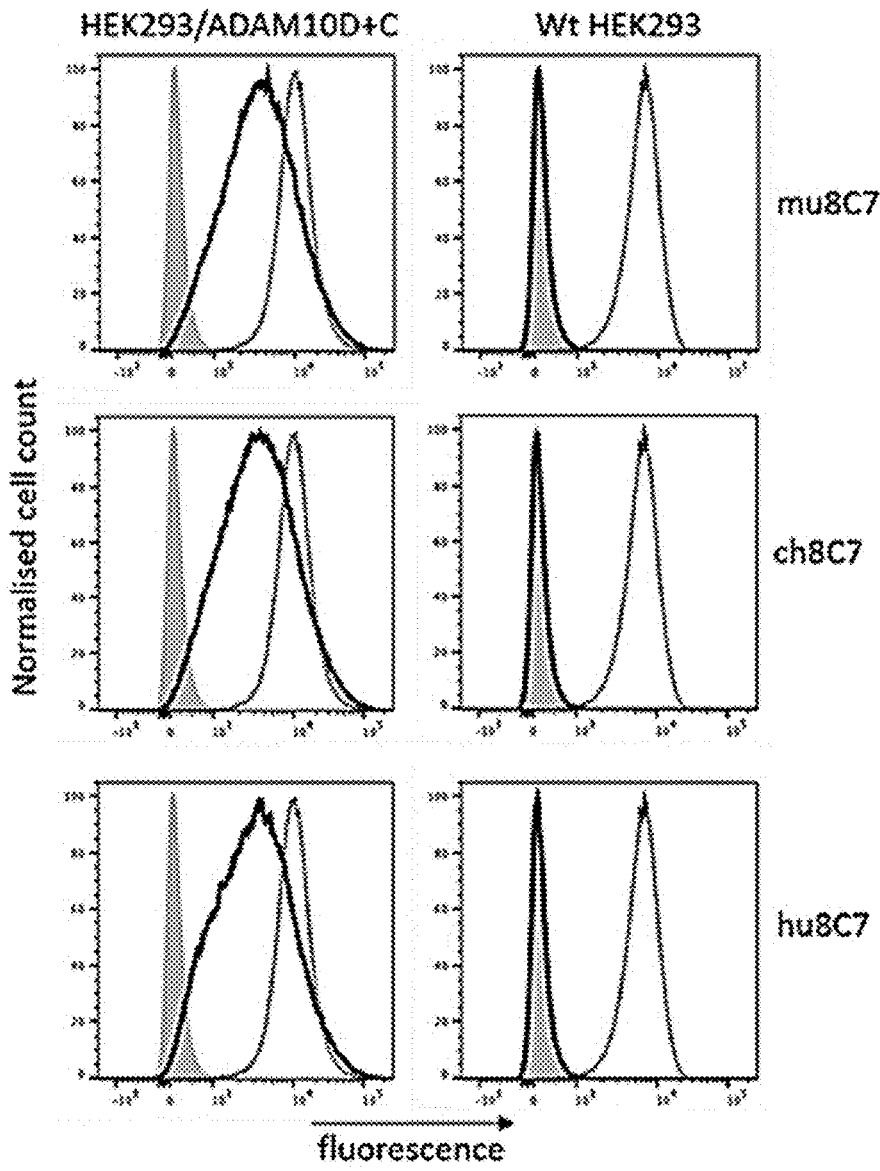

FIG. 23. Binding of anti-ADAM10 antibodies to cells expressing membrane-targeted ADAM10D+C. HEK293 cells expressing endogenous ADAM10 (Wt HEK293), or also expressing membrane targeted huADAM10D+C domains, were stained with 10 μg/ml of murine (mu), chimeric (ch) or humanized (hu) 8C7 as indicated, followed by Alexa-647-labelled secondary antibodies, and analysed by flow cytometry. Histograms show relative binding (fluorescence) of 8C7 variants (black, unbroken line), versus an anti-ADAM10 positive control antibody (dotted line) and an isotype-matched negative control IgG (grey, filled).

Figure 24A:
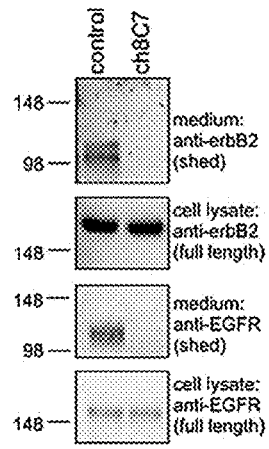
Figure 24B:
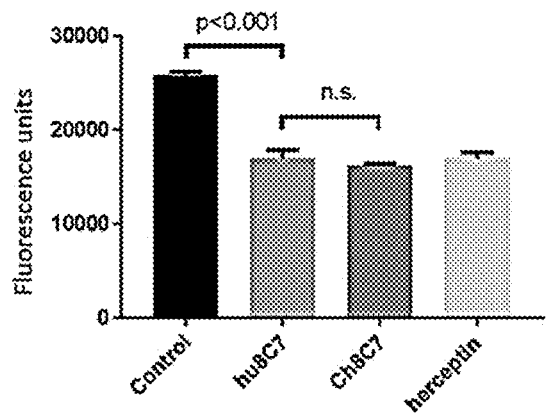

FIGS. 24A-24B. 8C7 inhibits erbB receptor shedding and growth/viability of breast cancer cells. (FIG. 24A) We tested if 8C7 inhibits erbB receptor shedding using erbB2-amplified SKBR3 and EGFR-high A431 cells, treated with 100 μg/ml ch8C7 or vehicle control. Receptors were immuno-precipitated from conditioned medium using extracellular domain antibodies (Cell Signalling) and from cell lysates as control, and Western blotted (as indicated). Levels of shed receptors, evident as lower MW bands (compared to in cell lysates) were markedly lower in 8C7 treated cultures. (FIG. 24B) BT474 cells were cultured in low binding tissue culture plates for 4 days with 100 μg/ml of the indicated antibodies, or vehicle control, and assayed for proliferation/viability using Alamar blue fluorescence. (n.s. not significant).

FIG. 25. Amino acid sequence comparison of murine 8C7 variable regions with corresponding human variable regions. Murine 8C7 heavy chain variable region (SEQ ID NO:1) is aligned with human heavy chain variable region (SEQ ID NO:3) and murine 8C7 light chain variable region (SEQ ID NO:2) is aligned with human light chain variable region (SEQ ID NO:4). CDR regions are bolded and amino acid sequence differences between the murine and human sequences are underlined. The amino acid sequences of the CDR regions are set forth in SEQ ID NOs: 13-18.

FIG. 26. Nucleotide sequences encoding human variable regions. SEQ ID NO:5 encodes SEQ ID NO:3 and SEQ ID NO:6 encodes SEQ ID NO:4.

FIGS. 27A-27B. ch8C7 and hu8C7 Human Kappa and IgG1 constant region amino acid and nucleotide sequences. Light chain amino acid sequence=SEQ ID NO:7 (FIG. 27A); Heavy chain amino acid sequence=SEQ ID NO:8 (FIG. 27B); Light chain nucleotide sequence=SEQ ID NO:9 (FIG. 27A); Heavy chain nucleotide sequence=SEQ ID NO:10 (FIG. 27B).

DETAILED DESCRIPTION

ADAM10 is a transmembrane metalloprotease frequently overexpressed in many tumours where it acts by releasing a range of cell surface proteins that promote tumour progression. By shedding ligands and receptors of the Notch, Eph, EGF, GP130/IL6 and chemokine families, ADAM10 activates key cancer signalling pathways and drug resistance mechanisms, but lack of active site inhibitors with sufficient specificity has hindered its clinical development to date. The ADAM10 protease comprises disintegrin and cysteine-rich domains having a substrate-binding pocket within the C domain that specifies ligand cleavage. The 8C7 monoclonal antibody specifically recognises the substrate binding domain and inhibits ADAM10-mediated cleavage of Eph receptor ligands (ephrins) and ephrin/Eph-dependent signalling and cell segregation in vitro. Analysis of the structure of 8C7 in complex with ADAM10 revealed binding to a critical cysteine-rich sequence motif that regulates ADAM10 function. 8C7 treatment inhibits growth of human colon tumour xenografts due to inhibition of Notch signalling and down-regulation of Notch, EGFR and Eph receptor levels. 8C7 specifically targets tumour cells, preferentially binding to cells that express the putative tumour stem cell marker CD133 and that display active Notch-signalling within tumours. More particularly, 8C7 selectively binds a proteolytically active form of ADAM10, which is diagnostic in mouse tumour models and in several human solid tumours. Accordingly, certain embodiments of the invention relate to 8C7 as an antibody suitable for human cancer therapeutic and diagnostic uses. It is also proposed that the disclosure provided herein may also be applicable to related ADAM proteases such as ADAM17.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

By "protein" is meant an amino acid polymer. The amino acids may be natural or non-natural amino acids, D- or L-amino acids as are well understood in the art.

A "peptide" is a protein having no more than fifty (50) amino acids.

A "polypeptide" is a protein having more than fifty (50) amino acids.

As used herein, the abbreviation "ADAM" relates to a family of transmembrane metalloproteases that catalyse the release of a range of cell surface proteins, activating receptor tyrosine kinase (RTK), Notch, cytokine-, chemokine- and adhesion signalling pathways important in normal and oncogenic development. Prominent oncogenic substrates include ligands and receptors in the Notch, erbB and Eph families, cytokines (TNFα, IL6), FASL, Slit, L-selectin and cadherins. The amino acid residue numbering system used herein is based on ADAM sequences available under Genbank accession numbers: NM_001110 (human ADAM10; SEQ ID NO:12), NM_174496 (mouse ADAM 10), NM_007399 (bovine ADAM10), NM 003183 (human ADAM17) and NM_009615 (mouse ADAM17).

As used herein an "antibody" is or comprises an immunoglobulin. The term "immunoglobulin" includes any antigen-binding protein product of a mammalian immunoglobulin gene complex, including immunoglobulin isotypes IgA, IgD, IgM, IgG and IgE and antigen-binding fragments thereof. Included in the term "immunoglobulin" are immunoglobulins that are chimeric or humanised or otherwise comprise altered or variant amino acid residues, sequences and/or glycosylation, whether naturally occurring or produced by human intervention (e.g. by recombinant DNA technology).

Antibody fragments include Fab and Fab'2 fragments, diabodies and single chain antibody fragments (e.g. scVs), although without limitation thereto. Typically, an antibody comprises respective light chain and heavy chain variable regions that each comprise CDR 1, 2 and 3 amino acid sequences The antibody or antibody fragment may comprise at least a portion of a CDR1, 2 and/or 3 amino acid sequence A preferred antibody fragment comprises at least one entire light chain variable region CDR and/or at least one entire heavy chain variable region CDR.

Antibodies and antibody fragments may be polyclonal or preferably monoclonal. Monoclonal antibodies may be produced using the standard method as for example, described in an article by Köhler & Milstein, 1975, Nature 256, 495, or by more recent modifications thereof as for example described in Chapter 2 of Coligan et al., CURRENT PROTOCOLS IN IMMUNOLOGY, by immortalizing spleen or other antibody producing cells derived from a production species which has been inoculated with an ADAM protease or fragment thereof. It will also be appreciated that antibodies may be produced as recombinant synthetic antibodies or antibody fragments by expressing a nucleic acid encoding the antibody or antibody fragment in an appropriate host cell. Recombinant synthetic antibody or antibody fragment heavy and light chains may be co-expressed from different expression vectors in the same host cell or expressed as a single chain antibody in a host cell. Non-limiting examples of recombinant antibody expression and selection techniques are provided in Chapter 17 of Coligan et al., CURRENT PROTOCOLS IN IMMUNOLOGY and Zuberbuhler et al., 2009, Protein Engineering, Design & Selection 22 169.

Antibodies and antibody fragments may be modified so as to be administrable to one species having being produced in, or originating from, another species without eliciting a deleterious immune response to the "foreign" antibody. In the context of humans, this is "humanization" of the antibody produced in, or originating from, another species. Such methods are well known in the art and generally involve recombinant "grafting" of non-human antibody complementarity determining regions (CDRs) onto a human antibody scaffold or backbone. Particular embodiments of recombinant, humanized antibodies will be described in more detail hereinafter.

In some embodiments, the antibody or antibody fragment is labeled.

The label may be selected from a group including a chromogen, a catalyst, biotin, digoxigenin, an enzyme, a fluorophore, a chemiluminescent molecule, a radioisotope, a drug or other chemotherapeutic agent, a magnetic bead and/or a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

The fluorophore may be, for example, fluorescein isothiocyanate (FITC), Alexa dyes, tetramethylrhodamine isothiocyanate (TRITL), allophycocyanin (APC), Texas Red, Cy5, Cy3, or R-Phycoerythrin (RPE) as are well known in the art.

The enzyme may be horseradish peroxidase (HRP), alkaline phosphatase (AP), β-galactosidase or glucose oxidase, although without limitation thereto.

Suitably, the antibody or antibody fragment specifically, selectively or preferentially binds or interacts with a proteolytically active form of a human ADAM protease. Accordingly, the antibody or antibody fragment may be capable of distunguishing or discriminating between a proteolytically active form of an ADAM protease and a proteolytically inactive form of an ADAM protease.

One embodiment of an antibody or antibody fragment disclosed herein is mAb 8C7 which is a monoclonal antibody which specifically, selectively or preferentially binds or interacts with a proteolytically active form of a human ADAM10 protease. By this is meant that 8C7 monoclonal antibody binds to, or interacts with, a proteolytically active form of an ADAM10 mprotease but does not bind to or interact with, or binds to or interacts with substantially less affinity, a proteolytically inactive form of an ADAM10 protease. Accordingly, the 8C7 monoclonal antibody may be capable of distinguishing or discriminating between a proteolytically active form of an ADAM10 protease and a proteolytically inactive form of an ADAM10 protease. In one form, the proteolytically active form of the ADAM protease may be characterized by the presence of a disulfide bond between: (i) a cysteine residue present in a loop that protrudes away from the ADAM10 cysteine-rich domain, which in ADAM10 comprises substrate-binding residues $Glu_{573}$, $Glu_{578}$, $Glu_{589}$; and (ii) another cysteine in the amino acid sequence CXXC, such as $C_{594}$ in the ADAM10 sequence $C_{594}HVCC_{598}$ (SEQ ID NO:11). The loop may comprise two intramolecular disulfide bonds: such as $C_{594}$-$C_{639}$ and $C_{632}$-$C_{645}$ in ADAM10.

In further embodiments, the antibody or antibody fragment may be characterized as binding or interacting with one or more human ADAM10 residues selected from the group consisting of: $Arg_{557}$; $Asp589$; $Lys_{591}$; $Pro_{628}$; $Tyr_{638}$; $Cys_{639}$; $Asp_{640}$; $Val_{641}$; $Phe_{642}$; $Arg_{644}$, and $Arg_{646}$, or the corresponding residues in other non-human mammalian ADAM proteases. Preferably, the binding or interaction includes hydrogen bonds formed between Asp640, $Val_{641}$, $Phe_{642}$, $Arg_{644}$, and $Arg_{646}$ of ADAM10 protease or the corresponding residues in other, non-human mammalian forms of ADAM proteases, and the antibody or antibody fragment.

Therefore, an antibody or antibody fragment useful according to the invention may broadly be defined as an antibody or antibody fragment characterized as having substantially the same or similar activity as 8C7 mAb in a mammal, with regard to specifically, preferentially or selectively binding to, or interacting with, a proteolytically active form of an ADAM10 protease.

The 8C7 mAb comprises heavy and light chain variable region amino acid sequences as set forth below:

```
8C7 V_H Protein Sequence:
                                              (SEQ ID NO: 1)
EVQLQQSGAELARPGSSVKLSCKASGYTFTNYWLQWVKQRTGQGLEWIGA

IYPRDGDAKYSQKFKDKASLTVNESSSTAYMHLSALASEDSAVYYCARAN

YGLYYAMDRWGQGTSVTVSS

8C7 V_L Protein Sequence:
                                              (SEQ ID NO: 2)
DIFLTQSPANMSVSPGERVSFSCRASQNIGTNIHWYQQRTNGSPRLLIKY

ASESISGIPSRFSGSGSGTDFILSINTVESEDIAVYFCQQSNRWPFTFGS

GTKLEVIR
```

The CDR1, 2 and 3 amino acid sequences are underlined and numbered based on the Kabat numbering system. The CDR1, 2 and 3 amino acid sequences are set forth in SEQ ID NOs: 13-18.

A particular aspect of the invention provides a recombinant humanized antibody or antibody fragment which binds ADAM10. Preferably, the recombinant humanized antibody or antibody fragment specifically, selectively or preferentially binds a proteolytically active form of an ADAM10 protease.

Suitably, the recombinant humanized antibody or antibody fragment comprises one or more amino acids or amino acid sequences of a human immunoglobulin.

In one embodiment, the one or more amino acids or amino acid sequences are of an Fc region and/or constant region of a human immunoglobulin, such as IgG1 although without limitation thereto. Non-limiting examples are set forth in SEQ ID NOS: 7 and 8, and include fragments and variants thereof.

A non-limiting example of an antibody or antibody fragment according to this embodiment is a human Fc chimerised version of mAb 8C7 referred to herein as "ch8C7".

In another embodiment, the one or more amino acids or amino acid sequences are of a variable region of a human immunoglobulin light chain or heavy chain.

In an embodiment, a human immunoglobulin heavy chain variable region comprises the amino acid sequence of SEQ ID NO:3, or a fragment or variant thereof.

In an embodiment, a human immunoglobulin light chain variable region comprises the amino acid sequence of SEQ ID NO:4, or a fragment or variant thereof.

In a particular embodiment, the recombinant humanized antibody or antibody fragment comprises the amino acid sequence of SEQ ID NO:3, or a fragment or variant thereof and the amino acid sequence of SEQ ID NO:4, or a fragment or variant thereof. Preferably, the recombinant humanized antibody or antibody fragment is of the human IgG1-κ subtype. A non-limiting example of this embodiment is a "fully humanised" version of 8C7 designated herein as "hu8C7".

In a general embodiment, the antibody or antibody fragment, inclusive of recombinant humanized antibody fragments, may comprise respective light chain and heavy chain variable regions that each comprise CDR 1, 2 and 3 amino acid sequences present in SEQ ID NO:1, SEQ ID NO:2, SEQ ID NO:3 and/or SEQ ID NO:4, or a variant thereof. This includes an amino acid sequence of at least a portion of an entire CDR1, 2 or 3, such as present in SEQ ID NO:1, SEQ ID NO:2, SEQ ID NO:3 and/or SEQ ID NO:4, or a variant thereof. By way of example, this may include at least 5, 6, 7, 8, 9, 10, 11, 12, 13 or 14 contiguous amino acids of an entire CDR1, 2 or 3, such as present in SEQ ID NO:1, SEQ ID NO:2, SEQ ID NO:3 and/or SEQ ID NO:4, or a variant thereof. A preferred antibody fragment comprises at least one entire light chain variable region CDR and/or at least one entire heavy chain variable region CDR set forth in SEQ ID NO:1, SEQ ID NO:2, SEQ ID NO:3 and/or SEQ ID NO:4, or a variant thereof.

In general, as used herein "variants" may comprise an amino acid sequence at least 80%, at least 85%, at least 90% or at least 91%, 92%, 93%, 94%, 95%, 96%, 97%, 98% or 99% identical to an amino acid sequence such as set forth in any one of SEQ ID NOS:1, 2, 3, 4, 7 and/or 8, or a fragment comprising a CDR region of SEQ ID NOS:1, 2, 3 and/or 4.

In some embodiments, an antibody or antibody fragment may comprise an amino acid sequence at least 80%, at least 85%, at least 90% or at least 91%, 92%, 93%, 94%, 95%, 96%, 97%, 98% or 99% identical to at an amino acid sequence of least one immunoglobulin heavy chain and/or light chain CDR present in the amino acid sequence set forth in SEQ ID NO:1, SEQ ID NO:2, SEQ ID NO:3 and/or SEQ ID NO:4.

In some embodiments, the antibody or antibody fragment may comprise one, two or three immunoglobulin heavy chain and/or light chain CDRs present in the amino acid sequence set forth in SEQ ID NO:1, SEQ ID NO:2, SEQ ID NO:3 and/or SEQ ID NO:4, or one, two or three immunoglobulin heavy chain and/or light chain CDRs respectively at least 80%, at least 85%, at least 90% or at least 91%, 92%, 93%, 94%, 95%, 96%, 97%, 98% or 99% identical to an amino acid sequence of a heavy chain and/or light chain CDR present in the amino acid sequence set forth in SEQ ID NO:1, SEQ ID NO:2, SEQ ID NO:3 and/or SEQ ID NO:4.

Terms used herein to describe sequence relationships between respective proteins include "comparison window", "sequence identity", "percentage of sequence identity" and "substantial identity". Because respective amino acid sequences may each comprise: (1) only one or more portions of a complete sequence that are shared by respective nucleic acids or proteins, and (2) one or more portions which are divergent between the nucleic acids or proteins, sequence comparisons are typically performed by comparing sequences over a "comparison window" to identify and compare local regions of sequence similarity. A "comparison window" refers to a conceptual segment of typically at least 6, 10, 12, 20 or more contiguous residues that is compared to a reference sequence. The comparison window may comprise additions or deletions (i.e., gaps) of about 20% or less (e.g. 5, 10 or 15%) as compared to the reference sequence (which does not comprise additions or deletions) for optimal alignment of the respective sequences. Optimal alignment of sequences for aligning a comparison window may be conducted by computerised implementations of algorithms (for example ECLUSTALW and BESTFIT provided by WebAngis GCG, 2D Angis, GCG and GeneDoc programs, incorporated herein by reference) or by inspection and the best alignment (i.e., resulting in the highest percentage homology over the comparison window) generated by any of the various methods selected.

The invention also provides one or more isolated nucleic acids encoding a recombinant humanized antibody or antibody fragment, a genetic construct comprising the one or more isolated nucleic acids and/or a host cell comprising the genetic construct.

As used herein, a "nucleic acid" may be a single- or double-stranded DNA, RNA or DNA-RNA hybrids inclusive of cDNA, genomic DNA, mRNA, tRNA, oligonucleotides, primers and probes, although without limitation thereto. Preferably, the genetic construct is suitable for expression of the one or more isolated nucleic acids, comprising one or more of a promoter, enhancer, polyadenylation sequence, bacterial origin or replication, selection marker, splice donor/acceptor and Kozak sequence, as are well understood in the art. Suitably, the genetic construct is expressible in a host cell inclusive of bacterial, mammalian, yeast, insect, plant and amphibian host cells, although without limitation thereto.

In an embodiment, the nucleic acid comprises a nucleotide sequence set forth in any one of SEQ ID NOS:5, 6, 9 or 10, or a nucleotide sequence at least 70%, 75%, 80%, 85%, 90%, 95%, 96%, 97%, 98% or 99% identical thereto.

In one aspect the invention therefore provides a method of detecting a proteolytically active form of an ADAM protease, said method including the step of selectively binding an antibody or antibody fragment to the proteolytically active form of the ADAM protease to thereby detect the proteolytically active form of the ADAM protease.

Suitably, the ADAM protease is expressed by a cell, including but not limited to lymphocytes, hepatocytes, kidney cells, epithelial cells, neural cells, vascular smooth muscle cells, intestinal epithelium and lung cells, inclusive of normal or non-malignant cells and tumour cells, although without limitation thereto.

In another aspect, the invention provides a method of detecting a tumour cell, said method including the step of binding an antibody or antibody fragment which specifically, selectively or preferentially recognizes a proteolytically active form of an ADAM protease expressed by the tumour cell to thereby detect the tumour cell.

As generally used herein, the terms "cancer", "tumour", "malignant" and "malignancy" refer to diseases or conditions, or to cells or tissues associated with the diseases or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumour markers, loss of tumour suppressor expression or activity and/or aberrant or abnormal cell surface marker expression.

Some tumour cells typically express relatively increased levels of a proteolytically active form of an ADAM protease (e.g. compared to normal or non-malignant cells, whereby an antibody or antibody fragment such as 8C7 mAb is capable of distinguishing tumour cells from normal or non-malignant cells. Typically, the proteolytically active form of the ADAM protease expressed by tumour cells is a high molecular weight form of an ADAM protease which comprises the intramolecular disulfide bonds as hereinbefore described. ADAM proteases may exist in a high molecular weight form ("high molecular weight or HMW ADAM") or in a low molecular weight form ("LMW") as a result of release of an N-terminal prodomain by furin or other pro-protein convertases. Contrary to previous understanding, the inventors have shown that the HMW form of ADAM10 proteases is proteolytically active and that ADAM10 protease does not require release of the N-terminal prodomain to become proteolytically active.

In some embodiments, the tumour cells co-express relatively increased levels of a proteolytically active, HMW form of an ADAM protease and CD133. The tumour cells may further express one or more members of the Notch, Eph and/or erbB receptor families. Non-limiting examples of tumour cells include leukemias and lymphomas, lung cancer, colon cancer, adenomas, neuroblastomas, brain, renal and kidney tumours, prostate cancers, sarcomas and melanoma. For a more comprehensive review of potentially relevant tumours the skilled person is directed to Murphy, G., 2008, Nature Rev Cancer. 8 929-941, Mochizuki S & Okada Y, 2007, Cancer Sci 98, 621-628 Groth, C & Fortini M E, 2012, Semin Cell Dev Biol. 23:465-72.

It will therefore be understood that an antibody or antibody fragment disclosed herein may be used to detect tumour cells, to assist medical diagnosis of a cancer or cancer symptoms. Suitably, the method includes detecting the proteolytically active form of the ADAM protease expressed by tumour cells present in, or obtained from, a biological sample. In certain embodiments, the biological sample may be a pathology sample that comprises one or more fluids, cells, tissues, organs or organ samples obtained from a mammal. Non-limiting examples include blood, plasma, serum, lymphocytes, urine, faeces, amniotic fluid, cervical samples, cerebrospinal fluid, tissue biopsies, bone marrow and skin, although without limitation thereto.

Suitably, detection of the proteolytically active ADAM protease includes the step of forming a detectable complex between an antibody or antibody fragment and the proteolytically active ADAM protease. The complex so formed may be detected by any technique, assay or means known in the art including immunoblotting, immunohistochemistry, immunocytochemistry, immunoprecipitation, ELISA, flow cytometry, magnetic bead separation, and biosensor-based detection systems such as surface plasmon resonance, although without limitation thereto.

To facilitate detection the antibody may be directly labeled as hereinbefore described or a labeled secondary antibody may be used. The labels may be as hereinbefore described.

In some embodiments, detection methods may be performed in "high throughput" diagnostic tests or procedures such as performed by commercial pathology laboratories or in hospitals.

It will therefore be appreciated that another aspect of the invention provides a kit for detecting a proteolytically active form of an ADAM protease and/or a tumour cell as hereinbefore described, the kit comprising an antibody or antibody fragment as hereinbefore described.

The antibody or antibody fragment may be labeled with biotin, an enzyme, fluorophore or other label as previously described. Alternatively, the antibody or antibody fragment is unlabeled and a secondary antibody comprises a label. In embodiments where the antibody or antibody fragment or the secondary antibody is labeled with an enzyme, the kit may further comprise an appropriate substrate substrate such as diaminobanzidine (DAB), permanent red, 3-ethylbenzthiazoline sulfonic acid (ABTS), 5-bromo-4-chloro-3-indolyl phosphate (BCIP), nitro blue tetrazolium (NBT), 3,3',5,5'-tetramethyl benzidine (TNB) and 4-chloro-1-naphthol (4-CN), although without limitation thereto. A non-limiting example of a chemiluminescent substrate is Luminol™, which is oxidized in the presence of HRP and hydrogen peroxide to form an excited state product (3-aminophthalate).

The kit may further comprise one or more reaction vessels (e.g multiwell plates, tubes etc), control antibodies and instructions for use.

A further aspect of the invention provides a method of inhibiting an ADAM protease and/or one or more downstream signalling molecules in a cell, including the step of binding an antibody or antibody fragment which selectively recognizes a proteolytically active form of the ADAM protease to the ADAM protease expressed by the cell, to thereby at least partly inhibit a biological activity of the ADAM protease and/or one or more downstream signalling molecules in the cell.

Preferably, the cell is a tumour cell.

In some embodiments, the tumour cell is of a leukemia, lymphoma, lung cancer, colon cancer, breast cancer, adenoma, neuroblastoma, brain tumour, renal tumour, prostate cancer, sarcoma or melanoma.

In certain embodiments, the tumour cell expresses CD133. The tumour cell that expresses CD133 may be a cancer stem cell (CSC).

A still further aspect of the invention provides a method of treating or preventing cancer in a mammal, said method including the step of administering to the mammal an antibody or antibody fragment which selectively recognizes a proteolytically active form of the ADAM protease to thereby treat cancer in the mammal.

As disclosed herein, tumour cells typically express relatively increased levels of a proteolytically active form of an ADAM protease (e.g. compared to normal or non-malignant cells). Typically, the proteolytically active form of the ADAM protease expressed by tumour cells is a high molecular weight form of an ADAM protease, although this form may additionally or alternatively comprise the intramolecular disulfide bonds referred to hereinbefore. Furthermore, treatment of human tumour-bearing mice with an antibody such as mAb 8C7 caused a significant, dose-dependent inhibition of tumour growth, with no discernible detrimental effects on the overall health of the mice The treated tumours also displayed significantly reduced levels of downstream signalling molecules or effectors such as Notch, Eph, and erbB receptors and their ligands as well as MET, suggesting down-regulation of multiple oncogenic signalling pathways. This suggests that antibodies such as 8C7 may act, at least in part, by inhibiting the activation of the ADAM substrate, Notch. Furthermore, antibodies such as mAb 8C7 binding to ADAM prevent Notch cleavage and activation and largely blocked lymphoma proliferation, thereby demonstrating effective inhibition of Notch pathway activation. In certain embodiments, antibodies such as 8CT may target and/or deplete tumour cells that express CD133. The tumour cell that expresses CD133 may be a cancer stem cell (CSC).

Accordingly, it is proposed that, an antibody or antibody fragment disclosed herein may be suitable for administration to mammals, particularly humans, to treat or prevent cancer. As used herein, "treating", "treat" or "treatment" refers to a therapeutic intervention, course of action or protocol that at least ameliorates a symptom of cancer after the cancer and/or its symptoms have at least started to develop. As used herein, "preventing, "prevent" or "prevention" refers to therapeutic intervention, course of action or protocol initiated prior to the onset of cancer and/or a symptom of cancer so as to prevent, inhibit or delay or development or progression of the cancer or the symptom.

In particular embodiments, the invention may relate to treating, preventing, inhibiting or delaying tumour cell metastasis.

The antibody or antibody fragment suitably targets tumour cells that express proteolytically active ADAM, as hereinbefore described. Accordingly, the antibody or antibody fragment may be sufficient to suitably inhibit the ability of proteolytically active ADAM to activate downstream substrates or effectors such as one or members of the Notch, erbB and Eph signalling pathways, although without limitation thereto.

In other embodiments, the antibody or antibody fragment may be coupled or conjugated to a cytotoxic agent that facilitates killing or disabling tumour cells that express proteolytically active ADAM. The cytotoxic agent may be a radionuclide, a chemotherapeutic drug, a mutagen, a toxin, a mitosis inhibitor or other anti-proliferative agent, a pro-apoptotic agent, a DNA intercalating agent or any other agent that assists or causes killing or disabling of tumour cells. Non-limiting examples of radionuclides include $^{211}$At, $^{212}$B1, $^{213}$Bi, 125I, $^{111}$In, $^{193}$Pt and $^{67}$Ga, although without limitation thereto.

Chemotherapeutic drugs, mutagens, toxins, mitosis inhibitors, pro-apoptotic agents and DNA intercalating agents may include doxorubicin, N-acetyl-γ-calicheamicin, maytansinoids, taxoids, auristatins and duocarmycins, although without limitation thereto. Chemotherapeutic drugs, mutagens, toxins, mitosis inhibitors, pro-apoptotic agents and DNA intercalating agents may be coupled to the antibody or antibody fragment by a cleavable or non-cleavable linker to form an antibody-drug conjugate (ADC). Typically, the ADC is internalized by the tumour cell where the cleavable linker is cleaved to release the drug into the cell. In the case of non-cleavable linkers, these may be preferred where it is essential that the drug is entirely localized to the targeted tumour cell and there is no "leakage" of the drug from the targeted tumour cell into adjacent cells, tissues or fluids. In some embodiments, the chemotherapeutic drugs, mutagens, toxins, mitosis inhibitors, pro-apoptotic and DNA intercalating agents may be in the form of a pro-drug which is activated upon internalization inside a targeted tumour cell.

In other embodiments, the method and/or composition may include a combination therapy where the antibody or antibody fragment disclosed herein (e.g 8C7 mAb) is combined with another therapy including but mot limited to radiotherapy, chemotherapy, natural or holistic therapies or other immunotherapies that target cancers. By way of example, the antibody or antibody fragment disclosed herein (e.g 8C7 mAb) may be administered in combination with another therapeutic agent such as one or more chemotherapeutic drugs, antibodies, mutagens, toxins, mitosis inhibitors, pro-apoptotic agents and/or DNA intercalating agents, such as hereinbefore described. In these embodiments, the antibody or antibody fragment and said another therapeutic agent are not coupled or conjugated, but are administered as separate molecules together or sequentially. A non-limiting example is combination therapy with irenotecan, a chemotherapeutic agent used to treat colorectal cancer.

Suitably, the antibody or antibody fragment and optionally, said another therapeutic agent, is administered to a mammal as a pharmaceutical composition comprising a pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, liposomes and other lipid-based carriers, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991), which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunotherapeutic compositions, proteinaceous vaccines and nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Compositions of the present invention suitable for oral or parenteral administration may be presented as discrete units such as capsules, sachets or tablets each containing a predetermined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

The methods and compositions of the invention may be applicable to any mammal in which an ADAM10 protease is expressed by tumour cells.

In some embodiments, the tumours comprise tumour cells that co-express relatively increased levels of a proteolytically active form of an ADAM protease and CD133. The tumour cells may further express one or more members of the Notch, Eph and/or erbB receptor families. Non-limiting examples of cancers or tumours that may be treated or prevented include leukemias and lymphomas, lung cancer, colon cancer, adenomas, neuroblastomas, brain, renal and kidney tumours, prostate cancers, sarcomas and melanoma.

In particular embodiments, the term "mammal" includes but is not limited to humans, performance animals (such as horses, camels, greyhounds), livestock (such as cows, sheep, horses) and companion animals (such as cats and dogs).

So that the present invention may be more readily understood and put into practical effect, the skilled person is referred to the following non-limiting examples.

EXAMPLES

Introduction

We previously defined the structure of the ADAM10 D+C domains and identified a substrate-binding pocket within the C domain that specifies ligand cleavage[6]. To further define the function of the substrate binding pocket, we raised antibodies against ADAM10, one of which, mAb8C7, specifically recognises the substrate binding domain, and inhibits ADAM10-mediated cleavage of Eph receptor ligands (ephrins) and ephrin/Eph-dependent signalling and cell segregation in vitro[27]. We thus sought to test 8C7 as a targeted therapeutic in tumour models. We find 8C7 treatment inhibits tumour growth of human colon xenografts, at least in part due to inhibition of Notch signalling, and down-regulation of Notch, EGFR and Eph receptor levels. In line with the critical role of Notch in maintenance of an undifferentiated cell phenotype, including that of tumour initiating colon cancer cells[29,19], we find 8C7 selectively targets tumour cells expressing the putative cancer stem cell (CSC) marker CD133 and displaying active Notch-signalling within tumours[30]. CSCs are known to contribute to chemotherapy resistance, and accordingly, 8C7 reduces CSC levels and effectively inhibits tumour re-growth following chemotherapy. Importantly, we demonstrate that 8C7 selectively binds an active form of ADAM10, which we find to be over-expressed in mouse tumour models and in several human solid tumours, suggesting its potential as human cancer therapeutic and diagnostic.

Materials & Methods

Cell Culture and Reagents

Human colorectal carcinoma cell line LIM1250 (obtained from the Ludwig Institute for Cancer Research, Melbourne, Australia) was maintained in RPMI 1640/10% FCS in 10% $CO_2$/90% air. ADAM10-/- mouse embryonic fibroblasts[5] were maintained in DMEM 10% FCS in 5% $CO_2$/95% air atmosphere.

Mutagenesis

The sequence encoding full length human (OriGene) ADAM10 was subcloned into pcDNA3.1 vector (Invitrogen), including an N-terminal prolactin signal sequence and a C-terminal thrombin cleavage site. AxxA point mutation to human ADAM10-turbo-myc(OriGene) was introduced by site-directed mutagenesis (Quickchange XL, Stratagene) by introducing Alanines at Cys594 and Cys597 respectively. Mutants were transfected into MEF ADAM10-/- using X-treme transfection reagent (Roche) to confirm its expression by Western blot and Immunofluorence.

Immunoprecipitation and Western Blotting

Frozen human tissue samples were obtained from surgical biopsies between 1995 and 2007, held at the Austin Health Tissue Bank, under approval from the Monash University Human Research Ethics Committee. For protein analysis of tumours and tissues, 50 mg tissue was homogenised in 1 ml RIPA buffer (50 mM Tris-HCL pH 7.4, 150 mM NaCl, 1% Triton-X-100, 0.5% Sodium Deoxycholate, 0.1% SDS, phosphatase and protease inhibitor cocktail); and protein concentration determined by BCA assay (Pierce). 20 ug of total lysates or immunoprecipitates from 100 ug of lysates were analysed by SDS-PAGE and Western blot. After various treatments, including exposure to 1 mM DTT, 40 mM $H_2O_2$, 1 µg/mL EGF or 1.5 µg/mL cross-linked EphrinA5-Fc{Lawrenson, 2002 #237}, and after 3 washes in PBS cell lysates were prepared in KALB lysis buffer (1.5 M NaCl, 0.5 M HEPES, 0.05 M EDTA, pH 7.4, 1% Triton X-100, phosphatase and protease inhibitor cocktail); loading levels for analysis were equalised on the basis of actin levels by performing Western blot analysis on cell lysates. Immunoprecipitation was done with mAb8C7 or with mAb4A11-coupled to Minileak beads (according to manufacturers instructions, KEM EN TEC, Denmark), or with soluble 8C7 or anti-ADAM10 polyclonal antibodies (pAb) (Abcam pAb 39177) followed by Protein A Sepharose. ADAM10 was detected on Western blots with Abcam pAb 39177 and anti-rabbit-HRP secondary antibodies and visualized using an ECL substrate (Supersignal; Thermo Fisher Scientific). Samples reduced in SDS-samples buffer with 20 mM Dithiothreitol (5 min, 95° C.) or left non-reduced were routinely analysed.

Maleimide-Biotinylation of Free Cysteine Residues

LIM1215 colon carcinoma cells were starved overnight in serum free RPMI and used at 80% confluency. Cells were treated with 2.5 mM Methyl-PEG12-maleimide (MPM, Thermo Scientific) in serum free RPMI for 30 min at 4° C. to label any free cell surface protein cysteines. After three washes (PBS) cells were treated at room temperature with 5 µg/ml Protein Disulfide Isomerase (PDI, Sigma), or 10 µM DTT for indicated times. Following washes (PBS), free cysteines that formed after PDI treatment was reacted with Maleimide-PEG2-biotin (MPB) (Thermo Scientific) in serum free RPMI for 1 hour at 4° C. For analysis, washed (PBS) cells were lysed in KALB lysis buffer containing 5 mM N-ethylmaleimide prior to IP and Western blot analysis.

In-vitro biotinylation of 8C7 and 4A11 immunoprecipitates was performed in a similar manner using total washed IPs from LIM1215 cells.

Furin Cleavage mAb8C7 and 4A11 IPs from LIM1215 cell lysates were treated with furin (1 unit/100 µl, New England Biolabs) in a buffer specified by the supplier (100 mM HEPES, pH 7.5 @ 25° C., 0.5% Triton X-100, 1 mM CaCl2) for 2 hours at 37° C. Samples were washed three times with PBS, prior to treatment with SDS-PAGE sample buffer (95° C., 5 min) and Western blot analysis.

Activity Assay

ADAM10 was immunoprecipitated (IPed) by mixing 8C7 and 4A11 mAbs coupled to mini-leak beads with LIM1215 colon carcinoma cell lysates and human colorectal tumour lysates. IPs were treated with Mca-PLAQAV-Dpa-RSSSR-NH2 fluorogenic peptide substrate (R&D Systems, USA, cat No, ES003), 10 µM at 37° C. for 1 hour, or using HPLC-purified monomeric ephrinA5-Fc{Vearing, 2005 #3050} at 50 µg/mL at room temperature for 20 mins. Fluorescence substrate supernatants were analysed using a FLUOstar OPTIMA (BMG Labtech) plate reader at 320 nm excitation and 405 emission wavelengths, cleavage of ephrin-A5 Fc analysed by Western blot analysis with α-ephrinA5 antibodies (R&D Systems, USA).

Tissue Immunohistochemistry and Immunofluorescence

Tissues were OCT-embedded (Tissue-TEK), sectioned (6-µm) and fixed (10 min, acetone). For IHC, Vector Labs ABC secondary antibody staining kit was used to detect the bound primary antibodies. Sections, counterstained with Haemotoxylin were imaged on an Olympus DotSlide system. For TUNEL, tumours were formalin fixed and paraffin-embedded. For IF, sections were incubated with directly conjugated primary or secondary antibodies, nuclei counterstained with Hoechst, and slides mounted with Fluoromount (Southern Biotech, Birmingham, Ala. USA) for imaging on a Leica confocal (SP5) microscope.

Flow Cytometry

Single cell suspensions were made from LIM1215 tumours by digesting tumour pieces with Collagenase Type 3/Deoxyribonuclease I (Worthington Biochemical Corp.) in HBBS (Gibco, Invitrogen, 1 h, 37° C.), filtering through successive 40 μm and 20 μm sieves and treatment with Red Blood cell lysing buffer (Sigma-Aldrich). Cells were labelled with conjugated anti-CD133 (Miltenyi Biotec) and FACS sorted on an Influx Cell Sorter (BD biosciences). Dead cells were detected with propidium iodide. For analysis of cell cultures, trypsinised cells were washed with FACS buffer (PBS, 1% FCS, 1 mM EDTA), and labelled for 30 min at 4° C. with fluorophore-conjugated mAbs as indicated, before analysis on a LSRII flow cytometer (Beckton Dickenson). Subsequent analysis was with FLOWJO software (TreeStar, Calif.).

Detection of Reactive Oxygen Species (ROS) in Tumour Cell Isolates

Tumours from mice injected with alexa-labelled 8C7 (100 μg) were recovered and cell suspensions prepared as above. FACS sorted 8C7 bound/unbound tumour cells were tested using a reaction mix that included 50 μM Amplex Red (Invitrogen) and 0.1 U/ml HRP (Invitrogen) in Krebs Ringer Phosphate. 20 μl of 8C7 bound tumour cells (a total of $5 \times 10^4$) were added to 100 μl of the pre-warmed reaction mixture and incubated 1 hour at 37° C. A microplate reader (CLARIOstar, BMG Labtech) was used to measure fluorescence (Excitation 530-560 nm and emission peak 590 nm).

Xenograft Experiments

Athymic nude mice (BALB/c, 4- to 6-week old; male) were from Animal Resources Centre, Canning Vale, WA, Australia. Animal procedures were conducted in accordance with guidelines of the Monash University Animal Ethics Committee. $7 \times 10^6$ LIM1250 cells in 200 ul PBS/30% growth factor reduced Matrigel (BD Biosciences) were injected subcutaneously in the dorsal flanks of the mice. Once tumour volumes reached 75-150 mm$^3$ (measured by callipers), mice were treated twice weekly by IP injection with either PBS, 8C7 or control antibody as indicated. Tumours and tissues were recovered for protein analysis, imaging by immunofluorescence microscopy or IHC, or flow cytometry.

Crystallization, Data Collection and Structure Determination

Expression and Purification of ADAM10 Disintegrin (D) and Cysteine (C) Rich Domain The sequence encoding bovine ADAM10 disintegrin and cysteine-rich domains (residues 455-646) (ADAM10: D+C) was subcloned as Fc fusion into a pcDNA3.1 vector (Invitrogen), including an N-terminal prolactin signal sequence and a C-terminal thrombin cleavage site followed by the Fc domain of human IgG, for expression in human embryonic kidney 293 (HEK293) cells. A stable cell line expressing ADAM10:D+C was generated. Roller bottles were used for large-scale expression of the protein. The initial purification was performed on a Protein-A-Sepharose (Amersham) column and the protein was eluted with 100 mM glycine, 150 mM NaCl pH 3.0. The Fc tag was removed by thrombin cleavage, and ADAM10:D+C was further purified to homogeneity by gel filtration chromatography (SD-200, buffer 20 mM HEPES, 150 mM NaCl, pH7.5). The protein eluted as a monomer (33 kDa). The two ADAM10:D+C bands on the SDS gels correspond to differently glycosylated forms of the recombinant protein and converge into a single band upon enzymatic deglycosylation.

Preparation of F(ab')$_2$ Fragment of the 8C7 Monoclonal Antibody

The F(ab')$_2$ fragment was prepared by digesting the whole IgG (8C7) with pepsin at pH 3.0 (enzyme: substrate ratio 1:100). The reaction was terminated after 2 hrs incubation at room temperature by raising the pH to 8.0. The final purification was performed using gel filtration chromatography (SD-200, buffer 20 mM HEPES, 150 mM NaCl, pH 7.5). The protein eluted as a monomer with molecular weight of approximately 110 kDa.

Crystallization and Structure Determination

For crystallization trials, ADAM10:D+C was mixed with F(ab')2 at 2:1 molar ratio (final concentration 20 mg/ml) in a buffer containing 20 mM HEPES, 150 mM NaCl, and pH 7.5. The complex was crystallized in a hanging drop by vapor diffusion at room temperature against a reservoir containing 0.1 M HEPES, 0.2 M NaCl, and 1.6M ammonium sulfate pH 7.5. Sizable crystals, (space group $P2_12_12_1$; Unit cell: 53.2, 141.7, 268.1, 90.0, 90.0, 90.0) grew after 2 months but could be reproduced in 2 to 3 days using the additive 30% 1, 4 Dioxane. The structure was determined at 2.75 Å resolution using molecular replacement.

Results

Systemic Treatment with the Anti-ADAM10 mAb 8C7 Inhibits Tumour Growth, Preferentially Targeting Notch-active CD133+ Tumour Cells.

We sought to test the effect of anti-ADAM10 mAb8C7 on tumours which co-express high levels of the ADAM10-dependent Notch, Eph, and erbB receptor families. By screening a panel of human colorectal cancer (CRC) cell lines in which these pathways are commonly de-regulated[31], we selected LIM1215 cells, which express high levels of EGFR, EphA2 and ADAM10, are known to be dependent on autocrine EGFR signalling in a mouse xenograft setting[32], and also express high levels of Notch1 and 2, and the notch ligands Jagged 1 and 2.

Figure 10A:
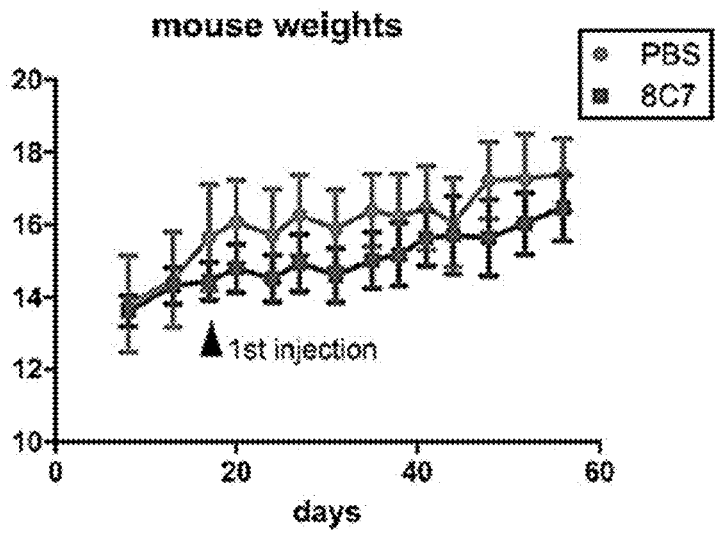
Figure 10B:
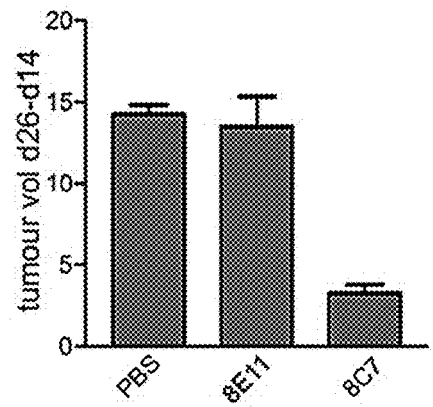
Figure 10C:
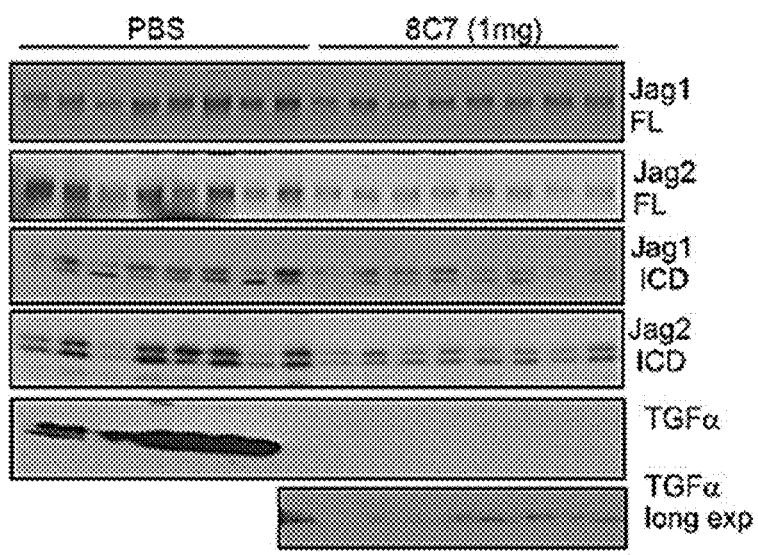
Figure 10D:
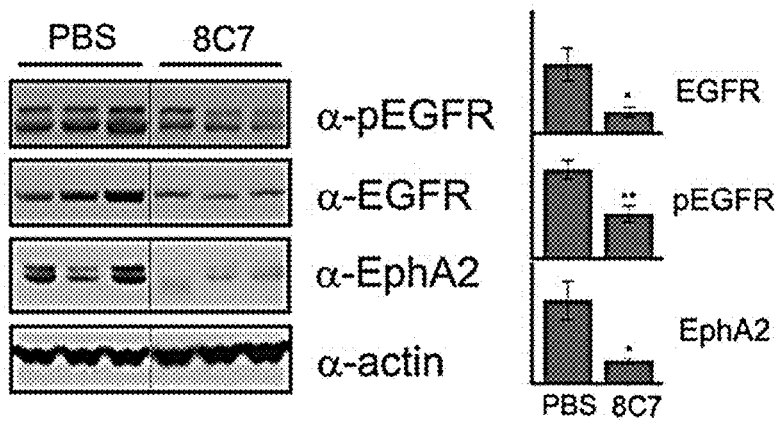

Systemic treatment of mice bearing LIM1215 xenografts with mAb8C7 (8C7) caused a significant, dose-dependent inhibition of tumour growth, as measured by tumour volume and weight (FIG. 1A, 1B), but with no discernible detrimental effects on overall health of the mice as measured by their weight (FIG. 10A). In comparison, the control mAb8E11, raised alongside 8C7 but not recognising ADAM10, did not inhibit tumour growth (FIG. 10B). The treated tumours also displayed less vascular staining (α-CD31, FIG. 1C), and increased apoptosis (TUNEL staining, FIG. 1D), suggesting inhibitory effects on blood supply. Western blot analysis of tumour protein extracts showed significantly reduced levels of notch, Eph, and erbB receptors and their ligands (FIG. 1E, 1C, 10D), as well as MET, suggesting down-regulation of multiple oncogenic signalling pathways. Considering the known role of Notch to promote neoangiogenesis, and to transcriptionally control[33] EGFR[34], Ephs and ephrins[35,36] and its own expression, this suggests that 8C7 may act, at least in part, by inhibiting the activation of the prominent ADAM10 substrate, Notch.

Figure 2A:
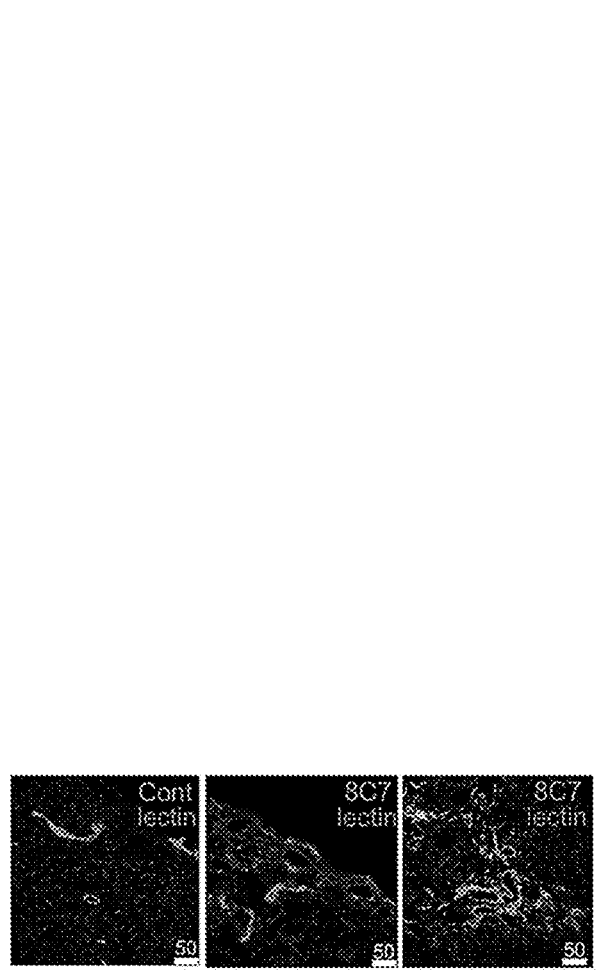
FIGS. 2A-2D. The mAb 8C7 preferentially targets CD133+/NICD+ tumour cells in the tumour rim.

To analyse 8C7 targeting within the tumour, we injected LIM tumour xenograft-bearing mice with Alexa[647]-labelled 8C7 and, to label the vasculature, three days later with Rhodamine-labelled Ricininus Communis Agglutinin ([Rhodamine] RCA)-lectin, before tumours were resected and sections analysed by confocal microscopy. We observed mAb8C7 binding to the tumour tissue, particularly within the outer margin and around blood vessels, visible by [Rhodamine] RCA-lectin staining (FIG. 2A). In contrast there was detectable, but reduced mAb8C7-immuno reactivity within the bulk of the tumour.

Figure 2B:
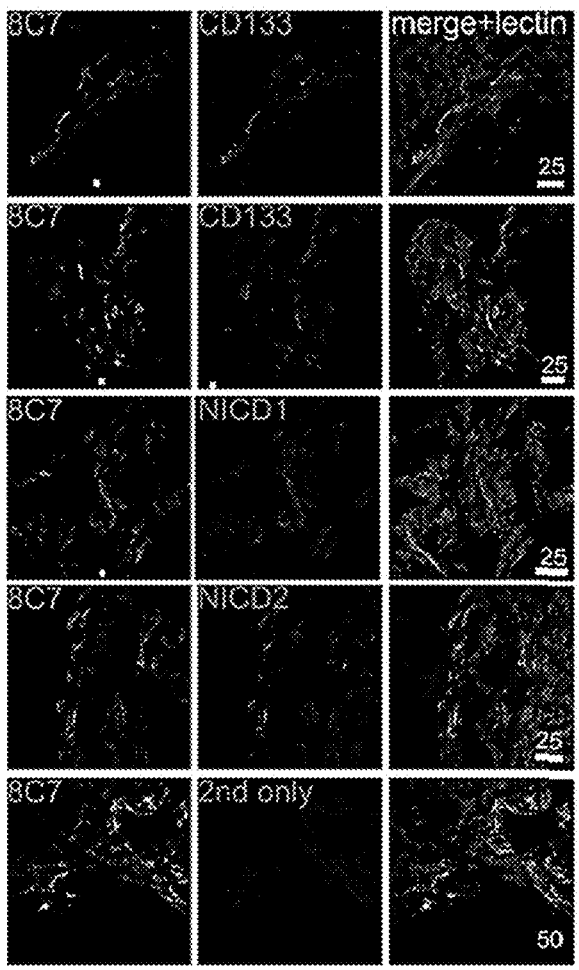
Figure 2C:
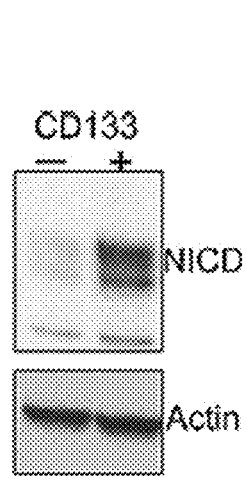
Figure 2D:
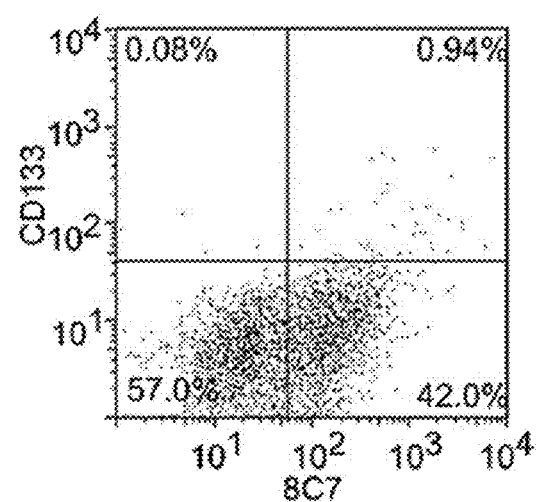

Recently, colon carcinoma initiating cells, marked by expression of the putative stem cell marker CD133 and by active notch signalling, have been found, selectively associated with Notch ligand Jagged-1-expressing vascular endothelial cells, in colon tumour xenografts[30]. We therefore co-stained 8C7-injected LIM1215 colon tumour xenografts with antibodies against CD133 and against the Notch intracellular domain (NICD), generated during active Notch signalling by serial cleavage by α- and γ-secretases. Notably, mAb 8C7 preferentially targeted an anti-CD133-stained cell population, in addition to co-staining anti-NICD1 and NICD2 positive cells (FIG. 2B), overall confirming activated Notch receptor signalling in these putative tumour-initiating cells. Interestingly, the lectin-labelled vessel cells co-stained with antibodies against Jagged1, consistent with reported endothelial expression of Jagged1[30], whereas Jagged2 was found on a separate cell population within the same microenvironment (FIG. 11A, 11B). FACS analysis of dissociated tumours from mice injected with Alexa$^{647}$-8C7 showed significant tumour staining, whereby, in support of the imaging data, cells with brightest 8C7 staining were also CD133$^+$ (FIG. 2D). We also isolated CD133-enriched and depleted cell populations from tumours which, when compared for active NICD1 levels by Western blot, clearly confirmed high levels of Notch activity in the CD133-enriched population (FIG. 2C).

mAb 8C7 Binding to ADAM10 Prevents Notch Cleavage and Activation

Figure 3A:
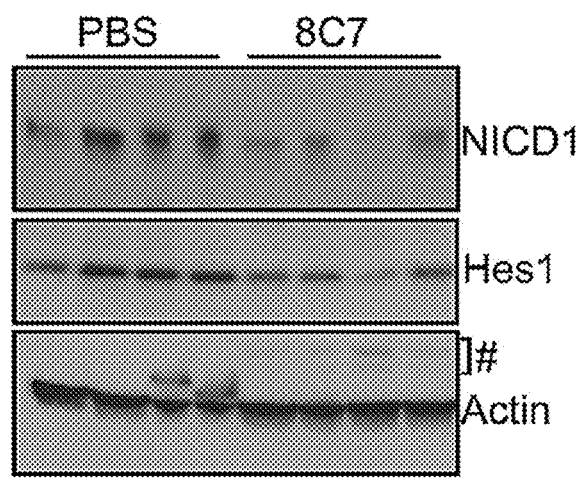
FIGS. 3A-3C. Treatment with 8C7 inhibits Notch signalling in LIM1215 tumours.
Figure 3B:
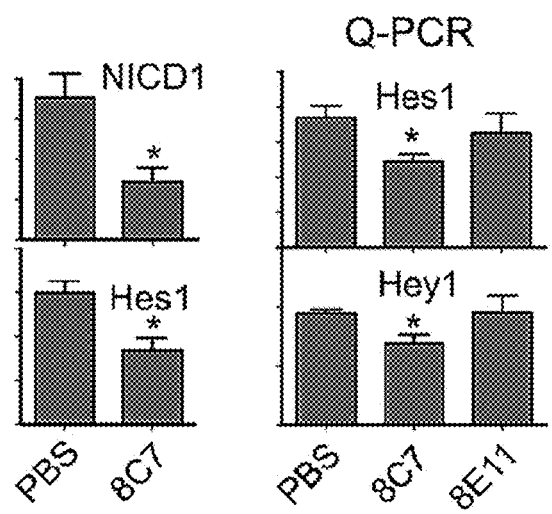
Figure 3C:
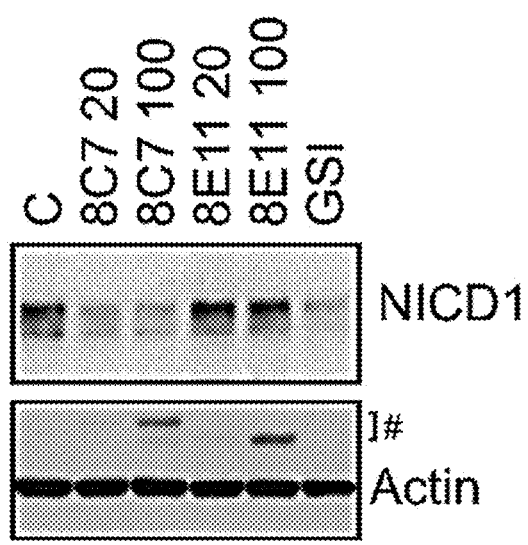
Figure 3C:
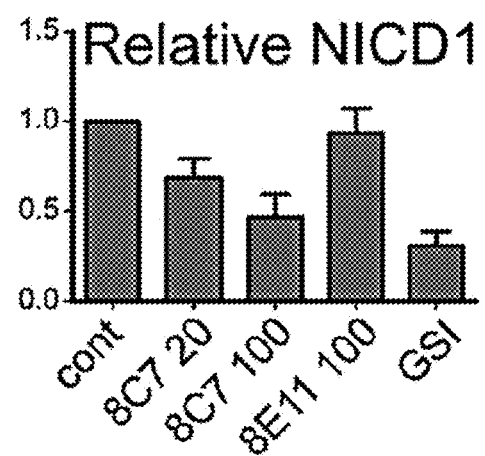

Since our anti-ADAM10 mAb 8C7 preferentially targeted cells with active Notch signalling and inhibited tumour growth, and we previously showed its ability to inhibit ADAM10-mediated Eph receptor signalling[27], we sought to determine if 8C7 also inhibits Notch signalling. We treated mice bearing LIM1215 tumours for 3 weeks (when tumour growth rate was most affected) before recovering tumours and analysing by Western blot with anti-NICD1 antibody. Comparison of 8C7 and control-treated tumours showed a significant decrease in levels of active Notch (FIG. 3A). Furthermore the Notch target Hes1 was also substantially decreased in the tumours from treated mice, as confirmed by quantitative PCR (FIG. 3B). We thus tested if this effect was due to direct inhibition of ADAM10-mediated Notch activation by 8C7, by in vitro treatment of CD133$^+$-enriched tumour cell isolates with 8C7, the control mAb 8E11, or with γ-secretase inhibitor (GSI). 4h-treatment with 8C7, but not with the control mAb, decreased NICD1 levels significantly and comparable to inhibition with GSI (FIG. 3C).

We also used a co-culture model in which Notch-dependent lymphoma survival and proliferation is afforded by contact with Jagged1-expressing vascular endothelial cell (HUVEC) feeder cells, which have been transduced with the adenoviral gene fragment E4ORF1 to drive Akt auto-activation and allow their serum-free propagation[37] (FIG. 12A). Treatment with mAb 8C7 largely blocked lymphoma proliferation in this setting (FIG. 12B, 12C), demonstrating its effective inhibition of Notch pathway activation.

mAb 8C7 Preferentially Recognises a High Molecular Weight Form of ADAM10 Found Predominantly in Tumour Tissues.

The preferential binding of 8C7 to tumour cells containing elevated Notch signalling prompted us to further investigate the selectivity of 8C7 in tumour-bearing mice. While we previously demonstrated 8C7 binding to mouse ADAM10[27], comparison of tumour and organ tissues from mice, injected 3 days prior with Alexa$^{647}$-labelled 8C7, showed robust staining in tumours, as compared to undetectable staining in all other organs tested, apart from the liver (FIG. 4A). However, it is likely that the low liver staining is due to metastasis of the human tumour cells, previously described for this model, as a control antibody with specificity for human ADAM10 only (4A11) showed similar staining of the liver. By contrast, a control antibody recognising both, human and mouse ADAM10, strongly stained multiple mouse tissues (FIG. 4A, last column). We next analysed tumours and organs from mice treated long term with high (1 mg) doses of 8C7, or untreated mice, by incubating detergent homogenates with Protein A Sepharose to recover 8C7 and bound ADAM10. ADAM10 was clearly detected in Protein A pull-downs from tumour tissue (FIG. 4B, top), while other tissue showed much lower or undetectable levels. By contrast, immunoprecipitation with a control ADAM10 mAb suggested expression of ADAM10 in a range of tissue (apart from colon and intestine) at varying levels (FIG. 4B, bottom). Interestingly, the control mAb detected ADAM10 in these non-tumour tissues predominately as a processed low molecular weight (LMW) form of approximately 64 kDa, whereas in tumours it also recognised the unprocessed high molecular weight (HMW) form, which is preferentially recognised by 8C7.

To assess if 8C7 also recognises the ADAM10 HMW form in other tumour models, we analysed stomach tissue from GP130F knock-in mice[38,39], a transgenic mouse strain that spontaneously forms stomach adenomas in 5-6 weeks old mice. While at 3.5 weeks the HMW ADAM10 was barely detectable in stomach tissue, at 5 and 6 weeks the HMW form was clearly elevated, both in stomach adenomas and in associated stomach tissue, but not in similarly aged wild-type (Wt) mice (FIG. 5A). We have also tested effects of 8C7 on tumour formation in the GP130F knock-in mice. Treatment of mice from around 4 weeks of age for 5 weeks caused a significant inhibition of tumour formation (FIG. 18).

Considering the apparent diagnostic detection by 8C7 of the HMW form of ADAM10 in mouse tumours, we then went on to test human tumour tissues by immunoprecipitation (IP) with 8C7 or a control anti-human ADAM10 mAb (4A11). 4A11 IPs from colon tumour tissue showed a somewhat increased ratio of HMW/LMW ADAM10 compared to apparently normal colon tissue, while remarkably 8C7 specifically recognised the HMW form in human tumour tissue lysate (FIG. 5B). Similarly, 8C7 also specifically bound HMW ADAM10 in lysates from breast, prostate and lung tumours, while 4A11 again bound both forms. Interestingly, 4A11 also detected some HMW ADAM10 in glioblastoma tissue whilst in benign brain tissues lower levels only the LMW form were detected, a finding verified in an independent set of non-tumour brain samples (not shown).

The HMW Form of ADAM10 Recognised by 8C7 Represents the Active Protease.

The above data suggests that 8C7 preferentially targets an unprocessed form of ADAM10 that appears to be elevated in tumours, whereby conversion of full length unprocessed ADAM10 involves release by furin or other pro-protein convertases of the N-terminal prodomain, shown to control ADAM stability and protease activity[40]. We confirmed the HMW form as non-processed ADAM10, since incubation with furin resulted in conversion into LMW ADAM10 (FIG. 13A). We confirmed by mass spectometry of SDS-PAGEresolved HMW and LMW ADAM10 that Pro domain peptides are present only in the BMW band (not shown). Furthermore, we confirmed that the unprocessed form of ADAM10 is present on the cell surface, as suggested by its recognition by 8C7 in treated mice (above): by binding 8C7 to intact LIM1215 cells under culture conditions where endocytosis is inhibited (incubation on ice or in the presence of sucrose), we found a distinct enrichment of HMW ADAM10 in the Protein A-captured IP, as compared to control cells incubated at 37° C. Using the same protocol, the control anti-human ADAM10 mAb 4A11 bound similar amounts of processed and non-processed ADAM10, further confirming the presence also of HMW ADAM10 on the cell surface (FIG. 13B).

Pro-domain processing is generally considered to generate the active form of ADAMs by releasing the Pro domain, which in turn can interact with and inhibit the mature metalloprotease, although for ADAM10 and 17 this does not occur via the cysteine switch mechanism of other metalloproteases[40]. Indeed, in the case of ADAM10 and 17, the Pro domain may have a necessary chaperone function, since addition of recombinant Pro domain rescues the activity of an inactive, prodomain-deleted form of ADAM10[41], while ADAM17 can be activated on the cell surface without requiring removal of the Pro domain[42]. We therefore tested if 8C7 targeted ADAM10 represents an active or inactive population. MAb 8C7 and 4A11 IP from LIM1215 cells again showed preferential binding of 8C7 to ADAM10 enriched in the BMW form, while 4A11, similar to a commercial pAb against the cytoplasmic domain[27], appeared to bind non-discriminately to both HMW and LMW bands (FIG. 6A, top panels). To test for ADAM sheddase activity, we incubated the IPs with recombinant ephrin-A5/human Fc fusion protein, a known ADAM10 substrate[6], or with a quenched fluorogenic peptide substrate, which fluoresces only when cleaved, and related the measured activity to the amount of ADAM10 determined by Western blot with a C-terminal-specific anti-ADAM10 antibody. Both assays revealed that 8C7 IPs contained much higher sheddase activity compared to 4A11 IPs (FIG. 6A, 6B), suggesting that 8C7 selectively targets an active form of ADAM10. Using the same assays to assess ADAM10 from human colon tumour tissue, in which 8C7 preferentially bound the HMW form, we confirmed that 8C7 IPs contained significantly higher sheddase activity than 4A11 IPs (FIG. 6B), indicating that 8C7 selectively recognises an active population of HMW ADAM10. A higher relative sheddase activity in 4A11 IPs in tumour versus LEVI cell lysates likely reflects an overall greater proportion of active ADAM10 in tumour tissue, also captured by the 4A11 mAb, which does not discriminate between active and inactive ADAM10. Furthermore, since 8C7 preferentially binds unprocessed ADAM10, this suggests that processing is not required for ADAM10 activity, similar to ADAM17[42]. We verified this notion by comparing ADAM10 activity in 8C7 IPs, treated with or without furin, revealing no difference in sheddase activity in treated or untreated samples (FIG. 14).

The 8C7 Binding Epitope Implicates the ADAM10 Thioredoxin CXXC Motif, Involved in Regulating ADAM10 Conformation and Activity We previously demonstrated that 8C7 binds the Cysteine-rich (C) domain of ADAM10[27], and earlier had elucidated its protein structure in context with the adjacent Disintegrin (D) domain, revealing a continuous, elongated, slightly curved structure harbouring a negatively charged pocket mediating ADAM10-substrate recognition[6]. To define the exact binding site of 8C7 we determined the protein crystal structure of the ADAM10-D+C domain fragment in complex with a F(ab')$_2$ fragment of 8C7 at 2.8 Å A resolution (Table 1). A model of the structure of the complex is illustrated in FIG. 7A, revealing an overall conformation very similar to that elucidated for the unbound ADAM10D+C[6]. The antibody complementary determining region (CDR) targets the C domain by interacting with $Arg_{557}$, $Asp_{589}$, $Lys_{591}$, $Pro_{628}$, $Tyr_{368}$, $Cys_{639}$, $Asp_{641}$, $Val_{1641}$, $Phe_{642}$, $Arg_{644}$, and $Arg_{646}$, including hydrogen bonds between $Asp_{640}$, $Val_{641}$, $Phe_{642}$, $Arg_{644}$, and $Arg_{646}$ and 8C7 light chain CDR residues (Table 2). This epitope comprises a loop structure that protrudes away from the C-terminal part of the ADAM10 cystein-rich domain, harbouring the substrate-binding pocket encompassing residues $Glu_{573}$, $Glu_{578}$, $Glu_{589}$[6] and is stabilised by two intramolecular disulfide bonds, C594-C639 and C632-C645, one of which forms part of the ADAM10 sequence, $C_{594}HVCC_{598}$ (FIG. 7A, 7B). Interestingly, this sequence represents a conserved thioredoxin CxxC motif, a consensus sequence for protein disulfide isomerase (PDI)-catalysed disulfide exchange reactions that is found in the analogous position of ADAM17. In the case of ADAM17, this motif is necessary for the modulation of protease activity by PDI[24] and by redox changes. Thus, oxidising conditions were found to promote ADAM17 activity[43], thought to be triggered by conformational changes resulting from disulfide isomerisation, a notion that was supported by the finding that PDI treatment alters ADAM17 recognition by conformation specific antibodies'.

In view of these findings, we tested if 8C7 binding to ADAM10 was dependent on modulation of the CxxC motif. Alanine replacement mutation to AxxA clearly ablated binding of 8C7, but not of control antibodies (FIG. 8A), whereby comparable anti-ADAM10 cell surface staining of ADAM10$^{-/-}$ mouse embryonic stem cells (MEFs)[5], transfected with either Wt or AXXA-mutant ADAM10, suggested that this mutation did not effect cell surface expression of ADAM10 (FIG. 15). Treatment of LIM1215 cells with $H_2O_2$ significantly increased 8C7 binding to ADAM10 compared to the control mAb 4A11, while reducing conditions inhibited binding (FIG. 8B). Similarly, stimulation of cells either with EGF to activate the EGF receptor (known to trigger local release of reactive oxygen species (ROS)[45]), or with ephrin-A5 (stimulating EphA receptor signalling), increased binding of 8C7 to ADAM10.

We also found 8C7-bound cells recovered from tumours showed markedly higher production of reactive oxygen species (ROS) compared to unbound (8C7 negative) cells (FIG. 16). Tumours are high in ROS due to elevated RTK and pro-inflammatory signalling, and oxidative stress[53,54]. Interestingly, cancer stem cells (CSCs) are protected from toxic effects conferred by elevated ROS levels by expression of aldehyde dehydrogenase (ALDH), enabling them to maintain high levels of ROS[55]. Indeed, we also find 8C7 particularly targets cells co-staining with the CSC marker CD133 (FIG. 2C), consistent with 8C7 targeting CSCs producing high ROS levels.

Together these observations supported the notion that the preferential binding of 8C7 to the active conformation of ADAM10 may be modulated by disulfide rearrangement within the CXXC motif. We therefore assessed if ADAM10 does contain PDI-modulated cysteines, as recently suggested from MS analysis of labile cysteins in leukocyte cell surface proteins[46]. Following blocking of free cysteines with Methyl-PEG12-maleimide (MPM), 8C7 and 4A11 IPs from LIM1215 lysates were treated first with PDI, followed by Maleimide-PEG2-biotin (MPB) to label the free cysteines that had been generated via PDI activity. Western blot analysis of IPs using anti-ADAM10 antibodies and Streptavidin-HRP to detect cysteine-biotinylated proteins, revealed that PDI caused a marked increase in biotin labelled ADAM10, especially from 8C7 IPs (FIG. 9A), suggesting that similar to ADAM17[44], PDI preferentially acts on the active ADAM10 conformation. We performed the same experiments to also label ADAM10 on intact LIM1215 cells, which had been pre-treated with the PDI inhibitor Bacitracin to limit endogenous PDI activity, and analysed 8C7 or 4A11 IPs from cell lysates by Western blot with Streptavidin-HRP or anti-ADAM10 antibodies to detect cysteine-biotinylated ADAM10. While Bacitracin treatment did not abrogate the presence of labile ADAM10 cysteines, it allowed detecting a moderate but distinct increase in MPB labelling of ADAM10 after PDI treatment (FIG. 9B). Significantly, comparison of Western blot probed with Streptavidin or with anti-ADAM10 antibodies revealed that MPB labelling completely prevented 8C7, but not 4A11, from binding to ADAM10, suggesting that the $C_{594}$-$C_{639}$ interaction located within the 8C7 binding epitope indeed contains a labile cysteine, so that attachment of MPB to the released cysteine or the corresponding change in protein conformation ablated 8C7 binding. We assessed involvement of the $C_{594}HVCC598$ motif in PDI-catalysed disulphide exchange by examining MPM labelling in ADAM10$^{-/-}$ MEFs transfected with Wt or $A_{594}HVA_{597}$ mutant ADAM10. Western blot analysis with Streptavidin-HRP and with anti-ADAM10 antibodies of IPs after serial treatment of cells with MPM, PDI and MPB shows that PDI-induced labelling with MPB is considerably reduced in IPs of mutant $A_{594}HVA_{597}$ ADAM10, strongly implicating this motif in PDI-facilitated disulfide exchange (FIG. 9C).

We then investigated if the 8C7-targeted, active ADAM10 displays distinct protein interactions in cells compared to the overall interactions of ADAM10 bound by the non-selective 4A11 antibody. We used 8C7 and 4A11 immunoprecipitates from LIM1215 cell lysates, equalised for ADAM10 levels by Western blot, and resolved by SDS-PAGE and Coomassie Blue staining. Excised bands of various MW were then analysed by Mass Spectrometry to generate an unbiased comparison of 8C7- and 4A11-co-immunoprecipiated proteins. This revealed some marked differences, including preferential association of 8C7-bound ADAM10 with notch and other ADAM-regulated receptors. We confirmed this by co-immunoprecipitation and Western blot (FIG. 19A, 19B). Notably, 8C7 IPs were also enriched in PDIs, especially PDIA1 (over 50-fold more peptides detected), compared to 4A11 IPs (see also FIG. 19A, 19B). PDIA3, A4 and A6 were also detected. This confirms PDIs are indeed involved in regulating ADAM10 in cells, and that the conformation recognised by 8C7 is preferentially targeted by PDIs, as suggested by biotinylation experiments (FIG. 9A).

Cancer stem-cells maintained by Notch signalling are thought to contribute to tumour chemoresistance, as well as metastasis and epithelial to mesenchymal transition (EMT)[56,57] Since 8C7 particularly targets these cells, as indicated by co-staining with the stem cell marker CD133 and active Notch (NICD) (FIG. 2A-2D), we therefore tested 8C7 treatment of LIM1215 xenografts in combination with irenotecan, a chemotherapeutic used clinically for CRC. Under irenotecan treatment tumours regressed, but relapsed after 6 weeks of injections. However, 8C7 treatment was able to block this relapse, indicating effective inhibition of cells remaining after chemotherapy, with 40% of tumours completely regressing (FIG. 17A, 17B). Staining of CD133+ cells from remaining tumours showed a marked decrease in 8C7-treated mice compared to control (FIG. 17C), consistent with 8C7 treatment targeting chemo-resistant tumour stem cells.

8C7 clearly inhibits signalling by Notch (FIG. 3A-3C), and also Eph receptors[59], however the antibody does not interact directly with residues identified as contributing to substrate binding[60], and indeed we find 8C7 does not inhibit substrate interaction. Rather 8C7-bound ADAM10 preferentially interacts with substrates, including notch and erbB receptors, suggesting the active conformation has a more accessible substrate-binding pocket (FIG. 19A). To understand its possible mechanism of action, in the absence of a full length structure of ADAM10 we compared our 8C7-bound ADAM10 D+C structure with available full-length structures of snake venom proteases, which contain a similar overall M+D+C domain architecture and primary sequence cysteine patterns similar to that of the mammalian ADAMs. Interestingly, the MP domain generally resides within the concave site of the D+C region such that, assuming the mammalian ADAMs have a similar overall architecture, binding of 8C7 to the ADAM10 D+C region would displace the MP domain (FIG. 19B). This provides a potential molecular mechanism for ADAM10 activity inhibition by this antibody.

Lastly, the association of 8C7-bound ADAM10 with erbB receptors lead us to test effects of 8C7 on proliferation of breast cancer cells over-expressing these receptors, in which they drive proliferation. Indeed, 8C7 was able to inhibit proliferation of breast cancer cell lines SKBR3 (high erbB2) and MDA-MB-231 (high EGFR/erbB1), as well as LIM1215 colon cancer cells (FIG. 20).

DISCUSSION

Emerging evidence suggests that ADAM10 and 17 activities may be regulated by adopting latent and active conformations. This suggestion was first based on crystal structures of the related snake venom metalloproteinases, which adopt two different conformations that are stabilized by distinct disulphide connectivity of the D domain[19,20]: a closed, C-shaped conformation seen in Atragin, that positions the active site cleft towards the substrate-binding C domain, suggested to deny substrate access; and an open, I-shaped conformation, exemplified by 'K-like', suggested to allow substrate access and promote cleavage[20]. The ADAM10D+C structure does not correlate directly with either form—while it shows sequence homology with Atragin it has a distinct disulfide bond pattern. However, the C-terminal part of the D domain and the N-terminal part of the C domain of the ADAM10 structure resembles the analogous region of the snake venom ADAM homologue VAP1 (termed the $D_a$ and $C_w$ domains), being super-imposable and having an analogous disulfide pattern[19]. The structure differs however in orientation of the C-terminal part of the C domain (the $C_h$ domain) due to an additional sequence loop and differing disulfide bonds around it, leading to its reversed orientation relative to the $C_w/D_a$ domains. Notably, the distinct disulfide linked Cysteines include the redoxin CxxC motif, which lies directly adjacent to the loop. Thus, while the VAP1 structure is C-shaped, disulfide isomerisation of bonds within the CxxC motif would be expected to alter the conformation, and thus potentially substrate access and cleavage.

Prior evidence that disulfide isomerisation of ADAMs indeed occurs and modulates activity comes from studies on ADAM17, which show that its activity is inhibited by mutation of the analogous CxxC motif, and is regulated by modulating redox conditions[43]. Furthermore, these redox effects were shown to occur through modulation of protein disulfide isomerase (PDI) activity, where PDI modulated both activity of ADAM17 and its recognition by conformation-dependent antibodies[44]. Oxidative conditions were shown to favour activity, and suggested to inhibit PDI from catalysing a shift from an active to an inactive conformation.

We now describe a novel antibody, 8C7, which recognises a specific conformation of the ADAM10 substrate binding domain dependent on CxxC bonding. 8C7 binding is blocked by mutation of the CxxC motif, and is altered by modulating the redox environment. Moreover, biotin-labelling of labile cysteines with Maleimide-PEG2-biotin (MPB) inhibited binding of 8C7, but not a control ADAM10 mAb, suggesting 8C7 indeed binds labile, redox-modulated cysteines. Furthermore, our determination of the structure of 8C7 in complex with ADAM10 shows binding next to C639, disulfide-bonded to C594 in the CxxC motif. Our evidence suggests the 8C7-recognised conformation is active, since 8C7-immunoprecipitates of ADAM10 showed highly significant enrichment of protease activity. Also, oxidative conditions, known to enhance ADAM activity, favoured 8C7 binding. Experiments are underway to define the disulfide bonding pattern and structure of the presumed alternate, inactive ADAM10 C domain conformation. Interestingly, a recent NMR study shows two distinct, PDI-regulated conformations of bacterially expressed ADAM17, with distinct CxxC linkages, supporting the notion of CxxC isomerisation, although the activities of the two forms or their relevance for mammalian-expressed ADAM17 was not assessed[47]. The analogous changes in ADAM10 would correspond to the $C_{594}$-$C_{639}$ linkage in our 8C7-bound structure swapping to $C_{594}$-$C_{632}$, accommodated by a further change from $C_{632}$-$C_{645}$ to $C_{639}$-$C_{645}$.

Importantly, the apparent selectivity of 8C7 for active ADAM10 translates to selectivity for ADAM10 in tumours compared to other, normal tissues in both mouse models (CRC xenograft model and the GP130FF model of spontaneous gastric tumour formation), and in human tumour samples. This suggests 8C7 as a potentially powerful diagnostic for ADAM10 activity in tumours. Interestingly the 8C7-recognised form of ADAM10 that was specific to tumours was largely a HMW, unprocessed form, which we confirmed is present on the cell surface and is cleavable by furin. While the ADAM10 Pro domain is known to have an inhibitory function, it also has an essential chaperone function[41], and ADAM10 Pro domain mutations which likely disrupt this function have recently been shown to attenuate ADAM10 activity in late onset Alzheimer's disease[48]. Moreover, reversible activation of unprocessed ADAM17 has recently been demonstrated[42]. Therefore, it is likely the unprocessed ADAM10 prevalent in tumours is similarly readily activated, and the high level of 8C7 binding indicates a high degree of activity in tumours. This activity is most likely supported by high levels of ROS in the tumour microenvironment[49], favouring the active ADAM10 isomer.

As well as preferentially targeting tumours 8C7, significantly inhibited tumour growth. We previously found 8C7 inhibited ADAM10 mediated shedding of the Eph receptor ligand ephrin-A5, thus attenuating Eph receptor tyrosine phosphorylation and Eph-mediated cell segregation[22]. This is consistent with its targeting the substrate binding domain, which we previously showed is necessary for ephrin cleavage[6]. While the LIM1215 tumours expressed high levels of EphA2 we could not detect phosphorylation, consistent with known Eph kinase-independent function in tumours[50-52], so a direct effect on Eph activity in tumours was not detectable. Rather we noted a dramatic down-regulation of EphA2 expression, and also of Notch receptors. A role for ADAM10 in Notch signalling is well established, and since Notch acts to modulate transcription of a variety of targets, including Eph receptors/ligands and Notch itself, we investigated effects of 8C7 on Notch activity. Treatment of tumour-bearing mice inhibited production of the cleaved active NICD in tumours, and there was also significant down-regulation of Notch-induced target genes (Hes1, Hey1). There was also decreased vascularity of 8C7-treated tumours consistent with inhibited Notch signalling. Treatment of isolated tumour cells also inhibited Notch activity, suggesting a direct effect on Notch. We further tested 8C7 in a separate in vitro assay of Notch-dependent lymphoma cell survival and proliferation, which confirmed a marked inhibition indicative of attenuated Notch signalling. Thus, 8C7-inhibition of tumour growth appears to be at least partially due to inhibition of Notch activity, although effects on other ADAM10-targets are also being investigated.

Notably, while 8C7 bound to the tumour mass, it was clearly most strongly bound to a distinct population of cells within tumours which were closely associated with blood vessels, and which expressed the putative tumour stem cell marker CD133. A recent study has described CD133+ cells in perivascular regions of human CRC, which display elevated Notch signalling due to ADAM17-mediated release of the ligand Jagged-1 from the endothelial cells[30]. In agreement we find 8C7-targeted CD133+ cells show high levels of NICD1 and 2, both by immunofluorescence staining of tumours and by analysis of CD133+ sorted cells by Western blot. Treatment of these cells in vitro with 8C7 also inhibited Notch activity and down-regulated Notch target genes. This suggests that 8C7 inhibition of ADAM10 activity is particularly acting on a subpopulation of tumour cells previously identified as having a stem cell phenotype. Since stem cells are believed to initiate and sustain tumour growth, and to mediate chemoresistance due to their slow cycling, the specific targeting of this population by 8C7, and its inhibitory effects on tumour growth, combined with its selectivity for active conformation of ADAM10 in tumours, indicate considerable potential for therapy. In support, we find 8C7 effectively blocks tumour regrowth following chemotherapy, and specifically depletes CD133+ cells.

Humanised Versions of Anti-ADAM10 mAb 8C7 and Effects on erbB Receptor Over-Expressing Breast Cancer Cells We have produced a human and mouse chimerised version of mAb 8C7 (ch8C7), which retains the antigen-binding variable regions from murine 8C7 in a human IgG1-κ light and heavy constant region framework, and demonstrated identical binding of mu8C7 and ch8C7 to immobilised recombinant huADAM10D+C domain protein (see FIG. 21). Stable cell lines expressing ch8C7 in CHO-GS cells were generated using the Glutamine synthetase (GS) protein expression system (Lonza), an approach tailored for antibody production that relies on endogenous GS inhibition by methionine sulphoximine (MSX) to select for transfectants with exogenous GS activity.

We also engineered a fully 'humanised' version of 8C7 (hu8C7), as human IgG1-κ subtype, due to its capacity for preferential activation of FcγRIII receptors on phagocytes eliciting antibody-dependent cellular cytotoxicity (ADCC). Homology modelling was used to identify human heavy chain and light chain variable region sequences closest to antibody germline sequences (SEQ ID NOS:3 and 4; FIG. 25). The encoding nucleotide sequences are shown in FIG. 26 (SEQ ID NOS:5 and 6). An amino acid sequence lineup comparing SEQ ID NO:1 with SEQ ID NO:3 and SEQ ID NO:2 with SEQ ID NO:4 is shown in FIG. 25. Nucleotide sequences encoding the humanised variable heavy chain and light chain domains (SEQ ID NOS:5 and 6) were cloned into pEE14.4 ch8C7 LC and pEE6.4 ch8C7 HC chimeric constructs (Lonza GS expression system), replacing the murine variable domains.

The human immunoglobulin IgG1-κ light and heavy constant region sequences used to produce hu8C7 with ch8C7 are shown in FIGS. 27A-27B (SEQ ID NOS:7 and 8) and have been previously described in Ref. 66.

We compared binding and activity of hu8C7 with ch8C7, which shares the same Fc region as hu8C7, allowing unbiased comparison of binding to ADAM10 in cells and cell lysates using identical Fc-binding reagents. Binding affinity measurements of hu8C7 to immobilised recombinant huADAM10D+C protein were comparable to ch8C7 (FIG. 21; Table 3). Also, binding to ADAM10 in cell lysates of LIM1215 colorectal cancer cells (endogenously expressing ADAM10) was indistinguishable (FIG. 22). To test binding to the ADAM10 extracellular domain in live cells we transfected HEK293 cells with huADAM10 lacking the metalloprotease domain (pDisplay-ADAM10D+C), which we proposed sterically competes with 8C7 binding to the ADAM10 C (cysteine-rich) domain in the inactive (resting) state, underlying its selectivity for active ADAM10 [61, 62]. Consistent with this notion, all versions of 8C7 show strong binding to ADAM10D+C expressed on HEK293 cells (FIG. 23), but not to endogenous full-length ADAM10 on untransfected cells (FIG. 23), which a control ADAM10 antibody clearly binds. The similarity of binding of mu8C7, ch8C7 and hu8C7 indicates identical conformational selectivity for ADAM10.

Finally, we tested effects of our antibodies on HER/erbB receptor over-expressing breast cancer cells. ADAM10 is known to mediate erbB2 shedding, implicated in constitutive signalling, proliferation and Herceptin resistance [63, 64]. We have found that 8C7 treatment is able to inhibit constitutive shedding of the extracellular domain of erbB2 into cell-conditioned medium, and also unexpectedly of the erbB1/EGF receptor (FIG. 24A). We then tested effects of ch8C7 and hu8C7 on proliferation and viability, and the data in FIG. 24B showed both antibodies caused similar inhibition of viability or erbB2 amplified BT474 breast cancer cells, comparable to treatment with the anti-erbB2 antibody Herceptin (Trastuzumab).

Throughout this specification, the aim has been to describe the preferred embodiments of the invention without limiting the invention to any one embodiment or specific collection of features. Various changes and modifications may be made to the embodiments described and illustrated herein without departing from the broad spirit and scope of the invention.

All computer programs, algorithms, patent and scientific literature referred to herein is incorporated herein by reference in their entirety.

REFERENCES

1 Murphy, G. The ADAMs: signalling scissors in the tumour microenvironment. *Nat Rev Cancer* (2008) 8, 929-941
2 Mochizuki, S et al. ADAMs in cancer cell proliferation and progression. *Cancer Sci* (2007) 98, 621-628
3 Hartmann, M et al. Who decides when to cleave an ectodomain? *Trends Biochem Sci* (2013) 38, 111-120
4 Saftig, P et al. The "A Disintegrin And Metalloproteases" ADAM10 and ADAM17: novel drug targets with therapeutic potential? *Eur J Cell Biol* (2011) 90, 527-535
5 Hartmann, D et al. The disintegrin/metalloprotease ADAM 10 is essential for Notch signalling but not for alpha-secretase activity in fibroblasts. *Hum Mol Genet* (2002) 11, 2615-2624
6 Janes, P W et al. Adam Meets Eph: An ADAM Substrate Recognition Module Acts as a Molecular Switch for Ephrin Cleavage In trans. *Cell* (2005) 123, 291-304
7 Hattori, M et al. Regulated cleavage of a contact-mediated axon repellent. *Science* (2000) 289, 1360-1365
8 Sahin, U et al. Distinct roles for ADAM10 and ADAM17 in ectodomain shedding of six EGFR ligands. *J Cell Biol* (2004) 164, 769-779
9 Reiss, K et al. ADAM10 cleavage of N-cadherin and regulation of cell-cell adhesion and beta-catenin nuclear signalling. *EMBO J* (2005) 24, 742-752
10 LaVoie, M J et al. The Notch Ligands, Jagged and Delta, Are Sequentially Processed by α-Secretase and Presenilin/γ-Secretase and Release Signaling Fragments. *Journal of Biological Chemistry* (2003) 278, 34427-34437
11 Kopan, R et al. The Canonical Notch Signaling Pathway: Unfolding the Activation Mechanism. *Cell* (2009) 137, 216-233
12 Ranganathan, P et al. Notch signalling in solid tumours: a little bit of everything but not all the time. *Nat Rev Cancer* (2011) 11, 338-351
13 Roca, C et al. Regulation of vascular morphogenesis by Notch signaling. *Genes Dev* (2007) 21, 2511-2524
14 Groth, C et al. Therapeutic approaches to modulating Notch signaling: Current challenges and future prospects. *Semin Cell Dev Biol* (2012)
15 Dikic, I et al. Notch: Implications of endogenous inhibitors for therapy. *Bioessays* (2010) 32, 481-487
16 DasGupta, S et al. Current perspective of TACE inhibitors: A review. *Bioorganic & Medicinal Chemistry* (2009) 17, 444-459
17 Smith, K M et al. The cysteine-rich domain regulates ADAM protease function in vivo. *J. Cell Biol.* (2002) 159, 893-902
18 Janes, P W et al. Cytoplasmic relaxation of active Eph controls ephrin shedding by ADAM10. *PLoS Biol* (2009) 7, e1000215
19 Takeda, S et al. Crystal structures of VAP1 reveal ADAMs' MDC domain architecture and its unique C-shaped scaffold. *EMBO J* (2006) 25, 2388-2396
20 Guan, H-H et al. Structures of two elapid snake venom metalloproteases with distinct activities highlight the disulfide patterns in the D domain of ADAMalysin family proteins. *Journal of structural biology* (2010) 169, 294-303
21 Takeda, S. Three-dimensional domain architecture of the ADAM family proteinases. *Semin Cell Dev Biol* (2009) 20, 146-152
22 Benham, A M. The protein disulfide isomerase family: key players in health and disease. *Antioxid Redox Signal* (2012) 16, 781-789
23 Wang, Y et al. Regulation of mature ADAM17 by redox agents for L-selectin shedding. *J Immunol* (2009) 182, 2449-2457
24 Willems, S H et al. Thiol isomerases negatively regulate the cellular shedding activity of ADAM17. *Biochem J* (2010) 428, 439-450
25 Fischer, O M et al. EGFR signal transactivation in cancer cells. *Biochem Soc Trans* (2003) 31, 1203-1208

26 Seals, D F et al. The ADAMs family of metalloproteases: multidomain proteins with multiple functions. *Genes Dev* (2003) 17, 7-30

27 Atapattu, L et al. Antibodies binding the ADAM10 substrate recognition domain inhibit Eph function. *J Cell Sci* (2012) 125, 6084-6093

28 Sikandar, S S et al. NOTCH signaling is required for formation and self-renewal of tumor-initiating cells and for repression of secretory cell differentiation in colon cancer. Cancer Res (2010) 70, 1469-1478

29 van Es, J H et al. Notch/gamma-secretase inhibition turns proliferative cells in intestinal crypts and adenomas into goblet cells. *Nature* (2005) 435, 959-963

30 Lu, J et al. Endothelial cells promote the colorectal cancer stem cell phenotype through a soluble form of Jagged-1. *Cancer Cell* (2013) 23, 171-185

31 Guilmeau, S et al. Heterogeneity of Jagged1 expression in human and mouse intestinal tumors: implications for targeting Notch signaling. *Oncogene* (2009) 29, 992-1002

32 Yuan, Z et al. An A13 Repeat within the 3'-Untranslated Region of Epidermal Growth Factor Receptor (EGFR) Is Frequently Mutated in Microsatellite Instability Colon Cancers and Is Associated with Increased EGFR Expression. *Cancer Research* (2009) 69, 7811-7818

33 Bray, S et al. Notch targets and their regulation. *Curr Top Dev Biol* (2010) 92, 253-275

34 Baumgart, A et al. ADAM17 Regulates Epidermal Growth Factor Receptor Expression through the Activation of Notch1 in Non-Small Cell Lung Cancer. *Cancer Research* (2010) 70, 5368-5378

35 Hainaud, P et al. The Role of the Vascular Endothelial Growth Factor-Delta-like 4 Ligand/Notch4-Ephrin B2 Cascade in Tumor Vessel Remodeling and Endothelial Cell Functions. *Cancer Research* (2006) 66, 8501-8510

36 Zhong, T P et al. Gridlock signalling pathway fashions the first embryonic artery. *Nature* (2001) 414, 216-220

37 Butler, J M et al. Endothelial cells are essential for the self-renewal and repopulation of Notch-dependent hematopoietic stem cells. *Cell Stem Cell* (2010) 6, 251-264

38 Ernst, M et al. STAT3 and STAT1 mediate IL-11-dependent and inflammation-associated gastric tumorigenesis in gp130 receptor mutant mice. *J Clin Invest* (2008) 118, 1727-1738

39 Tebbutt, N C et al. Reciprocal regulation of gastrointestinal homeostasis by SHP2 and STAT-mediated trefoil gene activation in gp130 mutant mice. *Nat Med* (2002) 8, 1089-1097

40 Edwards, D R et al. The ADAM metalloproteinases. *Molecular Aspects of Medicine* (2008) 29, 258-289

41 Anders, A et al. Regulation of the alpha-secretase ADAM10 by its prodomain and proprotein convertases. *Faseb J* (2001) 15, 1837-1839

42 Le Gall, S M et al. ADAM17 is regulated by a rapid and reversible mechanism that controls access to its catalytic site. *J Cell Sci* (2010) 123, 3913-3922

43 Miao, H et al. EphA2 mediates ligand-dependent inhibition and ligand-independent promotion of cell migration and invasion via a reciprocal regulatory loop with Akt. *Cancer Cell* (2009) 16, 9-20

44 Bass, R et al. ADAMs and protein disulfide isomerase: the key to regulated cell-surface protein ectodomain shedding? *Biochem J* (2010) 428, e3-5

45 Finkel, T. From sulfenylation to sulfhydration: what a thiolate needs to tolerate. *Science signaling* (2012) 5, pe10

46 Metcalfe, C et al. Labile disulfide bonds are common at the leucocyte cell surface. *Open Biol* (2011) 1, 110010

47 Dusterhoft, S et al. Membrane-proximal domain of a disintegrin and metalloprotease-17 represents the putative molecular switch of its shedding activity operated by protein-disulfide isomerase. *J Am Chem Soc* (2013) 135, 5776-5781

48 Suh, J et al. ADAM10 Missense Mutations Potentiate β-Amyloid Accumulation by Impairing Prodomain Chaperone Function. *Neuron* (2013) 80, 385-401

49 Benz, C C et al. Ageing, oxidative stress and cancer: paradigms in parallax. *Nat Rev Cancer* (2008) 8, 875-879

50 Pasquale, E. Eph receptors and ephrins in cancer: bidirectional signalling and beyond. *Nature Reviews Cancer* (2010) 10, 165-180

51 Nievergall, E et al. PTP1B regulates Eph receptor function and trafficking. *J Cell Biol* (2010) 191, 1189-1203

52 Boyd, A W et al. Therapeutic targeting of EPH receptors and their ligands. *Nat Rev Drug Discov* (2013) 13, 39-62

53. Fiaschi, T et al. Oxidative Stress, Tumor Microenvironment, and Metabolic Reprogramming: A Diabolic Liaison. *International Journal of Cell Biology* (2012) 2012, 8

54. Schieber, M et al. ROS Function in Redox Signaling and Oxidative Stress. *Current Biology* (2014) 24, R453-R462

55. Raha, D et al. The cancer stem cell marker aldehyde dehydrogenase is required to maintain a drug-tolerant tumor cell subpopulation. *Cancer research* (2014) 74, 3579-3590

56. Espinoza, I et al. Notch signaling: targeting cancer stem cells and epithelial-to-mesenchymal transition. *OncoTargets and therapy* (2013) 6, 1249-1259

57. Giancotti, Filippo G. Mechanisms Governing Metastatic Dormancy and Reactivation. *Cell* (2013) 155, 750-764

58. Batlle, E et al. Molecular Mechanisms of Cell Segregation and Boundary Formation in Development and Tumorigenesis. *Cold Spring Harbor Perspectives in Biology* (2012) 4

59. Atapattu, L et al. Antibodies binding the ADAM10 substrate recognition domain inhibit Eph function. *J Cell Sci* (2012)

60. Janes, P W et al. Adam Meets Eph: An ADAM Substrate Recognition Module Acts as a Molecular Switch for Ephrin Cleavage In trans. *Cell* (2005) 123, 291-304

61. Atapattu, L., et al., *An activated form of ADAM10 is tumor selective and regulates cancer stem-like cells and tumor growth*. Journal of Experimental Medicine, 2016. 213(9): p. 1741-1757.

62. Seegar, T. C. M., et al., *Structural Basis for Regulated Proteolysis by the alpha-Secretase ADAM10*. Cell, 2017.

63. Liu, P. C., et al., *Identification of ADAM10 as a major source of HER2 ectodomain sheddase activity in HER2 overexpressing breast cancer cells*. Cancer Biol Ther, 2006. 5(6): p. 657-64.

64. Feldinger, K., et al., *ADAM10 mediates trastuzumab resistance and is correlated with survival in HER2 positive breast cancer*. Oncotarget, 2014. 5(16): p. 6633-46.

65. Lackmann, M., et al., *Purification of a ligand for the EPH-like receptor HEK using a biosensor-based affinity detection approach*. Proc. Natl. Acad. Sci. U.S.A, 1996. 93(6): p. 2523-2527.

66. Panoussis, C et al., *Engineering and characterization of chimeric monoclonal antibody 806 (ch806) for targeted immunotherapy of tumours expressing de2-7 EGFR or amplified EGFR*. British J. Cancer, 2005. 92 1069-1077.

TABLE 1

Data collection and refinement statistics: crystal structure of the complex between ADAM10 D + C-domain and 8C7 F(Ab)$_2$.

| Adam/mAb | |
|---|---|
| Wavelength (Å) | 0.9792 |
| Resolution range (Å) | 141.7-2.76 (2.91-2.76) |
| Space group | P 21 21 21 |
| Unit cell | 53.326 141.679 268.08 90 90 90 |
| Total reflections | 234255 |
| Unique reflections | 52800 |
| Multiplicity | 4.4 (4.4) |
| Completeness (%) | 98.63 (97.87) |
| Mean I/sigma(I) | 10.32 (2.10) |
| Wilson B-factor | 41.90 |
| R-merge | 0.125 (0.675) |
| R-work | 0.2028 (0.3273) |
| R-free | 0.2514 (0.3677) |
| Number of atoms | 9942 |
| macromolecules | 9485 |
| ligands | 123 |
| water | 334 |
| Protein residues | 1252 |
| RMS (bonds) | 0.009 |
| RMS (angles) | 1.26 |
| Ramachandran favored (%) | 98 |
| Ramachandran outliers (%) | 0 |
| Clashscore | 7.55 |
| Average B-factor | 32.60 |
| macromolecules | 32.60 |
| ligands | 52.60 |
| solvent | 27.30 |

Statistics for the highest-resolution shell are shown in parentheses.

TABLE 2

Residue contacts in the complex between ADAM10 D + C-domain and 8C7 F(Ab)$_2$.

Adam/Light Chain
Non-bonded contacts

| | Atom no. | Atom name | Res name | Res no. | Chain | | Atom no. | Atom name | Res name | Res no. | Chain | Distance |
|---|---|---|---|---|---|---|---|---|---|---|---|---|
| 1. | 12 | CB | VAL | 451 | A | <--> | 2056 | CD1 | ILE | 72 | B | 3.72 |
| 2. | 13 | CG1 | VAL | 451 | A | <--> | 2054 | CG1 | ILE | 72 | B | 3.87 |
| 3. | 13 | CG1 | VAL | 451 | A | <--> | 2056 | CD1 | ILE | 72 | B | 3.58 |
| 4. | 14 | CG2 | VAL | 451 | A | <--> | 2032 | C | ASP | 70 | B | 3.80 |
| 5. | 14 | CG2 | VAL | 451 | A | <--> | 2033 | O | ASP | 70 | B | 3.62 |
| 6. | 14 | CG2 | VAL | 451 | A | <--> | 2056 | CD1 | ILE | 72 | B | 3.79 |
| 7. | 782 | CZ | ARG | 557 | A | <--> | 2220 | CD | ARG | 93 | B | 3.73 |
| 8. | 782 | CZ | ARG | 557 | A | <--> | 2223 | NH1 | ARG | 93 | B | 3.70 |
| 9. | 783 | NH1 | ARG | 557 | A | <--> | 2223 | NH1 | ARG | 93 | B | 3.60 |
| 10. | 784 | NH2 | ARG | 557 | A | <--> | 2220 | CD | ARG | 93 | B | 3.16 |
| 11. | 1410 | O | VAL | 641 | A | <--> | 2231 | CD1 | TRP | 94 | B | 3.11 |
| 12. | 1410 | O | VAL | 641 | A | <--> | 2233 | NE1 | TRP | 94 | B | 3.41 |
| 13. | 1412 | CG1 | VAL | 641 | A | <--> | 2203 | O | SER | 91 | B | 3.26 |
| 14. | 1412 | CG1 | VAL | 641 | A | <--> | 2208 | C | ASN | 92 | B | 3.82 |
| 15. | 1412 | CG1 | VAL | 641 | A | <--> | 2209 | O | ASN | 92 | B | 3.32 |
| 16. | 1420 | CD1 | PHE | 642 | A | <--> | 2231 | CD1 | TRP | 94 | B | 3.70 |
| 17. | 1424 | CZ | PHE | 642 | A | <--> | 2255 | CE2 | PHE | 96 | B | 3.84 |
| 18. | 1424 | CZ | PHE | 642 | A | <--> | 2256 | CZ | PHE | 96 | B | 3.84 |

Number of non-bonded contacts: 18

Adam/Heavy Chain
Hydrogen bonds

| | ATOM1 | | | | | | ATOM2 | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 1405 | OD2 | ASP | 640 | A | <--> | 3979 | OH | TYR | 105 | C | 3.07 |
| 2. | 1407 | N | VAL | 641 | A | <--> | 3951 | O | LEU | 103 | C | 3.27 |
| 3. | 1442 | NH1 | ARG | 644 | A | <--> | 3590 | OD1 | ASP | 55 | C | 3.27 |
| 4. | 1442 | NH1 | ARG | 644 | A | <--> | 3602 | OD2 | ASP | 57 | C | 2.83 |
| 5. | 1443 | NH2 | ARG | 644 | A | <--> | 3589 | OD2 | ASP | 55 | C | 2.42 |
| 6. | 1459 | NH1 | ARG | 646 | A | <--> | 3979 | OH | TYR | 105 | C | 2.86 |
| 7. | 1460 | NH2 | ARG | 646 | A | <--> | 3375 | O | ASN | 31 | C | 3.26 |

Non-bonded contacts

| | ATOM1 | | | | | | ATOM2 | | | | | |
|---|---|---|---|---|---|---|---|---|---|---|---|---|
| | Atom no. | Atom name | Res name | Res no. | Chain | | Atom no. | Atom name | Res name | Res no. | Chain | Distance |
| 1. | 1009 | OD2 | ASP | 589 | A | <--> | 3581 | NH1 | ARG | 54 | C | 3.70 |
| 2. | 1024 | CG | LYS | 591 | A | <--> | 3602 | OD2 | ASP | 57 | C | 3.82 |
| 3. | 1025 | CD | LYS | 591 | A | <--> | 3602 | OD2 | ASP | 57 | C | 3.67 |
| 4. | 1026 | CE | LYS | 591 | A | <--> | 3602 | OD2 | ASP | 57 | C | 3.79 |

TABLE 2-continued

Residue contacts in the complex between ADAM10 D + C-domain and 8C7 F(Ab)$_2$.

| | | | | | | | | | |
|---|---|---|---|---|---|---|---|---|---|
| 5. | 1027 NZ | LYS | 591 | A <--> | 3601 OD1 | ASP | 57 | C | 3.73 |
| 6. | 1311 C | PRO | 628 | A <--> | 3967 OH | TYR | 104 | C | 3.57 |
| 7. | 1312 O | PRO | 628 | A <--> | 3967 OH | TYR | 104 | C | 3.46 |
| 8. | 1313 CB | PRO | 628 | A <--> | 3964 CE2 | TYR | 104 | C | 3.59 |
| 9. | 1313 CB | PRO | 628 | A <--> | 3966 CZ | TYR | 104 | C | 3.76 |
| 10. | 1313 CB | PRO | 628 | A <--> | 3967 OH | TYR | 104 | C | 3.34 |
| 11. | 1385 CB | TYR | 638 | A <--> | 3954 CD1 | LEU | 103 | C | 3.79 |
| 12. | 1385 CB | TYR | 638 | A <--> | 3955 CD2 | LEU | 103 | C | 3.89 |
| 13. | 1396 O | CYS | 639 | A <--> | 3954 CD1 | LEU | 103 | C | 3.76 |
| 14. | 1400 CA | ASP | 640 | A <--> | 3951 O | LEU | 103 | C | 3.67 |
| 15. | 1400 CA | ASP | 640 | A <--> | 3952 CB | LEU | 103 | C | 3.76 |
| 16. | 1403 CB | ASP | 640 | A <--> | 3951 O | LEU | 103 | C | 3.36 |
| 17. | 1403 CB | ASP | 640 | A <--> | 3977 CE2 | TYR | 105 | C | 3.76 |
| 18. | 1403 CB | ASP | 640 | A <--> | 3979 OH | TYR | 105 | C | 3.50 |
| 19. | 1404 CG | ASP | 640 | A <--> | 3979 OH | TYR | 105 | C | 3.62 |
| 20. | 1405 OD2 | ASP | 640 | A <--> | 3979 OH | TYR | 105 | C | 3.07 |
| 21. | 1407 N | VAL | 641 | A <--> | 3951 O | LEU | 103 | C | 3.27 |
| 22. | 1412 CG1 | VAL | 641 | A <--> | 3962 CD2 | TYR | 104 | C | 3.57 |
| 23. | 1413 CG2 | VAL | 641 | A <--> | 3951 O | LEU | 103 | C | 3.02 |
| 24. | 1413 CG2 | VAL | 641 | A <--> | 3957 CA | TYR | 104 | C | 3.64 |
| 25. | 1417 O | PHE | 642 | A <--> | 3615 CE | LYS | 59 | C | 3.22 |
| 26. | 1417 O | PHE | 642 | A <--> | 3616 NZ | LYS | 59 | C | 3.47 |
| 27. | 1418 CB | PHE | 642 | A <--> | 3401 CE2 | TRP | 33 | C | 3.67 |
| 28. | 1418 CB | PHE | 642 | A <--> | 3403 CZ2 | TRP | 33 | C | 3.46 |
| 29. | 1419 CG | PHE | 642 | A <--> | 3401 CE2 | TRP | 33 | C | 3.90 |
| 30. | 1421 CD2 | PHE | 642 | A <--> | 3397 CG | TRP | 33 | C | 3.61 |
| 31. | 1421 CD2 | PHE | 642 | A <--> | 3398 CD1 | TRP | 33 | C | 3.79 |
| 32. | 1421 CD2 | PHE | 642 | A <--> | 3399 CD2 | TRP | 33 | C | 3.50 |
| 33. | 1421 CD2 | PHE | 642 | A <--> | 3400 NE1 | TRP | 33 | C | 3.83 |
| 34. | 1421 CD2 | PHE | 642 | A <--> | 3401 CE2 | TRP | 33 | C | 3.65 |
| 35. | 1423 CE2 | PHE | 642 | A <--> | 3397 CG | TRP | 33 | C | 3.90 |
| 36. | 1423 CE2 | PHE | 642 | A <--> | 3975 CD2 | TYR | 105 | C | 3.86 |
| 37. | 1424 CZ | PHE | 642 | A <--> | 3421 OE1 | GLN | 35 | C | 3.83 |
| 38. | 1438 CG | ARG | 644 | A <--> | 3403 CZ2 | TRP | 33 | C | 3.42 |
| 39. | 1439 CD | ARG | 644 | A <--> | 3602 OD2 | ASP | 57 | C | 3.77 |
| 40. | 1441 CZ | ARG | 644 | A <--> | 3559 CD2 | TYR | 52 | C | 3.71 |
| 41. | 1441 CZ | ARG | 644 | A <--> | 3561 CE2 | TYR | 52 | C | 3.88 |
| 42. | 1441 CZ | ARG | 644 | A <--> | 3589 OD2 | ASP | 55 | C | 3.15 |
| 43. | 1442 NH1 | ARG | 644 | A <--> | 3559 CD2 | TYR | 52 | C | 3.53 |
| 44. | 1442 NH1 | ARG | 644 | A <--> | 3588 CG | ASP | 55 | C | 3.56 |
| 45. | 1442 NH1 | ARG | 644 | A <--> | 3590 OD1 | ASP | 55 | C | 3.27 |
| 46. | 1442 NH1 | ARG | 644 | A <--> | 3589 OD2 | ASP | 55 | C | 3.09 |
| 47. | 1442 NH1 | ARG | 644 | A <--> | 3599 CB | ASP | 57 | C | 3.24 |
| 48. | 1442 NH1 | ARG | 644 | A <--> | 3600 CG | ASP | 57 | C | 3.47 |
| 49. | 1442 NH1 | ARG | 644 | A <--> | 3602 OD2 | ASP | 57 | C | 2.83 |
| 50. | 1443 NH2 | ARG | 644 | A <--> | 3559 CD2 | TYR | 52 | C | 3.87 |
| 51. | 1443 NH2 | ARG | 644 | A <--> | 3561 CE2 | TYR | 52 | C | 3.79 |
| 52. | 1443 NH2 | ARG | 644 | A <--> | 3588 CG | ASP | 55 | C | 3.47 |
| 53. | 1443 NH2 | ARG | 644 | A <--> | 3590 OD1 | ASP | 55 | C | 3.87 |
| 54. | 1443 NH2 | ARG | 644 | A <--> | 3589 OD2 | ASP | 55 | C | 2.42 |
| 55. | 1455 CG | ARG | 646 | A <--> | 3979 OH | TYR | 105 | C | 3.53 |
| 56. | 1456 CD | ARG | 646 | A <--> | 3979 OH | TYR | 105 | C | 3.66 |
| 57. | 1457 NE | ARG | 646 | A <--> | 3564 OH | TYR | 52 | C | 3.90 |
| 58. | 1458 CZ | ARG | 646 | A <--> | 3564 OH | TYR | 52 | C | 3.80 |
| 59. | 1459 NH1 | ARG | 646 | A <--> | 3978 CZ | TYR | 105 | C | 3.81 |
| 60. | 1459 NH1 | ARG | 646 | A <--> | 3979 OH | TYR | 105 | C | 2.86 |
| 61. | 1460 NH2 | ARG | 646 | A <--> | 3375 O | ASN | 31 | C | 3.26 |
| 62. | 1460 NH2 | ARG | 646 | A <--> | 3564 OH | TYR | 52 | C | 3.7062 |

Number of hydrogen bonds: 7
Number of non-bonded contacts:

TABLE 3

Binding affinity measurement of hu and ch8C7 binding to immobilised recombinant huADAM10D + C protein.

| | $K_D$ (nM) | $k_a$ (1/Ms) | $k_d$ (1/s) |
|---|---|---|---|
| ch8C7 | 6.71 | 1.57E+05 | 1.05E−03 |
| hu8C7 | 7.33 | 1.66E+05 | 1.22E−03 |

Analysis of protein interactions by surface plasmon resonance was carried out on a BIAcore 3000 biosensor (BIAcore) as described previously [5].
$K_D$, equilibrium dissociation constant;
$k_a$, association rate constant;
$k_d$, dissociation rate constant.

---

The invention claimed is:

1. A recombinant, humanized antibody or antibody fragment comprising a heavy chain variable region polypeptide and a light chain variable region polypeptide, wherein the heavy chain variable region polypeptide comprises complementarity determining region (CDR) 1, 2, and 3 (HCDR1, HCDR2, and HCDR3) amino acid sequences GYTFTNYWLQ (SEQ ID NO: 13), AIYPRDGDAKYSQKFKD (SEQ ID NO: 14), and ANYGLYYAMDR (SEQ ID NO: 15) respectively, and wherein the light chain variable region polypeptide comprises CDR 1, 2, and 3 (LCDR1, LCDR2, and LCDR3) amino acid sequences RASQNIGTNIH (SEQ ID NO: 16), YASESIS (SEQ ID NO: 17), and QQSNRWPFT (SEQ ID NO: 18) respectively.

2. The recombinant, humanized antibody or antibody fragment of claim 1, further comprising one or more human immunoglobulin Fc and/or constant region amino acid sequences.

3. The recombinant, humanized antibody or antibody fragment of claim 2, wherein the one or more human immunoglobulin Fc and/or constant region amino acid sequences are set forth in SEQ ID NO: 7 and/or SEQ ID NO: 8, or an amino acid sequence at least 80% identical thereto.

4. The recombinant humanized antibody or antibody fragment of claim 1, which specifically, selectively or preferentially binds a proteolytically active form of an ADAM10 protease.

5. The recombinant, humanized antibody or antibody fragment of claim 4, which binds a region, portion and/or amino acid sequence of an ADAM10 protease that provides a switch between a proteolytically active and inactive form of an ADAM10 protease.

6. The recombinant humanized antibody or antibody fragment of claim 5, which region, portion or the amino acid sequence of the ADAM10 protease is of a loop which preferably comprises a disulphide bond between a cysteine residue and an adjacent CXXC motif.

7. The recombinant humanized antibody or antibody fragment of claim 6, wherein the loop comprises two intramolecular disulfide bonds: $C_{594}$-$C_{639}$ and $C_{632}$-$C_{645}$.

8. The recombinant humanized antibody or antibody fragment of claim 1, wherein the antibody or antibody fragment binds or interacts with one or more ADAM10 protease residues selected from the group consisting of: $Arg_{557}$, $Lys_{591}$, $Pro_{628}$, $Asp_{640}$, $Val_{641}$, $Phe_{642}$, $Arg_{644}$, and $Arg_{646}$.

9. The recombinant humanized antibody or antibody fragment of claim 8, wherein hydrogen bonds are formed between $Asp_{640}$, $Val_{641}$, $Phe_{642}$, $Arg_{644}$, and $Arg_{646}$, and the antibody or antibody fragment.

10. A kit comprising the recombinant humanized antibody or antibody fragment of claim 1, and one or more reaction vessels.

11. The recombinant, humanized antibody or antibody fragment of claim 1, wherein (i) the heavy chain variable region polypeptide comprises an amino acid sequence that is at least 90% identical to the amino acid sequence set forth in SEQ ID NO: 1 or SEQ ID NO: 3, and (ii) the light chain variable region polypeptide comprises an amino acid sequence that is at least 90% identical to the amino acid sequence set forth in SEQ ID NO: 2 or SEQ ID NO: 4.

12. The recombinant, humanized antibody or antibody fragment of claim 1, wherein (i) the heavy chain variable region polypeptide comprises the amino acid sequence set forth in SEQ ID NO: 1 and the light chain variable region polypeptide comprises the amino acid sequence set forth in SEQ ID NO: 2, or (ii) the heavy chain variable region polypeptide comprises the amino acid sequence set forth in SEQ ID NO: 3 and the light chain variable region polypeptide comprises the amino acid sequence set forth in SEQ ID NO: 4.

13. A method of detecting a proteolytically active form of an ADAM10 protease, said method including the step of contacting the recombinant humanized antibody or antibody fragment of claim 1 to a proteolytically active form of an ADAM10 protease to thereby detect the proteolytically active form of the ADAM10 protease.

14. A method of detecting a tumour cell expressing a proteolytically active form of an ADAM10 protease, said method comprising contacting the tumour cell with the recombinant humanized antibody or antibody fragment of claim 1, and detecting whether the antibody or antibody fragment binds to a protease, which is indicative of the presence of the proteolytically form of an ADAM10 protease expressed by the tumour cell to thereby detect the tumour cell.

15. The method of claim 14, wherein the tumour cell is of a leukemia, lymphoma, lung cancer, colon cancer, breast cancer, adenoma, neuroblastoma, brain tumour, renal tumour, prostate cancer, sarcoma or melanoma.

16. A method of inhibiting an ADAM10 protease expressed by a cell, comprising contacting the antibody or antibody fragment of claim 1 to the ADAM10 protease expressed by the cell, to thereby at least partly inhibit a biological activity of the ADAM10 protease in the cell.

17. The method of claim 16, wherein the cell is a tumour cell.

18. The method of claim 17, wherein the tumour cell is of a leukemia, lymphoma, lung cancer, colon cancer, breast cancer, adenoma, neuroblastoma, brain tumour, renal tumour, prostate cancer, sarcoma or melanoma.

* * * * *

UNITED STATES PATENT AND TRADEMARK OFFICE
CERTIFICATE OF CORRECTION

PATENT NO. : 11,160,873 B2
APPLICATION NO. : 16/028130
DATED : November 2, 2021
INVENTOR(S) : Martin Lackmann et al.

It is certified that error appears in the above-identified patent and that said Letters Patent is hereby corrected as shown below:

On the Title Page

Item (72) Line 5: replace "Krew East (AU)" with "Kew East (AU)"

In the Claims

Claim 14, Column 55, Line 10: after "proteolytically" insert -- active --

Signed and Sealed this
Twelfth Day of July, 2022

Katherine Kelly Vidal
*Director of the United States Patent and Trademark Office*

SEQUENCE LISTING

<160> NUMBER OF SEQ ID NOS: 18

<210> SEQ ID NO 1
<211> LENGTH: 120
<212> TYPE: PRT
<213> ORGANISM: Artificial sequence
<220> FEATURE:
<223> OTHER INFORMATION: Monoclonal antibody sequence

<400> SEQUENCE: 1

```
Glu Val Gln Leu Gln Gln Ser Gly Ala Glu Leu Ala Arg Pro Gly Ser
1               5                   10                  15

Ser Val Lys Leu Ser Cys Lys Ala Ser Gly Tyr Thr Phe Thr Asn Tyr
            20                  25                  30

Trp Leu Gln Trp Val Lys Gln Arg Thr Gly Gln Gly Leu Glu Trp Ile
        35                  40                  45

Gly Ala Ile Tyr Pro Arg Asp Gly Asp Ala Lys Tyr Ser Gln Lys Phe
    50                  55                  60

Lys Asp Lys Ala Ser Leu Thr Val Asn Glu Ser Ser Ser Thr Ala Tyr
65                  70                  75                  80

Met His Leu Ser Ala Leu Ala Ser Glu Asp Ser Ala Val Tyr Tyr Cys
                85                  90                  95

Ala Arg Ala Asn Tyr Gly Leu Tyr Tyr Ala Met Asp Arg Trp Gly Gln
            100                 105                 110

Gly Thr Ser Val Thr Val Ser Ser
        115                 120
```

<210> SEQ ID NO 2
<211> LENGTH: 54
<212> TYPE: PRT
<213> ORGANISM: Artificial sequence
<220> FEATURE:
<223> OTHER INFORMATION: Monoclonal antibody sequence

<400> SEQUENCE: 2

```
Asp Ile Phe Leu Thr Gln Ser Pro Ala Asn Met Ser Val Ser Pro Gly
1               5                   10                  15

Glu Arg Val Ser Phe Ser Cys Arg Ala Ser Gln Asn Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser
    50
```

<210> SEQ ID NO 3
<211> LENGTH: 120
<212> TYPE: PRT

<213> ORGANISM: Artificial sequence
<220> FEATURE:
<223> OTHER INFORMATION: Humanized Ig sequence

<400> SEQUENCE: 3

```
Glu Val Gln Leu Gln Gln Ser Gly Ala Glu Leu Ala Lys Pro Gly Ser
1               5                   10                  15
Ser Val Lys Leu Ser Cys Lys Ala Ser Gly Tyr Thr Phe Thr Asn Tyr
            20                  25                  30
Trp Leu Gln Trp Val Lys Gln Arg Pro Gly Gln Gly Leu Glu Trp Ile
        35                  40                  45
Gly Ala Ile Tyr Pro Arg Asp Gly Asp Ala Lys Tyr Ser Gln Lys Phe
    50                  55                  60
Lys Asp Lys Ala Ser Ile Thr Val Asn Glu Ser Thr Ser Thr Ala Tyr
65                  70                  75                  80
Met His Leu Ser Ser Leu Arg Ser Glu Asp Thr Ala Val Tyr Tyr Cys
                85                  90                  95
Ala Arg Ala Asn Tyr Gly Leu Tyr Tyr Ala Met Asp Tyr Trp Gly Gln
            100                 105                 110
Gly Thr Thr Val Thr Val Ser Ser
        115                 120
```

<210> SEQ ID NO 4
<211> LENGTH: 108
<212> TYPE: PRT
<213> ORGANISM: Artificial sequence
<220> FEATURE:
<223> OTHER INFORMATION: Humanized Ig sequence

<400> SEQUENCE: 4

```
Asp Ile Val Leu Thr Gln Ser Pro Ala Phe Met Ser Val Ser Pro Gly
1               5                   10                  15
Glu Arg Val Ser Val Ser Cys Arg Ala Ser Gln Asn Ile Gly Thr Asn
            20                  25                  30
Ile His Trp Tyr Gln Gln Arg Pro Asp Gln Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Tyr Leu Thr Ile Asn Ser Val Glu Ser
65                  70                  75                  80
Glu Asp Ile Ala Val Tyr Phe Cys Gln Gln Ser Asn Arg Trp Pro Phe
                85                  90                  95
Thr Phe Gly Ser Gly Thr Lys Leu Glu Val Lys Arg
            100                 105
```

<210> SEQ ID NO 5
<211> LENGTH: 360
<212> TYPE: DNA
<213> ORGANISM: Artificial sequence
<220> FEATURE:
<223> OTHER INFORMATION: Humanized Ig nucleotide seq

<400> SEQUENCE: 5

```
gaggtgcagc tgcagcagtc cggagctgag ctggctaagc caggctccag cgtgaagctg      60
tcttgcaagg cctccggcta caccttcaca aactattggc tgcagtgggt gaagcagagg     120
ccaggacagg gactggagtg gatcggcgcc atctacccta gggacggcga tgctaagtat     180
agccagaagt ttaaggacaa ggcctctatc accgtgaacg agtccaccag cacagcttac     240
```

```
atgcacctgt cttccctgag gagcgaggac acagccgtgt actattgtgc ccgggctaat      300
tatggcctgt actatgctat ggatagatgg ggccagggca ccacagtgac cgtgagctct      360
```

<210> SEQ ID NO 6
<211> LENGTH: 324
<212> TYPE: DNA
<213> ORGANISM: Artificial sequence
<220> FEATURE:
<223> OTHER INFORMATION: Humanized Ig nucletide sequence

<400> SEQUENCE: 6

```
gacatcgtgc tgacccagtc tccagccttc atgtccgtga gccccggcga gagggtgtcc       60
gtgtcctgcc gggcttctca gaacatcggc acaaatatcc actggtacca gcagagaccc      120
gatcagtccc ctcgcctgct gatcaagtat gccagcgagt ctatctccgg catccctagc      180
aggttcagcg gctctggctc cggaaccgac ttttacctga caatcaacag cgtggagtct      240
gaggatatcg ccgtgtactt ttgtcagcag tccaatagat ggccattcac ctttggcagc      300
ggcacaaagc tggaggtgaa gcgt                                             324
```

<210> SEQ ID NO 7
<211> LENGTH: 106
<212> TYPE: PRT
<213> ORGANISM: Homo sapiens

<400> SEQUENCE: 7

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 8
<211> LENGTH: 329
<212> TYPE: PRT
<213> ORGANISM: Homo sapiens

<400> SEQUENCE: 8

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
```

```
                    85                  90                  95
Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 9
<211> LENGTH: 324
<212> TYPE: DNA
<213> ORGANISM: Homo sapiens

<400> SEQUENCE: 9
actgtggctg caccatctgt cttcatcttc ccaccctccg acgagcagct gaagtccggc      60
accgcctccg tggtgtgcct gctgaacaac ttctaccccc gcgaggccaa ggtgcagtgg     120
aaggtggaca acgccctgca gtccggcaac tcccaggaat ccgtcaccga gcaggactcc     180
aaggacagca cctactccct gtcctccacc ctgaccctgt ccaaggccga ctacgagaag     240
cacaaggtgt acgcctgcga agtgacccac cagggcctgt ccagccccgt gaccaagtcc     300
ttcaaccggg gcgagtgctg atga                                            324

<210> SEQ ID NO 10
<211> LENGTH: 993
<212> TYPE: DNA
<213> ORGANISM: Homo sapiens

<400> SEQUENCE: 10
tccaccaagg gcccatcggt cttccccctg gccccatcct ccaagtccac ctctgcggc       60 accgccgctc tgggctgcct ggtgaaagac tacttccccg agcccgtgac cgtgtcctgg     120
```

```
aactctggcg ccctgacctc cggcgtgcac acctttccag ccgtgctgca gtcctccggc    180
ctgtactccc tgtcctccgt ggtgacagtg ccctcctcca gcctgggcac ccagacctac    240
atctgcaacg tgaaccacaa gccctccaac accaaggtgg acaagaaggt ggaacccaag    300
tcctgcgaca gaccccacac ctgtcccccc tgccctgccc ctgaactgct gggcggaccc    360
tccgtgttcc tgttcccccc aaagcccaag gacaccctga tgatctcccg gacccccgaa    420
gtgacctgcg tggtggtgga cgtgtcccac gaggaccctg aagtgaagtt caattggtac    480
gtggacggcg tggaagtgca caatgccaag accaagccca gagaggaaca gtacaactcc    540
acctaccggg tggtgtccgt gctgaccgtg ctgcaccagg attggctgaa cggcaaagag    600
tacaagtgca aggtctccaa caaggccctg ccagccccca tcgaaaagac catctccaag    660
gccaagggcc agccccgcga gcctcaggtg tacaccctgc ctcccagccg ggacgagctg    720
accaagaacc aggtgtccct gacctgtctg gtgaaaggct tctaccctc cgatatcgcc    780 gtggaatggg agtccaacgg ccagcccgag aacaactaca agaccacccc cctgtgctg    840 gactccgacg gctcattctt cctgtactcc aagctgaccg tggacaagtc ccggtggcag    900
cagggcaacg tgttctcctg ctccgtgatg cacgaggccc tgcacaacca ctacacccag    960
aagtccctgt ccctgagccc cggcaagtga tga                                993
```

<210> SEQ ID NO 11
<211> LENGTH: 5
<212> TYPE: PRT
<213> ORGANISM: Homo sapiens

<400> SEQUENCE: 11

Cys His Val Cys Cys
1               5

<210> SEQ ID NO 12
<211> LENGTH: 748
<212> TYPE: PRT
<213> ORGANISM: Homo sapiens

<400> SEQUENCE: 12

Met Val Leu Leu Arg Val Leu Ile Leu Leu Ser Trp Ala Ala Gly
1               5                   10                  15

Met Gly Gly Gln Tyr Gly Asn Pro Leu Asn Lys Tyr Ile Arg His Tyr
                20                  25                  30

Glu Gly Leu Ser Tyr Asn Val Asp Ser Leu His Gln Lys His Gln Arg
            35                  40                  45

Ala Lys Arg Ala Val Ser His Glu Asp Gln Phe Leu Arg Leu Asp Phe
        50                  55                  60

His Ala His Gly Arg His Phe Asn Leu Arg Met Lys Arg Asp Thr Ser
65                  70                  75                  80

Leu Phe Ser Asp Glu Phe Lys Val Glu Thr Ser Asn Lys Val Leu Asp
                85                  90                  95

Tyr Asp Thr Ser His Ile Tyr Thr Gly His Ile Tyr Gly Glu Glu Gly
            100                 105                 110

Ser Phe Ser His Gly Ser Val Ile Asp Gly Arg Phe Glu Gly Phe Ile
        115                 120                 125

Gln Thr Arg Gly Gly Thr Phe Tyr Val Glu Pro Ala Glu Arg Tyr Ile
    130                 135                 140

Lys Asp Arg Thr Leu Pro Phe His Ser Val Ile Tyr His Glu Asp Asp
145                 150                 155                 160

-continued

```
Ile Asn Tyr Pro His Lys Tyr Gly Pro Gln Gly Gly Cys Ala Asp His
            165                 170                 175

Ser Val Phe Glu Arg Met Arg Lys Tyr Gln Met Thr Gly Val Glu Glu
            180                 185                 190

Val Thr Gln Ile Pro Gln Glu Glu His Ala Ala Asn Gly Pro Glu Leu
            195                 200                 205

Leu Arg Lys Lys Arg Thr Thr Ser Ala Glu Lys Asn Thr Cys Gln Leu
    210                 215                 220

Tyr Ile Gln Thr Asp His Leu Phe Phe Lys Tyr Gly Thr Arg Glu
225                 230                 235                 240

Ala Val Ile Ala Gln Ile Ser Ser His Val Lys Ala Ile Asp Thr Ile
                245                 250                 255

Tyr Gln Thr Thr Asp Phe Ser Gly Ile Arg Asn Ile Ser Phe Met Val
            260                 265                 270

Lys Arg Ile Arg Ile Asn Thr Thr Ala Asp Glu Lys Asp Pro Thr Asn
        275                 280                 285

Pro Phe Arg Phe Pro Asn Ile Gly Val Glu Lys Phe Leu Glu Leu Asn
    290                 295                 300

Ser Glu Gln Asn His Asp Asp Tyr Cys Leu Ala Tyr Val Phe Thr Asp
305                 310                 315                 320

Arg Asp Phe Asp Asp Gly Val Leu Gly Leu Ala Trp Val Gly Ala Pro
                325                 330                 335

Ser Gly Ser Ser Gly Gly Ile Cys Glu Lys Ser Lys Leu Tyr Ser Asp
            340                 345                 350

Gly Lys Lys Lys Ser Leu Asn Thr Gly Ile Ile Thr Val Gln Asn Tyr
        355                 360                 365

Gly Ser His Val Pro Pro Lys Val Ser His Ile Thr Phe Ala His Glu
    370                 375                 380

Val Gly His Asn Phe Gly Ser Pro His Asp Ser Gly Thr Glu Cys Thr
385                 390                 395                 400

Pro Gly Glu Ser Lys Asn Leu Gly Gln Lys Glu Asn Gly Asn Tyr Ile
            405                 410                 415

Met Tyr Ala Arg Ala Thr Ser Gly Asp Lys Leu Asn Asn Asn Lys Phe
        420                 425                 430

Ser Leu Cys Ser Ile Arg Asn Ile Ser Gln Val Leu Glu Lys Lys Arg
    435                 440                 445

Asn Asn Cys Phe Val Glu Ser Gly Gln Pro Ile Cys Gly Asn Gly Met
    450                 455                 460

Val Glu Gln Gly Glu Glu Cys Asp Cys Gly Tyr Ser Asp Gln Cys Lys
465                 470                 475                 480

Asp Glu Cys Cys Phe Asp Ala Asn Gln Pro Glu Gly Arg Lys Cys Lys
                485                 490                 495

Leu Lys Pro Gly Lys Gln Cys Ser Pro Ser Gln Gly Pro Cys Cys Thr
            500                 505                 510

Ala Gln Cys Ala Phe Lys Ser Lys Ser Glu Lys Cys Arg Asp Asp Ser
        515                 520                 525

Asp Cys Ala Arg Glu Gly Ile Cys Asn Gly Phe Thr Ala Leu Cys Pro
    530                 535                 540

Ala Ser Asp Pro Lys Pro Asn Phe Thr Asp Cys Asn Arg His Thr Gln
545                 550                 555                 560

Val Cys Ile Asn Gly Gln Cys Ala Gly Ser Ile Cys Glu Lys Tyr Gly
                565                 570                 575

Leu Glu Glu Cys Thr Cys Ala Ser Ser Asp Gly Lys Asp Asp Lys Glu
```

```
                580             585             590
Leu Cys His Val Cys Cys Met Lys Lys Met Asp Pro Ser Thr Cys Ala
            595                 600                 605
Ser Thr Gly Ser Val Gln Trp Ser Arg His Phe Ser Gly Arg Thr Ile
            610                 615                 620
Thr Leu Gln Pro Gly Ser Pro Cys Asn Asp Phe Arg Gly Tyr Cys Asp
625                 630                 635                 640
Val Phe Met Arg Cys Arg Leu Val Asp Ala Asp Gly Pro Leu Ala Arg
                645                 650                 655
Leu Lys Lys Ala Ile Phe Ser Pro Glu Leu Tyr Glu Asn Ile Ala Glu
                660                 665                 670
Trp Ile Val Ala His Trp Trp Ala Val Leu Leu Met Gly Ile Ala Leu
                675                 680                 685
Ile Met Leu Met Ala Gly Phe Ile Lys Ile Cys Ser Val His Thr Pro
                690                 695                 700
Ser Ser Asn Pro Lys Leu Pro Pro Lys Pro Leu Pro Gly Thr Leu
705                 710                 715                 720
Lys Arg Arg Arg Pro Pro Gln Pro Ile Gln Gln Pro Gln Arg Gln Arg
                725                 730                 735
Pro Arg Glu Ser Tyr Gln Met Gly His Met Arg Arg
                740                 745

<210> SEQ ID NO 13
<211> LENGTH: 10
<212> TYPE: PRT
<213> ORGANISM: Artificial Sequence
<220> FEATURE:
<223> OTHER INFORMATION: Monoclonal antibody sequence

<400> SEQUENCE: 13

Gly Tyr Thr Phe Thr Asn Tyr Trp Leu Gln
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Monoclonal antibody sequence

<400> SEQUENCE: 14

Ala Ile Tyr Pro Arg Asp Gly Asp Ala Lys Tyr Ser Gln Lys Phe Lys
1               5                   10                  15
Asp

<210> SEQ ID NO 15
<211> LENGTH: 11
<212> TYPE: PRT
<213> ORGANISM: Artificial Sequence
<220> FEATURE:
<223> OTHER INFORMATION: Monoclonal antibody sequence

<400> SEQUENCE: 15

Ala Asn Tyr Gly Leu Tyr Tyr Ala Met Asp Arg
1               5                   10

<210> SEQ ID NO 16
<211> LENGTH: 11
<212> TYPE: PRT
<213> ORGANISM: Artificial Sequence
<220> FEATURE:
```

```
<223> OTHER INFORMATION: Monoclonal antibody sequence

<400> SEQUENCE: 16

Arg Ala Ser Gln Asn Ile Gly Thr Asn Ile His
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Monoclonal antibody sequence

<400> SEQUENCE: 17

Tyr Ala Ser Glu Ser Ile Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Monoclonal antibody sequence

<400> SEQUENCE: 18

Gln Gln Ser Asn Arg Trp Pro Phe Thr
1               5
```